US011492614B2

(12) United States Patent
McLaughlin et al.

(10) Patent No.: US 11,492,614 B2
(45) Date of Patent: Nov. 8, 2022

(54) STEM LOOP RNA MEDIATED TRANSPORT OF MITOCHONDRIA GENOME EDITING MOLECULES (ENDONUCLEASES) INTO THE MITOCHONDRIA

(71) Applicant: Research Institute at Nationwide Children's Hospital, Columbus, OH (US)

(72) Inventors: Kenneth John McLaughlin, Columbus, OH (US); Syed-Rehan Ashfaq Hussain, Columbus, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 520 days.

(21) Appl. No.: 16/461,355

(22) PCT Filed: Nov. 15, 2017

(86) PCT No.: PCT/US2017/061876
§ 371 (c)(1),
(2) Date: May 15, 2019

(87) PCT Pub. No.: WO2018/093954
PCT Pub. Date: May 24, 2018

(65) Prior Publication Data

US 2020/0032251 A1 Jan. 30, 2020

Related U.S. Application Data

(60) Provisional application No. 62/423,140, filed on Nov. 16, 2016.

(51) Int. Cl.
*C12N 15/11* (2006.01)
*C12N 9/22* (2006.01)
*C12N 15/86* (2006.01)
*C12N 15/90* (2006.01)

(52) U.S. Cl.
CPC ................ *C12N 15/11* (2013.01); *C12N 9/22* (2013.01); *C12N 15/86* (2013.01); *C12N 15/907* (2013.01); *C12N 2310/20* (2017.05); *C12N 2310/531* (2013.01); *C12N 2750/14141* (2013.01); *C12N 2800/80* (2013.01)

(58) Field of Classification Search
CPC .......... C12N 15/11; C12N 9/22; C12N 15/86; C12N 15/907; C12N 2310/20; C12N 2310/531
See application file for complete search history.

(56) References Cited

U.S. PATENT DOCUMENTS

2012/0283317 A1 11/2012 Teitell et al.

FOREIGN PATENT DOCUMENTS

CN 105602935 A 5/2016
WO WO-2016/040030 A1 3/2016

OTHER PUBLICATIONS

International Search Report and Written Opinion issued in PCT/US2017/061876 dated Feb. 16, 2018, 12 pages.
Jo et al., "Efficient Mitochondrial Genome Editing by CRISPR/Cas9", Biomed Res Int, Sep. 10, 2015, vol. 2015, No. 305716, pp. 1-10.
Lindahl et al., "Functional equivalence of hairpins in the RNA subunits of RNase MRP and RNase P in *Saccharomyces cerevisiae*", RNA, May 1, 2000, vol. 6, No. 5, pp. 653-658.
Nissism et al., "Multiplexed and programmable regulation of gene networks with an integrated RNA and CRISPR/Cas toolkit in human cells", Mol Cell, May 15, 2014, vol. 54, No. 4, pp. 698-710.
Bacman, et al., "Specific elimination of mutant mitochondrial genomes in patient-derived cells by mitoTALENs", Nat Med, Sep. 2013, 19(9), pp. 1111-1113.
Gammage, et al., "Mitochondrially targeted ZFNs for selective degradation of pathogenic mitochondrial genomes bearing large-scale deletions or point mutations", EMBO Mol Med, Apr. 2014, 6(4), pp. 458-466.
Hsu, et al., "Development and applications of CRISPR-Cas9 for genome engineering", Cell, Jun. 5, 2014, 157(6), pp. 1262-1278.
Reddy, et al., "Selective elimination of mitochondrial mutations in the germline by genome editing", Cell, Apr. 23, 2015, 161(3), pp. 459-469.
Wang, et al. "PNPASE regulates RNA import into mitochondria", Cell, Aug. 6, 2010, 142(3), pp. 456-467.

*Primary Examiner* — Paul J Holland
(74) *Attorney, Agent, or Firm* — Foley & Lardner LLP

(57) ABSTRACT

The present disclosure relates to a novel CRISPR-Cas9 based system for editing mitochondrial DNA. Aspects of the disclosure provide for mitochondrial translocation of both the guide RNA and the recombinant Cas9 nuclease.

19 Claims, 27 Drawing Sheets

Specification includes a Sequence Listing.

SEQ ID NO.: 16

5' UCUCCCUGAGCUUCAGGGAG-ttaattaa CGTACTATAATCATGGCCCG

SEQ ID NO.: 17

RNase P (RP) Loop region: UCUCCCUGAGCUUCAGGGAG

SEQ ID NO.: 18

(spacer/rest site): NNNNNN pX-MLS-mSpCas9 with RP-loop

SEQ ID NO.: 19

| 40ng DNA | Ct RP-loop | Ct Nuclear SdhA |
|---|---|---|
| Total-naive | 31.92 | 30.53 |
| Mito-naive | 32.98 | 33.55 |
| Mito-sgRNA | 20.24 | 34.98 |

STEM LOOP RNA MEDIATED TRANSPORT OF MITOCHONDRIA GENOME EDITING MOLECULES (ENDONUCLEASES) INTO THE MITOCHONDRIA

CROSS REFERENCE TO RELATED APPLICATION

This application is a U.S. national stage application under 35 U.S.C. § 371 of International Application No. PCT/US2017/061876, filed Nov. 15, 2017, which in turn claims priority under 35 U.S.C. § 119(e) to U.S. Provisional Application No. 62/423,140, filed Nov. 16, 2016, the content of each of which is hereby incorporated by reference in their entirety.

SEQUENCE LISTING

The instant application contains a Sequence Listing which has been submitted electronically in ASCII format and is hereby incorporated by reference in its entirety. Said ASCII copy, created on Dec. 21, 2017, is named 106887-7082_SL.txt and is 56,328 bytes in size.

FIELD

The present invention generally relates to systems, methods, and compositions used for gene editing and the control of gene expression in mitochondria.

BACKGROUND

Pathogenic mutations and deletions in the maternally inherited mitochondrial genome (mtDNA) affect as many as one in five hundred births and cause conditions with limited treatment options and poor prognosis. Clinical manifestations of heteroplasmy for defective mitochondria include variable multisystem disorders such as Pearson and Kearns-Sayre Syndromes, progressive external ophthalmoplegia, mitochondrial myopathy, encephalopathy, lactic acidosis, stroke-like syndrome (MELAS), myoclonic epilepsy with ragged-red fibers (MERFF), and Leigh Syndrome. Other specific manifestations caused by mitochondrial disorders include Leber hereditary optic neuropathy (LHON). Many of these clinical manifestations derive from deleterious single base substitutions in the mitochondrial genome.

Animal models of mitochondrial diseases are essential to evaluate cause-effect relationships of mtDNA mutations, determine pathophysiological processes, and to assess therapeutic strategies. However, their effective generation has been hampered by inaccessibility of mtDNA to gene targeting, and limited transmission of mutant mitochondria via the female germline. This disclosure describes novel approaches to edit mitochondrial DNA and produce animals heteroplasmic for mutant mitochondria.

SUMMARY

Aspects of the present disclosure relate to a recombinant expression system that enables delivery of clustered regularly interspaced short palindromic repeats (CRISPR)-based gene editing tools to the mitochondrion. In some embodiments, gene defects in mitochondria are repaired using the disclosed gene editing system. In other embodiments, the tools of the present disclosure are used to shift mitochondrial heteroplasmy in a cell or animal.

This disclosure also provides for the development of a unique tool to target mitochondrial DNA by modifying the CRISPR/Cas9 system for genome editing in mitochondria.

The CRISPR/Cas9 system for gene editing has two major components. The first component is a guide RNA (gRNA) with a scaffold that includes: (i) a target-directed 20 nucleotide sequence; (ii) CRISPR RNA (crRNA); and (iii) trans-activating crRNA (tracrRNA). The second component is a Cas9 endonuclease to generate double-stranded breaks (DSB) or single stranded breaks in DNA. Cas9 may be edited to contain nuclear localization signals (NLS) to direct it to the nucleus. For nuclear gene editing, a gRNA sequence complexes with a Cas9 protein with NLS. The 20 nucleotide target sequence of the gRNA guides Cas9 to a region of interest on the genome where it generates a DSB.

Use of the CRISPR/Cas9 system has advantages for gene editing over TALEN endonucleases and other alternative gene editing strategies because CRISPR can be introduced into patients using AAV gene therapy vectors. See Bacman et al. (2013) Nature Medicine 19(9):1111-1113. However, currently it is not possible to use the CRISPR/Cas9 system to efficiently target the mitochondrial genome because Cas9 does not have mitochondrial localization signals (MLS) and gRNA cannot independently translocate to mitochondria. These two are essential limiting factors because Cas9 has to bind in a proper conformation with gRNA and target DNA inside the mitochondria. Therefore, even if the gRNA/Cas9 complex is formed in the cytoplasm, the structural conformation may be transiently changed while translocating through mitochondrial pores.

This disclosure describes a mito-CRISPR/Cas9 system that can be efficiently imported into mitochondria to specifically edit a mtDNA target sequence. The present disclosure describes two major modifications to the CRISPR/Cas9 system that allow it to edit mitochondrial DNA. First, this modified system replaces the NLS sequences with MLS in Cas9 so that the endonuclease can translocate across the mitochondrial membranes. Second, a 20 nucleotide sequence of RNase P RNA called the RNA loop sequence (RP-loop) is fused to the 5' terminal end of a guide RNA sequence to create a hybrid gRNA. The RP loop was previously shown to translocate non-mitochondrial RNA to the mitochondrial inner membrane by binding to PANPASE (polynucleotide phosphorylase). See Wang et al. (2010) Cell 142: 456-467.

This disclosure also describes a mito-CRISPR/Cas9 system that comprises an alternative approach to a viral vector delivery system. In some embodiments, the system comprises a lipid such as C12-200 that is capable of forming a lipid nanoparticle comprising an mRNA encoding an mitochondrial-targeted Cas9. In some embodiments, the system further comprises a viral vector encoding a guie RNA and optionally a repair template RNA.

In some embodiments, the hybrid gRNA targets mtDNA in need of repair.

In some embodiments, the Cas9 has one or more MLS sequences to facilitate transport to the mitochondria.

In some embodiments, MLS sequences flank the Cas9 polynucleotide.

In some embodiments, the Cas9 is codon-optimized for expression in a subject.

In some embodiments, the Cas9 nuclease can be a nickase.

In some embodiments, the Cas9 nuclease can be spCas9, saCas9, C2c1, or Cpf1.

In some embodiments, the mito-CRISPR/Cas9 system further comprises a donor polynucleotide encoding a desired mtDNA edited sequence.

In some embodiments, the mito-CRISPR/Cas9 system disclosed herein can be used to repair damaged mitochondrial DNA.

In some embodiments, the mito-CRISPR/Cas9 system is encoded on a recombinant AAV vector with tropism for a desired human tissue type.

In some embodiments, the gRNA is produced in vitro through in vitro transcription.

In another aspect, this disclosure describes viral particles comprising a mito-CRISPR/Cas9 system.

In some aspects of this disclosure, the hybrid gRNA targets the murine mitochondrial NADH dehydrogenase subunit 4 (mtND4) gene. ND4 mutations are known to cause MELAS syndrome and LHON in humans.

In further aspects of this disclosure, the mito-CRISPR/Cas9 system disclosed herein can be used to shift heteroplasmy in cells.

In some embodiments, the cells are cybrid embryonic stem cells.

In another aspect, the mito-CRISPR/Cas9 system disclosed herein can be used to generate mutant mouse strains via germline transmission using a germline competent female stem cell cell line. These mouse strains can be used as tools to model mitochondrial diseases and conditions.

In some aspects of this disclosure, the mito-CRISPR/Cas9 system disclosed herein can be used to treat mitochondrial conditions in a subject.

In a further aspect, the mito-CRISPR/Cas9 system disclosed herein can be used to assay for the effective editing of mtDNA.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2A depicts the 20 nucleotide RP loop sequence fragment used in the hybrid guide RNA. FIG. 2A discloses SEQ ID NO: 36. FIG. 2B depicts a model of the secondary secondary structure of full length hybrid gRNA. FIG. 2B discloses SEQ ID NO: 37. The gRNA sequence was tested in silico for the formation of a loop structure using M-fold RNA secondary structure analysis tool. The hybrid gRNA depicted is 124 nucleotides in length and comprises a 20 nucleotide RP-loop (shaded region), an 8 nucleotide spacer, a 20 nucleotide target sequence, and a 76 nucleotide chimeric scaffold.

FIG. 7A depicts mRNA expression of the mtND4 gene in cells transfected with either a control construct or a gRNA targeting mtND4 but lacking an RP loop. There was no statistical difference in expression between the control and gRNA cells, indicating that the gRNA was not effective in knocking down mitochondrial gene expression in the absence of an RP loop. FIG. 7B depicts mRNA expression of the mtND4 gene in cells transfected with either a control construct or a hybrid gRNA targeting mtND4. Expression of mtND4 was significantly reduced in the hybrid gRNA cells indicating that the presence of the RP loop facilitated gene editing in the mitochondria.

FIG. 18A Depicts the first nucleotides of SEQ ID NO.: 32. FIG. 18B Depicts a continuation of SEQ ID NO.: 32. FIG. 18C Depicts a continuation of SEQ ID NO.: 32. FIG. 18D Depicts a continuation of SEQ ID NO.: 32. FIG. 18E Depicts a continuation of SEQ ID NO.: 32.

FIG. 19A Depicts the first nucleotides of SEQ ID NO.: 33. FIG. 19B Depicts a continuation of SEQ ID NO.: 33. FIG. 19C Depicts a continuation of SEQ ID NO.: 33. FIG. 19D Depicts a continuation of SEQ ID NO.: 33.

FIG. 20A Depicts the first nucleotides of SEQ ID NO.: 34. FIG. 20B Depicts a continuation of SEQ ID NO.: 34. FIG. 20C Depicts a continuation of SEQ ID NO.: 34. FIG. 20D Depicts a continuation of SEQ ID NO.: 34. FIG. 20E Depicts a continuation of SEQ ID NO.: 34.

DETAILED DESCRIPTION

Definitions

Figure 1:
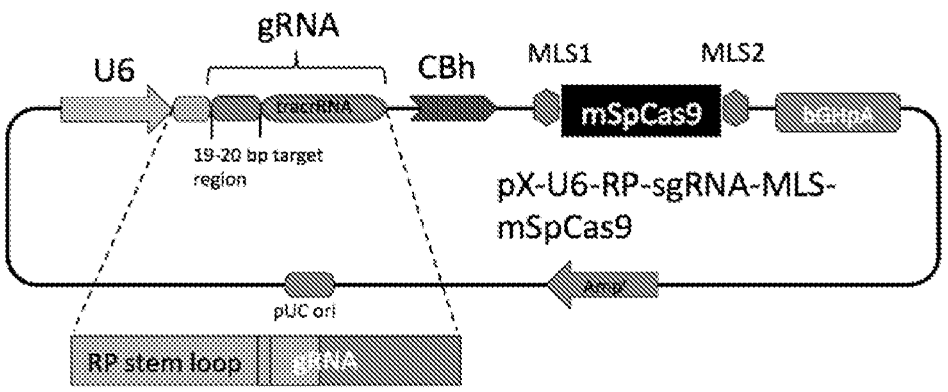
FIG. 1. Diagram of an embodiment of the mito-CRISPR/Cas9 gene editing system of the disclosed invention. The pX-U6-RP-sgRNA-MLS-mSpCas9 expression vector shown contains both the MLS tagged Cas9 and the hybrid RP loop guideRNA (gRNA). Enlarged inset depicts the hybrid guide RNA polynucleotide comprising the RP stem loop, a spacer, the 19-20 bp target region, and the tracrRNA/crRNA scaffold region. The hybrid gRNA is under the control of a U6 promoter. Downstream of the gRNA is a CBh promoter to regulate expression of the Cas9 polynucleotide. The mouse-optimized *Streptococcus pyogenes* Cas9 (mSpCas9) polynucleotide is flanked by a mitochondrial localization signal (MLS) on either side. Downstream of the Cas9 polynucleotide is a bGHpA sequence encoding a polyadenylation signal. The expression vector also encodes an ampicillin resistance gene ($Amp^r$) and an origin of replication (pUC ori).

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure, the preferred methods, devices, and materials are now described. All technical and patent publications cited herein are incorporated herein by reference in their entirety. Nothing herein is to be construed as an admission that the disclosure is not entitled to antedate such disclosure by virtue of prior disclosure.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Techique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3rd edition (Cold Spring Harbor Laboratory Press (2002)); Sohail (ed.) (2004) Gene Silencing by RNA Interference: Technology and Application (CRC Press).

All numerical designations, e.g., pH, temperature, time, concentration, and molecular weight, including ranges, are approximations which are varied (+) or (−) by increments of 0.1 or 1.0, where appropriate. It is to be understood, although not always explicitly stated that all numerical designations are preceded by the term "about." It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this disclosure or process steps to produce a composition or achieve an intended result. Embodiments defined by each of these transition terms are within the scope of this invention.

The term "isolated" as used herein with respect to nucleic acids, such as DNA or RNA, refers to molecules separated from other DNAs or RNAs, respectively that are present in the natural source of the macromolecule. The term "isolated nucleic acid" is meant to include nucleic acid fragments which are not naturally occurring as fragments and would not be found in the natural state. The term "isolated" is also used herein to refer to polypeptides, proteins and/or host cells that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the following Internet address: www.ncbi.nlm.nih.gov/cgi-bin/BLAST.

An equivalent nucleic acid, polynucleotide or oligonucleotide is one having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to the reference nucleic acid, polynucleotide, or oligonucleotide, or alternatively an equivalent nucleic acid hybridizes under conditions of high stringency to a reference polynucleotide or its complement.

An equivalent polypeptide or protein is one having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to the reference polypeptide or protein, or alternatively an equivalent polypeptide or protein is one encoded by nucleic acid that hybridizes under conditions of high stringency to a polynucleotide or its complement that encodes the reference polypeptide or protein.

The expression "amplification of polynucleotides" includes methods such as PCR, transcription, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

A "gene" refers to a polynucleotide containing at least one open reading frame (ORF) that is capable of encoding a particular polypeptide or protein after being transcribed and translated.

The term "gene editing" or "genome editing" refers to a type of genetic engineering in which DNA or RNA is inserted, deleted or replaced in the genome of a living organism using engineered nucleases. Non-limiting examples of nucleases include CRISPR-associated enzymes, transcription-activator like effectors (TALENs), meganucleases, and zinc finger proteins (ZFNs). These nucleases create site-specific double-strand breaks or (DSBs) at desired locations in the genome. The induced double-strand breaks are repaired through nonhomologous end-joining (NHEJ) or homologous recombination (HR), resulting in targeted mutations. Gene editing may also refer to use of nickases that create single-strand breaks at desired locations in the genome.

Non-limiting examples of gene edits that may be performed by use of the disclosed invention include knockdown of gene expression (reducing gene expression), gene knockouts (e.g. gene inactivation), gene knock-ins (e.g. gene delivery), editing of multiple polynucleotide sequences at one time, repair or introduction of deletions, point mutations, or insertions, RNA editing or targeting, delivery of gene drives, genetic depletion, and controlled (e.g. inducible) genome editing. As used herein, gene therapy is the use of gene editing to repair a defective gene at its natural, endogenous location.

The term "express" refers to the production of a gene product.

As used herein, "expression" refers to the process by which polynucleotides are transcribed into RNA. Types of RNA that may be transcribed from a polynucleotide template include tRNA, rRNA, miRNA, snRNA, mRNA, and other RNAs involved in protein synthesis, post-transcriptional modification, DNA replication, gene regulation, and parasitic RNAs such as viral genomes. Expression also refers to the process by which the transcribed RNA is subsequently being translated into peptides, polypeptides, or proteins. If the polynucleotide is derived from genomic DNA, expression may include splicing and other post-transcriptional processing of the mRNA in a eukaryotic cell.

A "gene product" or alternatively a "gene expression product" may refer to the amino acid (e.g., peptide or polypeptide) generated when a gene is transcribed and translated or any other product of transcription such as a functional RNA (e.g. tRNA, siRNA, or miRNA).

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" intends the polynucleotides are arranged in a manner that allows them to function in a cell. In one aspect, this invention provides promoters operatively linked to the downstream sequences.

The term "encode" as it is applied to polynucleotides refers to a polynucleotide which is said to "encode" a polypeptide if, in its native state or when manipulated by methods well known to those skilled in the art, it can be transcribed and/or translated to produce an RNA or a polypeptide and/or a fragment thereof. The antisense strand is the complement of such a nucleic acid, and the encoding sequence can be deduced therefrom.

A "probe" when used in the context of polynucleotide manipulation refers to an oligonucleotide that is provided as a reagent to detect a target potentially present in a sample of interest by hybridizing with the target. Usually, a probe will comprise a detectable label or a means by which a label can be attached, either before or subsequent to the hybridization reaction. Alternatively, a "probe" can be a biological compound such as a polypeptide, antibody, or fragments thereof that is capable of binding to the target potentially present in a sample of interest.

"Detectable labels" or "markers" include, but are not limited to radioisotopes, fluorochromes, chemiluminescent compounds, dyes, enzymes and other proteins. Detectable labels can also be attached to a polynucleotide, polypeptide, antibody or composition described herein.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in MacPherson et al. (1991) PCR 1: A Practical Approach (IRL Press at Oxford University Press). All processes of producing replicate copies of a polynucleotide, such as PCR or gene cloning, are collectively referred to herein as "replication." A primer can also be used as a probe in hybridization reactions, such as Southern or Northern blot analyses. Sambrook and Russell (2001), infra.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

The term "propagate" means to grow a cell or population of cells. The term "growing" also refers to the proliferation of cells in the presence of supporting media, nutrients, growth factors, support cells, or any chemical or biological compound necessary for obtaining the desired number of cells or cell type.

The term "culturing" refers to the in vitro propagation of cells or organisms on or in media of various kinds. It is understood that the descendants of a cell grown in culture may not be completely identical (i.e., morphologically, genetically, or phenotypically) to the parent cell.

The term "mitochondrion" is a double membrane-bound organelle found in eukaryotic organisms. Mitochondria generate cellular power by supplying adenosine triphosphate (ATP), a source of chemical energy. In addition to creating ATP, mitochondria are involved in other processes, such as signaling, cellular differentiation, cell death, and proliferation. Mitochondrial biogenesis can be coordinated with these processes. Mitochondria comprise an outer mitochondrial membrane, an intermembrane space, an inner mitochondrial membrane, a cristae space formed by infoldings of the inner membrane, and a matrix which comprises the space within the inner membrane.

Mitochondria contain their own genome (mtDNA) that replicates independently from the nuclear genome of a cell. In humans, the mitochondrial genome is a circular DNA molecule approximately 16 kilobases long and encoding approximately 37 genes. A single mitochondrion may contain between one to 10 copies of mtDNA. While some of the proteins necessary for mitochondrial function are encoded by the mitochondrial genome, many essential mitochondria-related genes are encoded nuclear DNA. The number of genes encoded by the nuclear and mitochondrial genomes differs between organisms. Further, some organisms contain mitochondria that use non-standard variations of the genetic code such as AUA, AUC, and AUU start codons.

Mitochondria may undergo a division process of binary fission or they may elongate in a process of mitochondrial fusion. In some eukaryotes, binary fission and fusion processes are linked to the cell cycle. For example, the mitochondria within a cell may replicate the mtDNA and divide in coordination with nuclear division. In other eukaryotes such as mammals, mitochondria may replicate their DNA and divide mainly in response to cellular energy demands, rather than in step with the cell cycle. When the cell requires a high amount of energy, mitochondria grow and divide. In contrast, when cells are senescent or require very little energy, mitochondria are destroyed or become inactive.

The pattern of mtDNA inheritance is different from that of nuclear DNA. While nuclear DNA is inherited from both parents, mtDNA is typically inherited only from a single parent. In humans, mitochondrial DNA is usually inherited from the female parent. Though paternal mitochondria may enter the egg during fertilization, they typically do not contribute much genetic information to the embryo because they are ubiquitinylated and destroyed. Maternal inheritance of mtDNA is seen in most organisms, including the majority of animals. However, mitochondria in some species (e.g. conifers) can be inherited paternally.

Mitochondria have been implicated in several human diseases and conditions, including cardiac dysfunction, heart failure, aging, neurological and autism. High levels of oxidative stress from the mitochondria's function in producing ATP may result in damage of the mtDNA. Mutations in mtDNA are associated with a broad spectrum of clinical phenotypes ranging from mild symptoms to debilitating multi-organ syndromes. Diseases caused by defective mitochondria include Pearson and Kearns-Sayre Syndromes, progressive external ophthalmoplegia, mitochondrial myopathy, encephalopathy, lactic acidosis, stroke-like syndrome (MELAS), myoclonic epilepsy with ragged-red fibers (MERFF), and Leigh Syndrome. Other specific manifestations caused by mitochondrial disorders include Leber hereditary optic neuropathy (LHON). Diseases such as Kearns-Sayre syndrome, Pearson syndrome, and progressive external ophthalmoplegia are thought to be due to large-scale mtDNA rearrangements, whereas other diseases such as MELAS syndrome, Leber's hereditary optic neuropathy, myoclonic epilepsy with ragged red fibers (MERRF), and others are due to point mutations in mtDNA.

As used herein, "heteroplasmy" describes the presence of more than one type of mitochondrial genome within a single cell or individual. Heteroplasmy may be calculated as the ratio of normal versus mutant mtDNA sequence variants within a cell. Heteroplasmy is a major determinant of the manifestations of mitochondrial disease. Because a single cell may contain thousands of mitochondria, nearly all organisms have low levels of mitochondrial variants, conferring some detectable ratio of heteroplasmy. Even if a single mutation is rare, its frequency can expand over time through repeated mitotic segregation and clonal expansion. This dominance of the mtDNA pool may result in physiological consequences. Molecular tools to manipulate these heteroplasmy ratios offer therapeutic options by shifting the balance of mtDNA toward a desired genotype or trait. In aspects of this disclosure, heteroplasmy is shifted by utilizing a CRISPR-based recombinant expression system to alter the mtDNA to eliminate or reduce the frequency of mtDNA sequence variants in a cell, thereby increasing the ratio of normal versus mutant mtDNA.

A used herein, "cybrid" refers to a cytoplasmic hybrid cell or organism in which the mitochondrial genome is derived from a source distinct from the source(s) of the nuclear genome. For example, a cybrid embryo could contain nuclear DNA inherited from maternal and paternal oocytes, and mitochondrial DNA from a third parent that did not contribute any nuclear DNA.

As used herein, the term "CRISPR" refers to Clustered Regularly Interspaced Short Palindromic Repeats (CRISPR). CRISPR may also refer to a technique or system of sequence-specific genetic manipulation relying on the CRISPR pathway. A CRISPR recombinant expression system can be programmed to cleave a target polynucleotide using a CRISPR endonuclease and a guideRNA. A CRISPR system can be used to cause double stranded or single stranded breaks in a target polynucleotide. A CRISPR system can also be used to recruit proteins or label a target polynucleotide. In some aspects, CRISPR-mediated gene editing utilizes the pathways of nonhomologous end-joining (NHEJ) or homologous recombination to perform the edits. These applications of CRISPR technology are known and widely practiced in the art. See, e.g., U.S. Pat. No. 8,697,359 and Hsu et al. (2014) *Cell* 156(6): 1262-1278.

The term "Cas9" refers to a CRISPR-associated, RNA-guided endonucleoase such as *Streptococcus pyogenes* Cas9 (spCas9) and orthologs and biological equivalents thereof. Orthologs include but are not limited to *Staphylococcus aureus* Cas9 ("spCas9"), Cas 9 from *Streptococcus thermophiles, Legionella pneumophilia, Neisseria lactamica, Neisseria meningitides, Francisella novicida*; C2c1 from *Alicyclobacillus acideterrestris*, and Cpf1 (which performs cutting functions analogous to Cas9) from various bacterial species including *Acidaminococcus* spp. and *Francisella novicida* U112. Cas9 may refer to an endonuclease that causes double stranded breaks in DNA, a nickase variant such as a RuvC or HNH mutant that causes a single stranded break in DNA, as well as other variations such as deadCas-9 or dCas9, which lack endonuclease activity. Cas9 may also refer to "split-Cas9" in which CAs9 is split into two halves—C-Cas9 and N-Cas9—and fused with a two intein moieties. See, e.g., U.S. Pat. No. 9,074,199 B1; Zetsche et al. (2015) Nat Biotechnol. 33(2):139-42; Wright et al. (2015) PNAS 112(10) 2984-89.

A Cas9 endonuclease may be modified by the addition of nuclear localization signal domains (NLS) or, as in aspects of this disclosure, by the addition of one or more mitochondrial localization signal (MLS) domains. In some embodiments, the one or more MLS is comprised of Mouse Ornithine transcarbamylase (OTC) leader sequence (MLS1) or an equivalent thereof. In some embodiments, the MLS1 comprises about 140 contiguous base pairs. In other embodiments, the one or more MLS is comprised of Human Cytochrome c oxidase subunit 8A leader seq (Cox8A-MLS2). In some embodiments, Cox8A-MLS2 comprises about 74 contiguous base pairs. In other embodiments, the one or more MLS is comprised of Superoxide dismutase 2, mitochondrial leader seq (hSOD2-MLS). hSOD-MLS is comprised of about 73 contiguous base pairs. In some embodiments, one or more of these MLS sequences is appended to the coding region of the Cas9 gene. MLS sequences may be added to the 5' terminal end of the Cas9 gene, the 3' terminal end of the Cas9 gene, and/or within the coding region of the Cas9 gene. In some embodiments, recombinant Cas9 is modified by the fusion of MLS1 at the 5' terminal end of the Cas9 gene coding region. In some embodiments, Cas9 is modified by the fusion of Cox8A-MLS2 to the 3' terminal end of the coding region.

As used herein, the term "recombinant expression system" refers to a genetic construct for the expression of certain genetic material formed by recombination.

As is known to those of skill in the art, there are 6 classes of viruses. The DNA viruses constitute classes I and II. The RNA viruses and retroviruses make up the remaining classes. Class III viruses have a double-stranded RNA genome. Class IV viruses have a positive single-stranded RNA genome, the genome itself acting as mRNA Class V viruses have a negative single-stranded RNA genome used as a template for mRNA synthesis. Class VI viruses have a positive single-stranded RNA genome but with a DNA intermediate not only in replication but also in mRNA synthesis. Retroviruses carry their genetic information in the form of RNA; however, once the virus infects a cell, the RNA is reverse-transcribed into the DNA form which integrates into the genomic DNA of the infected cell. The integrated DNA form is called a provirus.

A "viral vector," also known as an "expression vector," is defined as a recombinantly produced virus or viral particle that comprises a polynucleotide to be delivered into a host cell, either in vivo, ex vivo or in vitro. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827.

In aspects where gene transfer is mediated by a lentiviral vector, a vector construct refers to the polynucleotide comprising the lentiviral genome or part thereof, and a therapeutic gene. As used herein, "lentiviral mediated gene transfer" or "lentiviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. Retroviruses carry their genetic information in the form of RNA; however, once the virus infects a cell, the RNA is reverse-transcribed into the DNA form which integrates into the genomic DNA of the infected cell. The integrated DNA form is called a provirus. As used herein, lentiviral vector refers to a viral particle capable of introducing exogenous nucleic acid into a cell through a viral or viral-like entry mechanism. A "lentiviral vector" is a type of retroviral vector well-known in the art that has certain advantages in transducing nondividing cells as compared to other retroviral vectors. See, Trono D. (2002) Lentiviral vectors, New York: Spring-Verlag Berlin Heidelberg.

Lentiviral vectors of this disclosure are based on or derived from oncoretroviruses (the sub-group of retroviruses containing MLV), and lentiviruses (the sub-group of retroviruses containing HIV). Examples include ASLV, SNV and RSV all of which have been split into packaging and vector components for lentiviral vector particle production systems. The lentiviral vector particle according to the disclosure may be based on a genetically or otherwise (e.g. by specific choice of packaging cell system) altered version of a particular retrovirus.

That the vector particle according to the disclosure is "based on" a particular retrovirus means that the vector is derived from that particular retrovirus. The genome of the vector particle comprises components from that retrovirus as a backbone. The vector particle contains essential vector components compatible with the RNA genome, including reverse transcription and integration systems. Usually these will include gag and pol proteins derived from the particular retrovirus. Thus, the majority of the structural components of the vector particle will normally be derived from that retrovirus, although they may have been altered genetically or otherwise so as to provide desired useful properties. However, certain structural components and in particular the env proteins, may originate from a different virus. The vector host range and cell types infected or transduced can be altered by using different env genes in the vector particle production system to give the vector particle a different specificity.

The term "adeno-associated virus" or "AAV" as used herein refers to a member of the class of viruses associated with this name and belonging to the genus dependoparvovirus, family Parvoviridae. Recombinant AAVs have been widely utilized for gene therapy due to their overall safety, mild immune response, long transgene expression, and high infection efficiency. Multiple serotypes of this virus are known to be suitable for gene delivery and can infect cells from various tissue types. Non-limiting exemplary serotypes useful in the methods disclosed herein include any of serotypes AAV1, AAV2, AAV3, AAV4, AAV5, AAV6, AAV7, AAV8, AAV9, AAV10, or AAV11. These serotypes differ in their tropism, or the types of cells they infect, making AAV a useful system for preferentially transducing specific cell types. For example, AAV2 is capable of infecting central nervous system (CNS) tissue, kidney tissue, photoreceptor cells, and retinal pigment epithelium. AAV9, in contrast, is capable of infecting CNS, heart, liver, lung, and skeletal muscle tissue. See, Moser R J. (2016) Curr Gene Ther 16(3):207-19.

Hybrid AAV vectors that have further refined the tropism of AAV through pseudotyping may also be used in aspects of this disclosure. These pseudotyped vectors are created by mixing the capsid of one serotype of AAV with the genome of another AAV. For example, AAV4/9 indicates a virus containing the genome of serotype AAV4 packaged in the capsid from serotype AAV9. Pseudotyped vectors may also be created by using hybrid capsids derived from multiple different serotypes such as AAV-DJ. Use of these pseudotyped vectors can improve transduction efficiency and alter tropism.

The term "scAAV" refers to a self-complementary AAV vector. scAAV vectors contain complementary sequences that are capable of spontaneously annealing upon infection, eliminating the virus' dependence upon its host cell for DNA synthesis.

Additional variants of AAV may be used in aspects of this disclosure. For example, to increase the packaging capacity of AAV, a longer transgene may be split across two AAV transfer plasmids containing either a 3' splice donor or a 5' splice acceptor. Co-infection with these two vectors results in concatemers, allowing the full-length transgene to be expressed. Another variant of AAV utilizes homologous recombination. In this variant, a gene is divided between two transfer plasmids, but with a substantial overlap in sequence. When cells are co-infected with the plasmids, homologous recombination occurs and allows for expression of the full-length transgene.

As used herein, "stem cell" defines a cell with the ability to divide for indefinite periods in culture and give rise to specialized cells. At this time and for convenience, stem cells are categorized as somatic (adult) or embryonic. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. An embryonic stem cell is one that has been cultured under in vitro conditions that allow proliferation without differentiation for months to years. A clone is a line of cells that is genetically identical to the originating cell; in this case, a stem cell.

"Double stranded RNA" (dsRNA) refer to double stranded RNA molecules that may be of any length and may be cleaved intracellularly into smaller RNA molecules, such as siRNA. Viral genomes may comprise dsRNA. In cells that have a competent interferon response, longer dsRNA, such as those longer than about 30 base pair in length, may trigger the interferon response. In other cells that do not have a competent interferon response, dsRNA may be used to trigger specific RNAi.

As used herein, an "RP loop" is a nucleotide fragment of an RNA stem-loop structure that facilitates RNA import into mammalian mitochondria via a polynucleotide phosphorylase (PNPASE). PNPASE is located in the mitochondrial intermembrane space and regulates the import of nuclear-encoded RNAs into the mitochondrial matrix. The RP loop sequence may be 20 nucleotides in length or range from 15-124 nucleotides in length. The RP loop sequence may comprise SEQ ID NO.: 2, or an equivalent thereof. A further description of an RP loop sequence can be found in Wang et al., (2010) Cell 142(3) 456-467.

In other embodiments, RP loop refers to a loop sequence derived from MRP RNA which facilitates RNA import into the mitochondria. MRP RNA has similar structure to the RP loop from RNase P RNA and it can also translocate non-mitochondrial RNA to mitochondria using the same PNPASE anchor in inner mitochondrial membrane of mitochondria. The MRP-loop may comprise SEQ ID NO.: 4, or an equivalent thereof. In other embodiments, the RP loop refers to a sequence derived from 5S RNA which facilitates RNA import into the mitochondria.

As used herein, "guide RNAs" (gRNAs) refer to a specific RNA moiety that recruits and directs the nuclease activity of Cas9. The gRNA is a short synthetic RNA composed of a "scaffold" sequence necessary for Cas9-binding and a user-defined ~20 nucleotide target polynucleotide sequence which defines the genomic target to be bound or altered. A user can change the genomic target of Cas9 by simply changing the target polynucleotide sequence of the gRNA. The scaffold sequence of a gRNA is comprised of a trans-activating crRNA (tracrRNA) sequence and a CRISPR RNA (crRNA) sequence. The crRNA and tracrRNA may be expressed as separate polynucleotides or fused together as a single construct.

Techniques of designing gRNAs and donor therapeutic polynucleotides for target specificity are well known in the art. For example, Doench, J., et al. Nature biotechnology 2014; 32(12):1262-7, Mohr, S. et al. (2016) FEBS Journal 283: 3232-38, and Graham, D., et al. Genome Biol. 2015; 16: 260. In some aspects, a gRNA is synthetic (Kelley, M. et al. (2016) J of Biotechnology 233 (2016) 74-83). As used herein, a biological equivalent of a gRNA includes but is not limited to a polynucleotide or targeting molecule that can guide a Cas9 or equivalent thereof to a specific nucleotide sequence such as a specific region of a mitchondrial genome.

As used herein, a "target polynucleotide sequence" on a guide RNA is a sequence approximately 20 nucleotides in length that is complementary or identical to the DNA sequence that is the desired target of the nuclease and/or binding activity of Cas9. Thus, the target polynucleotide sequence directs (or "targets") the Cas9 complex to a specific DNA sequence to be modified. In some aspects of this disclosure, a target polynucleotide sequence targets a sequence of mtDNA in need of editing. In other aspects of this disclosure, a target polynucleotide is targeted to mtDNA. In some embodiments, a target polynucleotide sequence is 20 nucleotides in length. In other embodiments, a target polynucleotide sequence is between 19-22 nucleotides in length. In other embodiments, the target polynucleotide sequence is directed the mtND4 gene. In other embodiments, the target polynucleotide sequence is directed to the mtND4 gene as in SEQ ID NO.: 7.

In many CRISPR expression systems, the target of a target polynucleotide sequence must be immediately upstream or adjacent to a Protospacer Adjacent Motif (PAM). PAM sequences are typically 3-5 nucleotides but may be between 6-8 nucleotides or longer. PAM sequences vary and can be specific to the variant or species of Cas9 endonuclease used. Non-limiting examples of PAM sequences include NGG, NGAN, NGNG, NGAG, and NGCG wherein the N may be any polynucleotide.

Tools to assist in selection of the target polynucleotide sequences are readily available to the public. For example, a computer-based gRNA design tool is available on the internet at chopchop.cbu.uib.no/. The methods and assumptions underlying the ChopChop Tool are described in Montague et al. Nucleic Acids Res. (2014) 42:W401-7.

As used herein, a "spacer" is a polynucleotide sequence between 6 to 8 nucleotides in length and located between the RP loop and the target polynucleotide sequence on the gRNA. In some embodiments, the spacer is encoded by SEQ ID NO.: 5 or an equivalent thereof. In other embodiments, the spacer may be 3 to 5 or 9 to 20 nucleotides in length. In other embodiments, the spacer may be a restriction endonuclease recognition site. Non-limiting examples of restriction endonuclease recognition sites include Pac1, EcoR1, BamH1, Apo1, BglII, Cla1, Dra1, EcoRV, Fse1, HindIII, and Hpa1. In some embodiments, the spacer is 0 nucleotides.

As used herein, a "donor polynucleotide" is a polynucleotide sequence encoding a desired sequence alteration. The donor polynucleotide may serve as a repair template or be incorporated into the targeted polynucleotide region by HR or NHEJ. During gene editing, the target polynucleotide sequence is altered to be identical to the donor polynucleotide. In some embodiments, a donor polynucleotide is encoded on the same expression vector as the gRNA and/or Cas9. In other embodiments, the donor polynucleotide is located on a different expression vector from the gRNA and/or Cas9.

The term "an expression control element" as used herein, intends a polynucleotide that is operatively linked to a target polynucleotide to be transcribed, and facilitates the expression of the target polynucleotide. A promoter is an example of an expression control element.

A promoter is a regulatory polynucleotide, usually located 5' or upstream of a gene or other polynucleotide, that provides a control point for regulated gene transcription. RNA polymerase II and III are examples of polymerase enzymes that bind to promoters and catalyze transcription.

An RNA polymerase II-specific promoter serves as a binding site for RNA polymerase II (pol II), which catalyzes the transcription of DNA to synthesize precursors of mRNA, and most shRNA and microRNA. Examples of pol II promoters are known in the art and include without limitation, the phosphoglycerate kinase ("PGK") promoter; EF1-alpha; CMV (minimal cytomegalovirus promoter); delta CMV; CBA (chicken β-actin); CBh; and LTRs from retroviral and lentiviral vectors.

An RNA polymerase III or "pol III"-specific promoter is a polynucleotide found in eukaryotic cells that serves as a binding site for pol III to transcribe DNA to synthesize ribosomal 5S rRNA, tRNA and other small RNAs. Examples of pol III promoters include without limitation a U6 promoter, an H1 promoter, or an MNDU3 promoter.

A "polyadenylation signal" is a polynucleotide sequence comprising multiple adenine nucleotides located on the 3' terminal end of an RNA transcript to promote stability of the transcript and facilitiate translation. A non-limiting example of a polyadenylation signal is the Bovine Growth Hormone Polyadenylation Signal (BGHpA).

A "target cell" as used herein, shall intend a cell containing the genome into which polynucleotides that are operatively linked to an expression control element are to be integrated. Cells that are infected with AAV or susceptible to AAV infection are examples of target cells.

As used herein, the term "reporter marker" intends a polynucleotide, detectable label or other molecule that allows for the identification of a preselected composition. Non-limiting examples of reporter markers include, without limitation CD25, a hemmaglutinin tag, an enhanced green fluorescent protein (EGFP), a red flouresence protein (RFP), a green fluorescent protein (GFP) and yellow fluorescent protein (YFP) or the like. These are commercially available and described in the technical art.

As used herein, a "selectable marker" refers to a gene, genetic mutation, or polynucleotide that confers a trait for survival or artificial selection upon a cell. Non-limiting examples of selectable markers include antibiotic resistance genes (e.g. ampicillin resistance gene), genes that can complement auxotrophy, and genes that can confer resistance to protein synthesis inhibitors (e.g. puromycin resistance gene). These are commercially available and described in the technical art.

A "composition" is intended to mean a combination of active polypeptide, polynucleotide or antibody and another compound or composition, inert (e.g. a detectable label) or active (e.g. a gene delivery vehicle).

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

A "subject," "individual" or "patient" is used interchangeably herein, and refers to a vertebrate, preferably a mammal, more preferably a human. Mammals include, but are not limited to, murines, rats, rabbit, simians, bovines, ovine, porcine, canines, feline, farm animals, sport animals, pets, equine, and primate, particularly human. Besides being useful for human treatment, the present disclosure is also useful for veterinary treatment of companion mammals, exotic animals and domesticated animals, including mammals, rodents, and the like which is susceptible to mitochondrial conditions. In one embodiment, the mammals include horses, dogs, and cats. In another embodiment of the present disclosure, the human is an adolescent or infant under the age of eighteen years of age.

"Host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

An "enriched population" of cells intends a substantially homogenous population of cells having certain defined characteristics. The cells are greater than 70%, or alternatively greater than 75%, or alternatively greater than 80%, or alternatively greater than 85%, or alternatively greater than 90%, or alternatively greater than 95%, or alternatively greater than 98% identical in the defined characteristics.

The terms "disease," "disorder," and "condition" are used inclusively and refer to any condition mediated at least in part by defective mitochondria or mutations in mitochondrial genes.

"Treating" or "treatment" of a disease includes: (1) preventing the disease, i.e., causing the clinical symptoms of the disease not to develop in a patient that may be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The term "suffering" as it related to the term "treatment" refers to a patient or individual who has been diagnosed with or is predisposed to infection or a disease incident to infection. A patient may also be referred to being "at risk of suffering" from a disease because of active or latent infection. This patient has not yet developed characteristic disease pathology.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present disclosure for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks. Consistent with this definition, as used herein, the term "therapeutically effective amount" is an amount sufficient to inhibit RNA virus replication ex vivo, in vitro or in vivo.

The term administration shall include without limitation, administration by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The disclosure is not limited by the route of administration, the formulation or dosing schedule.

Descriptive Embodiments

In another aspect, provided herein is a hybrid guide RNA comprising an RP loop sequence, a spacer, a target polynucleotide sequence, a crRNA sequence, and a tracrRNA sequence and polynucleotides encoding the hybrid guide RNA. In one aspect, the hybrid guide RNA further comprises a detectable and/or a selection marker. The hybrid guide RNA can be used for assaying therapeutic targets and/or for insertion into the CRISPR system as described herein.

In a further aspect, polynucleotides (e.g., DNA) encoding the hybrid guide RNA are provided. In one aspect, the encoding polynucleotide further comprises a detectable and/ or a selection marker. The elements of the polynucleotide encoding the hybrid guide RNA can be operatively linked to expression elements necessary for expression of the polynucleotide to the hybrid guide RNA, e.g., a promoter, e.g., a pol I and/or a pol II promoter as necessary, e.g., a U6, CMV or CBh promoter. The polynucleotide (e.g., a DNA polynucleotide) can be contained within an appropriate expression or replication vector and/or a host cell. Non-limiting examples of vectors include adenoviral vectors, lentiviral vectors and AAV vectors, examples of such are provided herein. Non-limited examples of host cells include mammalian cells, e.g., human cells, canine cells, murine cells, feline cells and equine cells. The cells and vectors containing the encoding polynucleotide can be used for recombinant expression or replication of the encoding polynucleotide.

This disclosed hybrid guide RNAs can contain various RP loop sequences, non-limiting examples of such include polynucleotides comprising at least 15, or alternatively at least 18, or alternatively at least 20, or alternatively about 20 contiguous nucleotides. In one aspect, the RP loop sequence is located on the 5'-terminus of the hybrid guide RNA sequence and non-limiting examples of RP loop sequences comprise one or more of the nucleotide sequence of SEQ ID NO.: 2, or an equivalent thereof; the nucleotide sequence of SEQ ID NO.: 1, or an equivalent thereof; the nucleotide sequence of SEQ ID NO.: 3, or an equivalent thereof; and the nucleotide sequence of SEQ ID NO.: 4, or an equivalent thereof.

In one aspect, the spacer of the hybrid guide RNA comprises at least 5 nucleotides. A non-limiting example includes a polynucleotide comprising the nucleotide sequence of SEQ ID NO.: 5, or an equivalent thereof.

In another aspect, the target polynucleotide sequence is targeted to a polynucleotide located inside a mitochondrion. Alternatively, the target polynucleotide sequence is targeted to a mitochondrial gene sequence in need of editing. The target polynucleotide sequence can be of any appropriate length, e.g., comprising at least about 15 nucleotides. In one embodiment, the target polynucleotide sequence is targeted to the mtND4 gene.

In a particular aspect, the hybrid guide RNA, the hybrid guide RNA is encoded by the nucleotide sequence of SEQ ID NO.: 6, or an equivalent of SEQ ID NO.: 6 or SEQ ID NO: 7, or an equivalent thereof.

This disclosure also provides a recombinant expression system for CRISPR-based mitochondrial gene editing comprising, or alternatively consisting essentially of, or yet further consisting of: one or more expression vectors; a polynucleotide encoding a recombinant Cas9 endonuclease; and a polynucleotide encoding a hybrid guide RNA as described above.

In one aspect, the expression vector is one of a lentiviral vector, an adenoviral vector, or a recombinant adeno-associated viral vector (AAV). Non-limiting examples of recombinant AAV vectors include, for example, AAV1, AAV2, AAV3, AAV4, AAV5, AAV6, AAV7, AAV8, AAV9, AAV10, or AAV11. Alternatively, the recombinant AAV vector is a hybrid vector combining the capsid of any one of serotypes AAV1, AAV2, AAV3, AAV4, AAV5, AAV6, AAV7, AAV8, AAV9, AAV10, or AAV11 with the viral genome of any other of serotypes AAV1, AAV2, AAV3, AAV4, AAV5, AAV6, AAV7, AAV8, AAV9, AAV10, or AAV11.

In a further aspect, the recombinant AAV vector is a self-complementary vector. Non-limiting examples of such include scAAV2 and scAAV9.

In one aspect, provided herein is an alternative to the viral delivery system for Cas9 using lipid nanoparticle-mediated delivery. This recombinant expression system for CRISPR-based mitochondrial gene editing comprises, consists of, or consists essentially of a polynucleotide encoding a recombinant Cas9 endonuclease; C12-200; and optionally one or more expression vectors; and a polynucleotide encoding a hybrid guide RNA.

In some embodiments, C12-200, a lipid-like material, is complexed with the polynucleotide encoding the Cas9. C12-200 can be synthesized as previously described in Hossain N et al. Nat Biotechnol (2008) 26: 561-69. Lipid-Cas9 nanoparticles are prepared as described in Yin et al. (2016) Nat Biotechnol.; 34(3): 328-33. In addition to making complexes of liposome:endonuclease (Cas9, Cpf1, or C2c1) mRNA, a linear rAAV Cas9 plasmid may be used for complex with liposome. In some embodiments, an sgRNA and optionally a repair template can be delivered by AAV vector with the liposomes.

In one embodiment, the expression vector further comprises one or more selectable or detectable markers.

In some embodiments, the recombinant Cas9 is spCas9, saCas9, C2c1, or Cpf1. In particular embodiment, the recombinant Cas9 polynucleotide encodes a nickase. In a yet further aspect, the Cas9 polynucleotide further comprises one or more mitochondrial localization signals (MLS), nonlimiting examples of such include one or more MLS is selected from the group of MLS1, Cox8A-MLS2, or hSOD2-MLS. In a further aspect, the recombinant Cas9 polynucleotide is codon-optimized for expression in a subject.

In a yet further aspect, the recombinant expression system as described herein further comprises a donor polynucleotide that encodes an edited version of a mitochondrial polynucleotide sequence in need of editing.

In one aspect, the recombinant Cas9 endonuclease and the hybrid guide RNA are encoded by one or different expression vectors.

In one aspect, the expression vector comprises all or part of the nucleotide sequence of SEQ ID NO.: 8, or an equivalent thereof, or the expression vector comprises all or part of the nucleotide sequence of SEQ ID NO.: 9, or an equivalent thereof, or the expression vector comprises all or part the nucleotide sequence SEQ ID NO.: 32, or an equivalent thereof, or the expression vector comprises all or part of the nucleotide sequence SEQ ID NO.: 33, or an equivalent thereof, or the expression vector comprises all or part of the nucleotide sequence SEQ ID NO.: 34, or an equivalent thereof.

Further provided by this disclosure is a viral packaging system comprising the recombinant system as described herein and a packaging cell line. Packaging cell lines are know in the art. The systems are useful to produce a viral particle comprising the recombinant system as described herein.

In a further aspect, the viral particles produced by this system are provided herein, as well as a plurality of particles. The plurality of particles may contain the same or different recombinant expression systems.

Further provided is a composition comprising a single or a plurality of particles of this disclosure and a carrier, e.g., a pharmaceutically acceptable carrier.

The systems and particles are useful in a number of methods. For example, a method for shifting mitochondrial heteroplasmy in a cell is provided, the method, comprising administering an effective amount of the recombinant expression system as described herein or an effective amount of the viral particle as described herein, to the cell, thereby shifting mitochondrial hetroplasmy in the cell. In a further aspect, the method further comprises assaying for the expression of mtND4.

The cells can be a mammalian cell, e.g., a human cell, a murine cell, a canine cell, an equine cell, or a feline cell, and of any appriate phenotype. Non-limiting examples include, a stem cell and a germline competent murine embryonic stem cell.

In another aspect, a method is provided for CRISPR-based mitochondrial gene editing in a subject, comprising administering an effective amount of the viral particle as described herein to the subject, thereby editing a mitochondrial gene in the subject. Yet further provided is a method of treating a mitochondrial condition in a subject is provided, the method comprising administering an effective of the recombinant expression system as described herein or an effective amount of the viral particle as described herein, thereby treating the mitochondrial condition in the subject. Non-limiting mitochondrial conditions include without limitation, are selected from Pearson Syndrome, Kearns-Sayre Syndrome, progressive external opthalmoplegia, mitochondrial myopathy, encephalopathy, lactic acidosis, stroke-like syndrome (MELAS), myoclonic epilepsy with ragged-red fibers (MERFF), or Leigh Syndrome. In a particular aspect, the mitochondrial condition is Leber hereditary optic neuropathy (LHON).

For the methods disclosed herein, the subject is a mammal, e.g., a human, a canine, a feline, a bovine, an equine or a murine.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present disclosure is illustrated by the following examples. It is to be understood that the particular examples, materials, amounts, and procedures are to be interpreted broadly in accordance with the scope and spirit of the disclosure as set forth herein.

EXAMPLE 1

Figure 2:
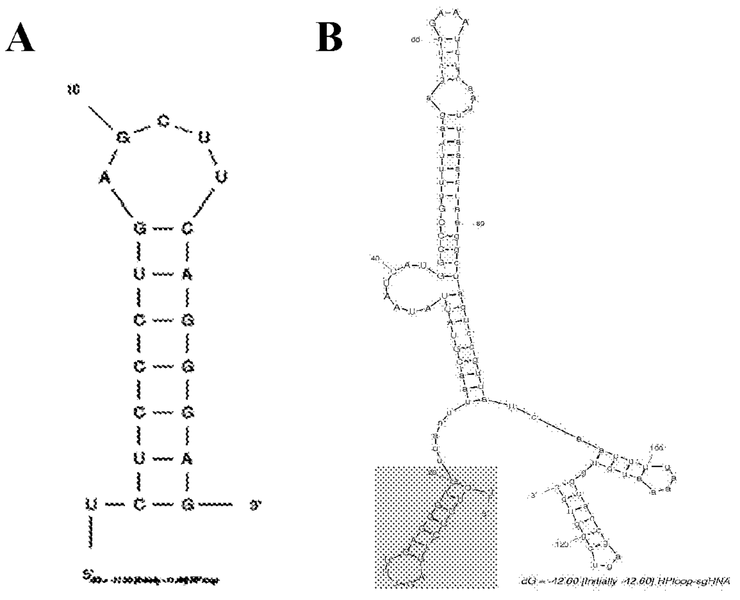
FIGS. 2A-2B. Diagrams depicting RP loop sequence and hybrid gRNA.

Gene editing is a rapidly progressing field and the ability to correct gene mutations in mitochondrial DNA in situ is highly desirable. The present disclosure relates to a system of gene editing in mitochondria comprising treatment of a cell with a hybrid guideRNA targeting mtDNA and fused to a RP-loop (FIG. 2A), and a recombinant Cas9 nuclease comprising mitochondrial localization signals (FIG. 1).

The RP Loop-gRNA Fusion

Figure 5:
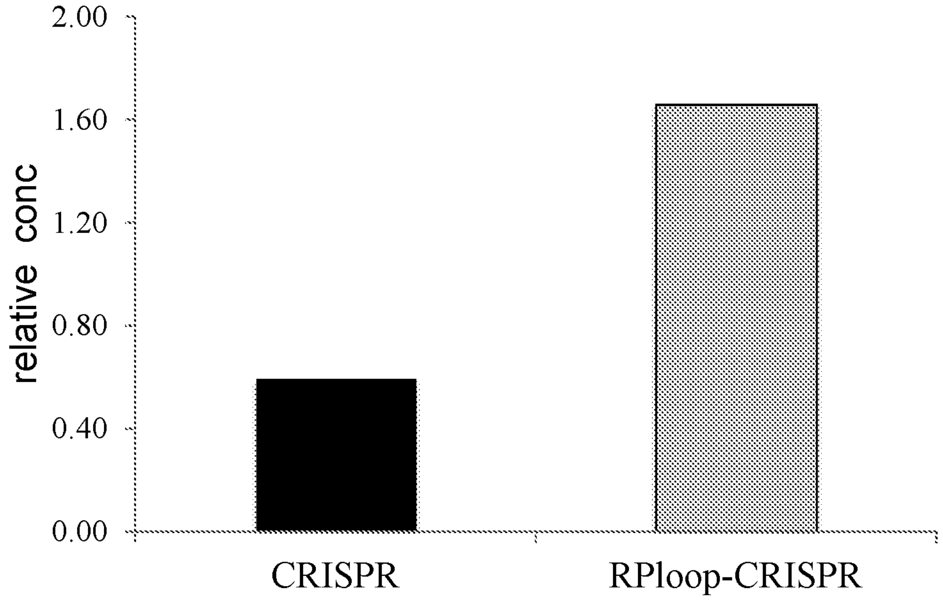
FIG. 5. CRISPR-guideRNA level in mitochondrial fraction with or without RP loop. The relative concentration of CRISPR-gRNA was examined in the mitochondrial fraction of cells expressing either a hybrid gRNA with an RP loop or a gRNA lacking an RP loop. The hybrid gRNA displayed greater expression in the mitochondrial fraction than the non-hybrid gRNA.
Figure 6:
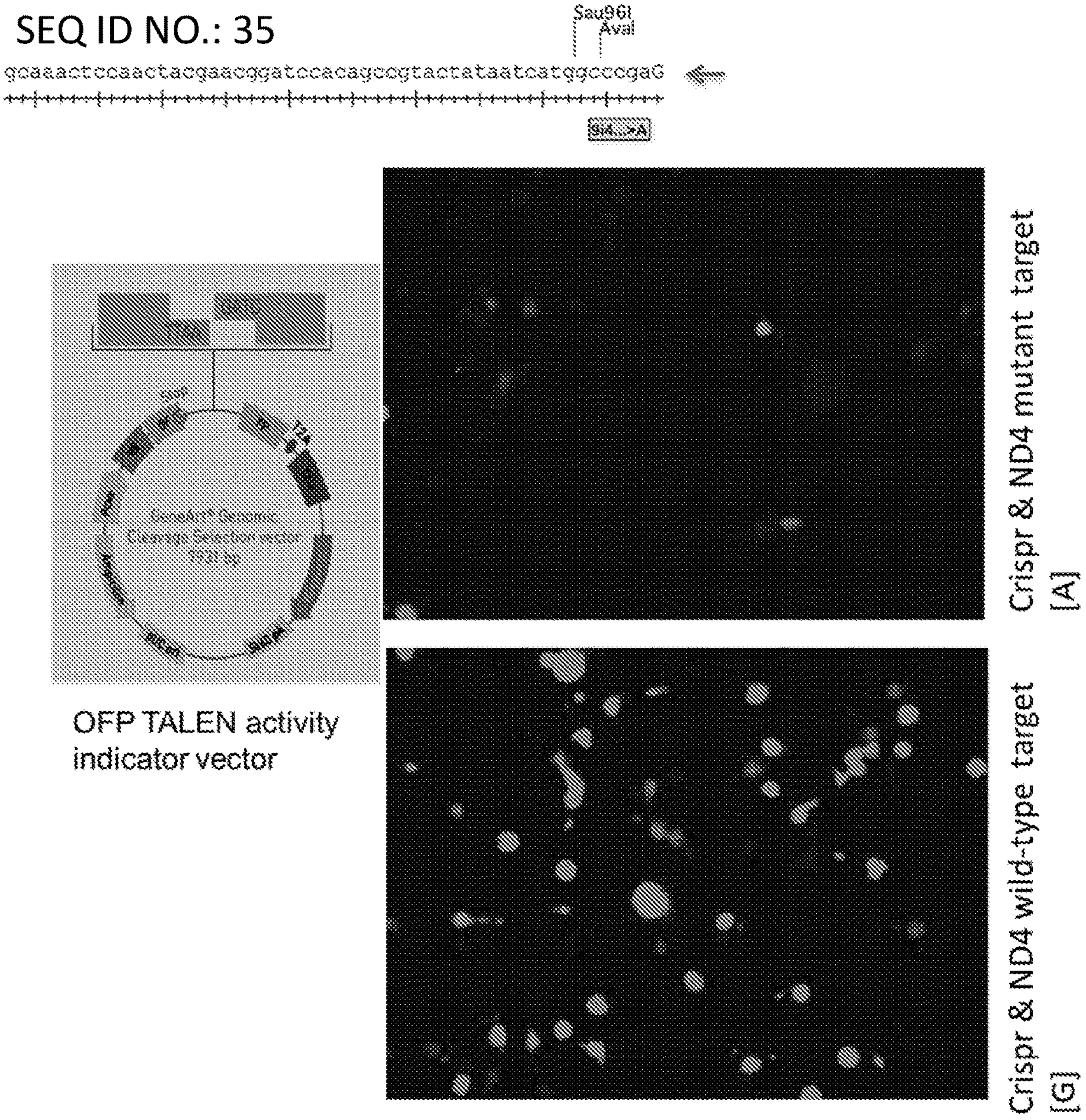
FIG. 6. In vitro assay to test ND4 mito-CRISPR functionality and specificity. SEQ ID NO.: 35 is disclosed with restriction sites noted.

A significant barrier to using a CRISPR gene editing system to edit mtDNA is enabling the gRNA to reach the inside of the mitochondria. A study by Wang et al. (2010 Cell 142(3): 456-457) disclosed that import of RNAs to the mitochondria could be augmented by appending an RP loop fragment from RNase P. In one aspect of the present disclosure, an RP loop was fused to the 5' terminal end of a CRISPR gRNA. This fusion resulted in import of the hybrid gRNA to the mitochondria (FIG. 5). Additional fusion products combining sequences from a 5S rRNA or an MRP RNA can also be used to import a gRNA to the mitochondria.

In aspects of this invention, the hybrid gRNA may be co-expressed with Cas9 on one or more expression vectors, or it may be synthesized in vitro and administered directly to cells as a functional RNA construct. Methods of in vitro synthesis include, without limitation, in vitro transcription. Manipulation of cybrid cell lines in vitro may require the use of in vitro synthesized form of the gRNA.

The MLS-Cas9 Peptide

Figure 4:
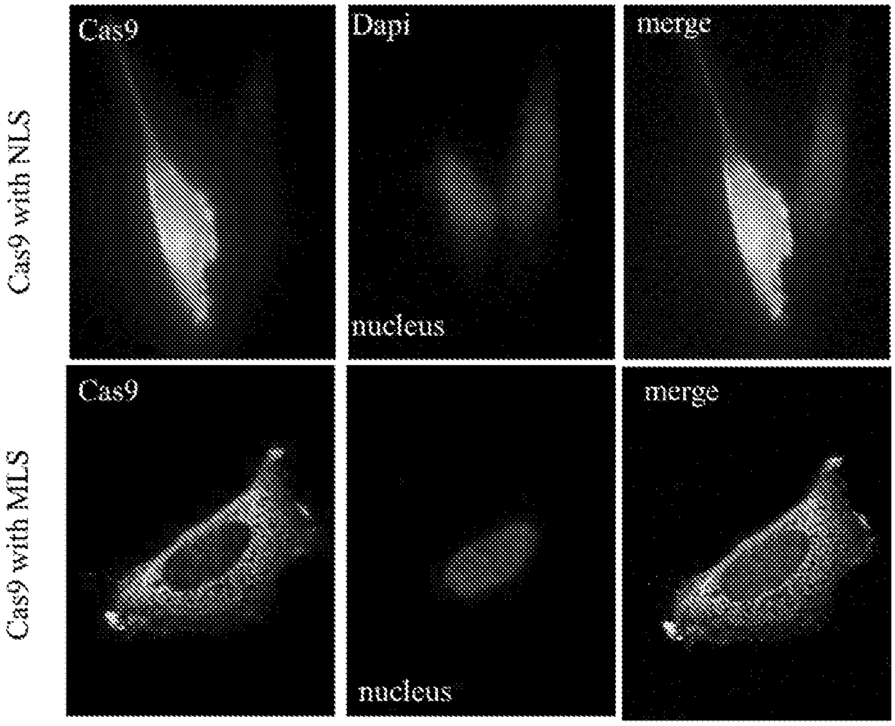
FIG. 4. Localization of Cas9 with Nuclear and mitochondrial localization signals. Nucleus stained with DAPI. Cells expressing NLS-Cas9 display expression in the nucleus and cytoplasm (top panels). Cells expressing MLS-Cas9 display non-nuclear expression.

Another significant barrier to the effective use of CRISPR to edit mtDNA is the localization of the Cas9 nuclease. In the present disclosure, the Cas9 nuclease has been modified to contain one or more MLS domains to facilitate transport to the mitochondria. In some embodiments, MLS are comprised of Mouse Ornithine transcarbamylase (OTC) leader sequence (MLS1) or an equivalent thereof. In some embodiments, the MLS1 comprises about 140 contiguous base pairs. In other embodiments, the one or more MLS is comprised of Human Cytochrome c oxidase subunit 8A leader seq (Cox8A-MLS2). In some embodiments, Cox8A-MLS2 comprises about 74 contiguous base pairs. In other embodiments, the one or more MLS is comprised of Superoxide dismutase 2, mitochondrial leader seq (hSOD2-MLS).

hSOD-MLS is comprised of about 73 contiguous base pairs. In some embodiments, one or more of these MLS sequences is appended to the coding region of the Cas9 gene. MLS sequences may be added to the 5' terminal end of the Cas9 gene, the 3' terminal end of the Cas9 gene, and/or within the coding region of the Cas9 gene. In some embodiments, recombinant Cas9 is modified by the fusion of MLS1 at the 5' terminal end of the Cas9 gene coding region. In some embodiments, Cas9 is modified by the fusion of Cox8A-MLS2 to the 3' terminal end of the coding region. Introduction of MLS to Cas9 resulted in an expression pattern consistent with localization to the mitochondria (FIG. 4). See Jo et al. (2015) BioMed Research International. 2015: 305716.

Creation of Cybrids to Study Heteroplasmy

To create cybrids, protoplasts from mitomycin inactivated fibroblasts, homoplastic for mtDNA mutants, can fused with germ line competent female mouse embryonic stem cells (ESCs) resulting in the creation of heteroplasmic mouse ESCs. A germline competent female ESC cell line is capable of passing on its genetic material to progeny. These ESCs containing a heteroplasmic mitochondrial population, can be used as a tool to develop mouse strains carrying heteroplasmic mitochondria in their tissues. The female ES cell line contains a pluripotency marker Oct4-GFP. Expression of this marker is used to determine whether the ES cell has maintained pluripotency subsequent to manipulation of the cytoplasm including the incorporation of cytoplasm from other cells. Germ line competency in female ES cells is much lower than normal XY ES cells and the cell line used herein required validation of pluripotency (tested by ability to contribute to the female germ line).

The tools described in this application may be used to alter or finesse the heteroplasmy ratio in a cybrid cell. Altering heteroplasmy is a strategy to study and/or treat mitochondrial conditions in patients with both mutated mtDNA and wild-type mtDNA. See Reddy et al. (2015) Cell. 161(3):459-469. “To bias heteroplasmy” means to treat heteroplasmic cells with the disclosed mito-CRISPR/Cas9 disclosure to edit mtDNA and thus alter the ratio of wild type to mutant mtDNA within a cell or population. Use of this tool can cause selective deletion of either mutant or wild-type mitochondria depending upon the type of target polynucleotide sequence selected in the hybrid gRNA. Disease phenotype variants should become more visible with heteroplasmy shifts as little as 10% where a threshold is required for a phenotype to manifest. Such shifts may require combining germ line breeding which would produce individual animals with different levels of heteroplasmy.

Gene Editing to Alter mtDNA and Gene Therapy

The tools described in this application may be used to edit mtDNA. In some embodiments, co-expression of a hybrid gRNA and an MLS-Cas9 can target the CRISPR complex to the mitochondria where it can access the mtDNA. Non-limiting examples of applications for this technology include causing mutations in mtDNA that disrupt mitochondrial genes, introducing wild type copies of mitochondrial genes, repairing point mutations in mtDNA, repairing deletions in mtDNA, removing deleterious insertions in mtDNA, introducing markers to mtDNA, reducing or increasing expression of mitochondrial genes, and introducing control constructs such as inducible expression systems that allow for control of mitochondrial gene expression.

The disclosure is useful to create viral particles capable of editing mtDNA in a subject exhibiting a mitochondrial condition. Clinical manifestations of defective mitochondria include disorders such as Pearson and Kearns-Sayre Syndromes, progressive external ophthalmoplegia, mitochondrial myopathy, encephalopathy, lactic acidosis, stroke-like syndrome (MELAS), myoclonic epilepsy with ragged-red fibers (MERFF), Leigh Syndrome, and Leber hereditary optic neuropathy (LHON). Subjects suffering from a mitochondrial condition may be treated by the administration of viral particles capable of editing the mtDNA in a specific tissue or in all cells of the body. In some embodiments of this disclosure, AAV viral particles encoding MLS-Cas9 and a hybrid gRNA targeted to a defective mitochondrial gene may be administered to a subject to correct the defective mtDNA. In some embodiments, the viral particles are administered to stem cells derived from the subject. In other embodiments, the viral particles have tropism for specific tissues within the subject such as liver or neural tissues and are directed to repair those tissues.

In another aspect, the disclosure is useful to alter heteroplasmy to increase the ratio of wild-type mitochondria within germline cells. In another aspect, the disclosure is useful to repair mtDNA within germline cells. Germline cells are capable of stably passing on their wild-type and/or repaired mitochondria to successive progeny.

Non-limiting, exemplary correction of Pearson Syndrome and/or Kearns-Sayre Syndrome with the methods disclosed herein involves restoring deleted mitochondrial DNA associated with the syndrome (e.g. deletion of 4977 bp spanning from position 8469 to position 13147 on the mt-genome (m.8470_13446del4977)) in subject, cell, mitochondrion, or tissue. Restoration may be achieved by targeting an sgRNA to the deletion locus and providing a donor polynucleotide encoding all or part of the deleted region to serve as a repair template. Alternatively, correction may be achieved by introducing DNA damage or other lethal mutation to mitochondria comprising the syndrome-associated deletion, thereby bias heteroplasmy toward normal mitochondria.

Non-limiting, exemplary correction of progressive external ophthalmoplegia with the methods disclosed herein involves repair of one or more of the following mutations associated with the condition in subject, cell, mitochondrion, or tissue: repair of a mutation of mitochondrial tRNA at nucleotide 3243 in which there is an A to G nucleotide transition, repair of a 4,977 base pair segment found between a 13 base pair repeat, and repair of mitochondrial DNA deletions. Alternatively, correction may be achieved by introducing DNA damage or other lethal mutation to mitochondria comprising the condition-associated mutation, thereby shifting heteroplasmy toward normal mitochondria.

Non-limiting, exemplary correction of Mitochondrial encephalomyopathy, lactic acidosis, and stroke-like episodes (MELAS) with the methods disclosed herein involves repair of mutations in one or more of the following genes in subject, cell, mitochondrion, or tissue: NADH-ubiquinone oxidoreductase chain 1 (MT-ND1, Entrez gene: 4535) or NADH-ubiquinone oxidoreductase chain 5 (MT-ND5, Entrez gene: 4540) (both related to NADH dehydrogenase); Mitochondrially encoded tRNA histidine (MT-TH, Entrez gene: 4564), Mitochondrially encoded tRNA leucine 1 (UUA/G) (MT-TL-1, Entrez gene: 4567), or Mitochondrially encoded tRNA valine (MT-TV, Entrez gene: 4577) (encoding specific mitochondrial transfer RNAs). Alternatively, correction may be achieved by introducing DNA damage or other lethal mutation to mitochondria comprising the condition-associated mutation, thereby shifting heteroplasmy toward normal mitochondria.

Non-limiting, exemplary correction of Leigh disease with the methods disclosed herein involves repair of mutations in one or more of the following genes in subject, cell, mitochondrion, or tissue: Mitochondrially encoded NADH dehydrogenase 2 (MT-ND2, Entrez gene: 4536), Mitochondrially encoded NADH dehydrogenase 3 (MT-ND3, Entrez gene: 4537), NADH-ubiquinone oxidoreductase chain 5 (MT-ND5, Entrez gene: 4540), NADH-ubiquinone oxidoreductase chain 6 (MT-ND6, Entrez gene: 4541), or ATP synthase Fo subunit 6 (MT-ATP6, Entrez gene: 4508). MT-ATP-6 is a gene that codes for a protein in the last complex of the oxidative phosphorylation chain, ATP synthase, an enzyme that directly generates ATP. The most common MT-ATP6 mutation found with Leigh syndrome is a point mutation at nucleotide 8993 that changes a thymine to a guanine. Alternatively, correction may be achieved by introducing DNA damage or other lethal mutation to mitochondria comprising the condition-associated mutation, thereby shifting heteroplasmy toward normal mitochondria.

Non-limiting, exemplary correction of Leber hereditary optic neuropathy with the methods disclosed herein involves repair of mutations in one or more of the following genes in subject, cell, mitochondrion, or tissue: MT-ND1, NADH-ubiquinone oxidoreductase chain 4 (MT-ND4, Entrez gene: 4538), NADH-ubiquinone oxidoreductase chain 4L (MT-ND4L Entrez gene: 4539), and MT-ND6. Alternatively, correction may be achieved by introducing DNA damage or other lethal mutation to mitochondria comprising the condition-associated mutation, thereby shifting heteroplasmy toward normal mitochondria.

In some cases, gene therapy or gene editing of mitochondrial DNA can be accompanied by gene therapy or gene editing of nuclear DNA with a CRISPR system targeted to the nucleus. Non-limiting examples of nuclear genes that may be repaired include genes associated with mitochondrial disorders such as Twinkle protein (PEO1, Entrez gene: 56652; NM_001163812), Antenna (ANT1, Entrez gene: 291; NM_001151), DNA polymerase subunit gamma (POLG, Entrez gene: 5428; NM_002693), Dynamin-like 120 kDa protein, mitochondrial (OPA1, Entrez gene: 4976; NM_015560), Surfeit locus protein 1 (SURF1, Entrez gene: 6834; NM_001280787), Mitochondrial chaperone BCS1 (BCS1L, Entrez gene: 617, NM_001079866), NADH dehydrogenase [ubiquinone] 1 alpha subcomplex subunit 10 (NDUFA10, Entrez gene: 4705, NM_004544), Succinate dehydrogenase complex, subunit A, flavoprotein variant (SDHA, Entrez gene: 6389, NM_001294332), NADH dehydrogenase [ubiquinone] iron-sulfur protein 4, mitochondrial (NDUFS4, Entrez gene: 4724, NM_002495), NADH:Ubiquinone Oxidoreductase Complex Assembly Factor 2 (NDUFAF2, Entrez gene: 91942), NADH dehydrogenase [ubiquinone] 1 alpha subcomplex subunit 2 (NDUFA2, Entrez gene: 4695, NM_001185012), NADH:Ubiquinone Oxidoreductase Complex Assembly Factor 6 (NDUFAF6, Entrez gene: 137682), Cytochrome C Oxidase Assembly Homolog (COX15, Entrez gene: 1355, NM_004376), NADH dehydrogenase [ubiquinone] iron-sulfur protein 3, mitochondrial (NDUFS3, Entrez gene: 4722, NM_004551), NADH dehydrogenase [ubiquinone] iron-sulfur protein 8, mitochondrial (NDUFS8, Entrez gene: 4728, NM_002496), FAD-dependent oxidoreductase domain-containing protein 1 (FOXRED1, Entrez gene: 55572, NM_017547), NADH dehydrogenase [ubiquinone] 1 alpha subcomplex subunit 9 (NDUFA9, Entrez gene: 4704, NM_005002), NADH dehydrogenase [ubiquinone] 1 alpha subcomplex subunit 12 (NDUFA12, Entrez gene: 55967, NM_018838), NADH dehydrogenase [ubiquinone] iron-sulfur protein 7, mitochondrial (NDUFS7, Entrez gene: 374291, NM_024407), and DNA polymerase subunit gamma-2, mitochondrial (POLG2, Entrez gene: 11232; NM_007215).

Materials and Methods

Template Mito-CRISPR/Cas9 Expression Construct

The expression vector pX-U6-RP-sgRNA-MLS-mSpCas9 (SEQ ID NO.: 8) was designed to edit mitochondrial DNA (FIG. 1). This expression vector contains both an MLS-tagged Cas9 and the hybrid RP loop guideRNA (gRNA) (SEQ ID NO.: 6). The hybrid guide RNA polynucleotide comprises the RP stem loop (SEQ ID NO.: 1), a Pac1 spacer (SEQ ID NO.: 5), a 19-20 bp target region to be tailored to the specific target region (depicted as N's in SEQ ID NO.: 6), and the tracrRNA/crRNA scaffold region. The hybrid gRNA is under the control of a U6 promoter. Downstream of the gRNA is a CBh promoter to regulate expression of the Cas9 polynucleotide. A mouse-optimized *Streptococcus pyogenes* Cas9 (mSpCas9) polynucleotide is flanked by a mitochondrial localization signal (MLS) on either side. Downstream of the Cas9 polynucleotide is a bGHpA sequence encoding a polyadenylation signal. The expression vector also encodes an ampicillin resistance gene ($Amp^r$) and an origin of replication (pUC ori).

Template Mito-CRISPR/Cas9 Expression scAAV Construct

The expression vector scAAV-U6-RP-sgRNA-deltaCMV-eGFP (SEQ ID NO.:9) was designed to edit mitochondrial DNA. This expression vector contains an scAAV backbone, a U6 promoter driving expression of the RP loop hybrid gRNA, a deltaCMV promoter, and eGFP as a marker.

MLS-Cas9 is Transported to the Mitochondria

Figure 3:
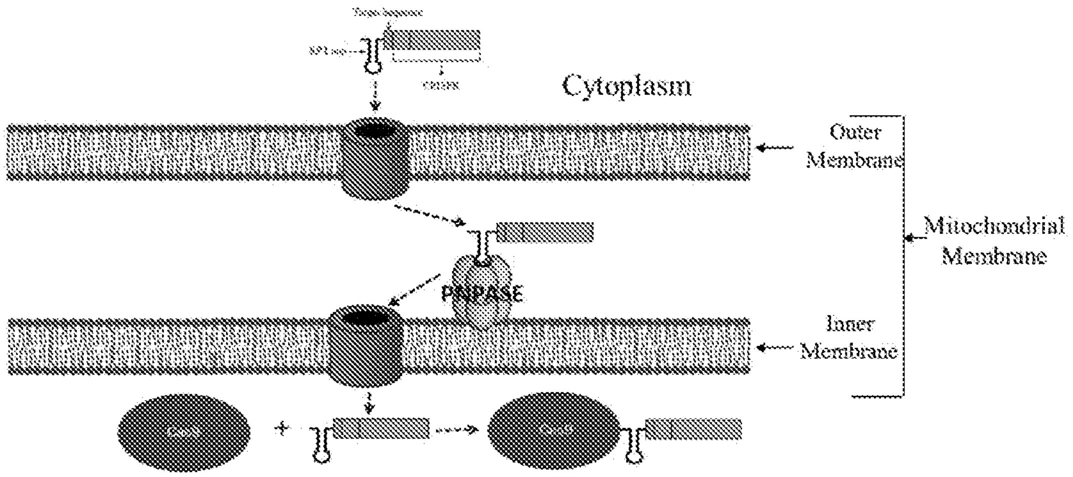
FIG. 3. Transport of hybrid guide RNA into the mitochondria. This diagram depicts the mechanism through which the hybrid guide RNA is imported into the mitochondria. The hybrid guide RNA with the RP Loop is brought through the mitochondrial pores by PNPASE. In this embodiment, Cas9 is independently imported to the mitochondria via transport mechanisms involving its mitochondrial localization signals.

When the pX-U6-RP-sgRNA-MLS-mSpCas9 expression vector is expressed in a cell, the hybrid gRNA is transported into the mitochondria (FIG. 3). The RP loop is brought through the mitochondrial pores by PNPASE where it interacts with mSpCas9. mSpCas9 is imported into the mitochondria via transport mechanisms utilizing its MLS. Unlike Cas9 with NLS domains, Cas9 with MLS domains is not imported to the nucleus. In in vitro fluorescence experiments, cells transfected with NLS-Cas9 exhibit Cas9 localization in the nucleus (FIG. 4). The nucleus can be identified by staining with DAPI. Cells transfected with MLS-Cas9 display non-nuclear expression, consistent with their transport to the mitochondria.

RP Loop Hybrid gRNA is Transported to the Mitochondria

To determine whether the presence of the RP loop is effective in facilitating transport of the gRNA to the nucleus, the relative concentration of gRNA was examined in the mitochondrial fraction of cells expressing either a hybrid gRNA with an RP loop or a gRNA lacking an RP loop. The hybrid gRNA displayed greater expression in the mitochondrial fraction than the non-hybrid gRNA. These results demonstrate that the presence of the RP loop on the gRNA is capable of resulting in translocation of the gRNA to the mitochondria (FIG. 5).

RP Loop Constructs can Affect Mitochondrial Gene Expression

Figure 7A:
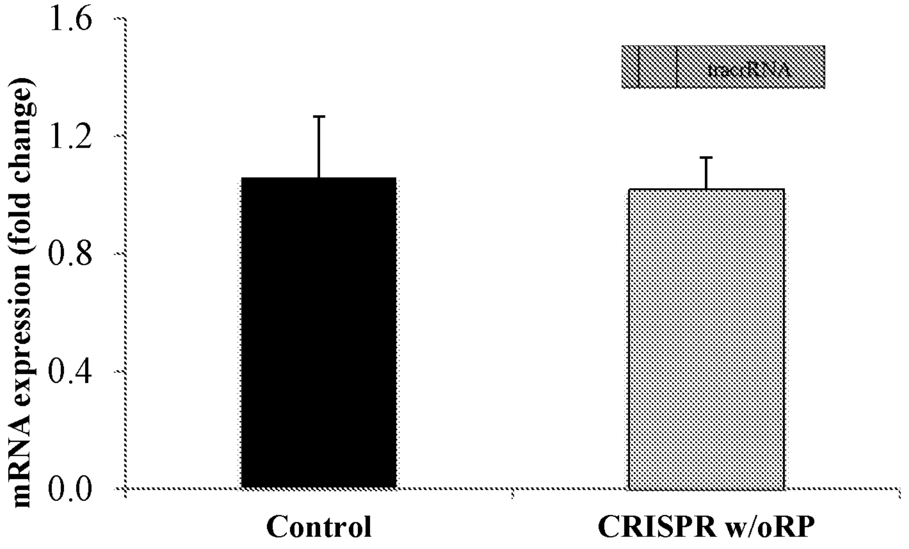
FIGS. 7A-7B. RP loop constructs affect mitochondrial gene expression.
Figure 7B:
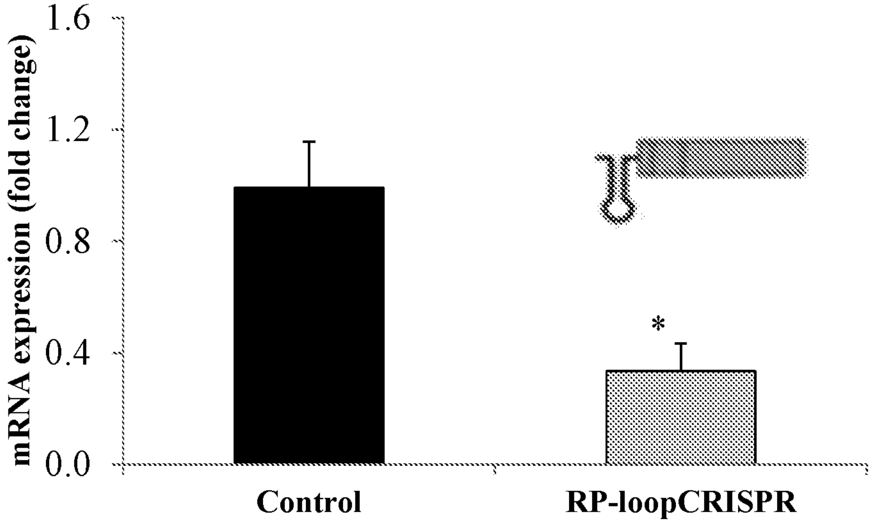
Figure 8:
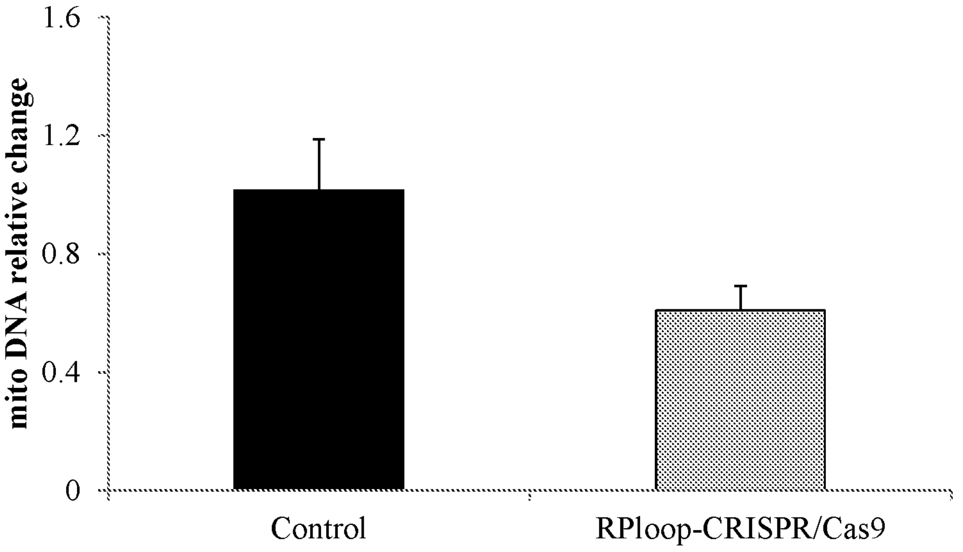
FIG. 8. Reduction in mouse mitochondrial content after RP loop CRISPR transfection. Murine embryonic fibroblasts (MEFs) transfected with the mito-Cas9 and hybrid gRNA contained 39% less mtDNA relative to the MEFS transfected with a control vector after 24 hours.

To determine whether a mito-CRISPR/Cas9 system can effectively edit mtDNA, a construct was developed that targets the mtND4 target gene (SEQ ID NO.:7). Cells were then transfected with either a control vector, a vector encoding an mtND4 gRNA but lacking an RP loop, or an mtND4 hybrid gRNA with an RP loop. The expression vector also contained an MLS-Cas9. Following transfection, cells were assayed for expression of mtND4 mRNA. The cells transfected with either a control vector or a gRNA targeting mtND4 but lacking an RP loop had similar levels of mtND4, indicating that MLS-Cas9 alone and MLS-Cas9 in combination with a gRNA are not sufficient to affect mtND4 expression (FIG. 7A). Surprisingly, however, when all elements of the system were present (MLS-Cas9 and the hybrid gRNA with RP loop), the relative level of mtND4 was significantly reduced by 67% (FIG. 7B). This result indicates that the presence of the RP loop in combination with the MLS-Cas9 is sufficient to facilitate gene editing in the mitochondria.

Reduction in mtDNA after RP Loop CRISPR Transfection

To determine whether the mito-CRISPR/Cas9 system can affect mitochondrial heteroplasmy, murine embryonic fibroblasts (MEFs) were transfected with MLS-Cas9 and a hybrid gRNA. Twenty-four hours after transfection, the cells contained 39% less mtDNA relative to the MEFS transfected with a control vector. These results indicate that the mito-CRISPR/Cas9 system is capable of changing the amount of mtDNA in a cell.

Cybrid Formation

To create cybrids, protoplasts from mitomycin inactivated fibroblasts, homoplastic for mtDNA variants, were fused with germ line competent female mouse embryonic stem cells (ESCs) resulting in the creation of heteroplasmic mouse ESCs. A germline competent female ESC cell line is capable of passing on its genetic material to progeny. These ESCs containing heterogeneous mitochondrion within the heteroplasmic cytoplasm, can be used as a tool to develop mouse strains carrying heteroplasmic mitochondria in their tissues. "To bias heteroplasmy" means that in heteroplasmic cells by targeting with the disclosed mito-CRISPR/Cas9 disclosure we can cause selective deletion of either mutant, variant, or wild-type mitochondria depending upon the type of target polynucleotide sequence selected in the hybrid gRNA.

Assays to Determine Heteroplasmy

High Resolution Melt Analysis (HRMA) is a type of genotyping by variant scanning that can be seamlessly appended to PCR amplification. Any point mutation can be identified by a-typical melting curve of a different shape than the control. PCR is performed in CFX-96 thermal cycler with Sso-EvaGreen master mix followed with analysis by Precision Melt Analysis software (BioRad).

Figure 9:
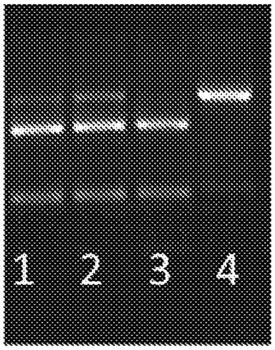
FIG. 9. Identification of mtND4 cybrids by RFLP of heteroplasmic mitochondria. Lanes 1 and 2 contain cybrid samples. Lane 3 contains a sample from an ESC with wild-type mitochondria. Lane 4 contains an ND4 mutant fibroblast. ESCs have an AvaI restriction site in ND4 which results in the generation of two lower bands. The cybrid sample has a mixed population of cut and un-cut bands.

Restriction Fragment Length Polymorphism (RFLP) is a standard technique that involves digestion DNA with specific restriction endonuclease unique to one form of DNA. To study mitochondrial heteroplasmy, PCR can be performed and the PCR product can be digest to identify the presence of a PCR product with unique restriction enzyme sites (FIG. 9). mtND4 cybrids can be identified because they have an Aval restriction site only in wild-type mitochondria.

Mito-CRISPR/Cas9 Gene Therapy to Treat LHON

Methods of the disclosed invention may be used to treat Leber Hereditary Optic Neuropathy (LHON) in patients with the mtND4 G11778A mutation. These patients require repair of the mtND4 gene in the mitochondria of their retinal ganglion cells (RGCs).

A recombinant expression system comprising (i) the hybrid gRNA encoded by SEQ ID NO.: 8 or an equivalent thereof, (ii) an MLS-Cas9 polynucleotide such as mSpCas9, and (iii) a recombinant AAV2 expression vector such as scAAV2 is co-transfected with (a) a packaging vector such as pHLP vector and (b) an AAV2 serotype-specific rep-cap vector such as pAdeno into a host cell line. The host cells must be competent for viral production (e.g. HEK293). Transfection methods may include calcium phosphate transfection or use of a cationic liposome transfection reagent at a vector ratio of 1:1:1.

Viral particles containing the hybrid gRNA and mSpCas9 are harvested from the culture supernatant. Viral particles may be purified and enriched by centrifuging the harvested supernatant in an ultracentrifuge over a solution of sucrose and BSA or an equivalent thereof. Viral pellets are then resuspended in a buffer to minimize clumping (e.g. DNase I and/or EDTA-containing buffers). Finally, the resuspended pellet is passed through a low-protein-binding 5 um syringe filter. Further viral fractionation may be performed if additional enrichment is required to achieve effective titer.

Purified viral particles are prepared for administration by suspension in saline, PBS, or another pharmaceutically acceptable carrier, diluent, or excipient compatible with intravitreal injection. Viral titer is determined by any method known in the art including, but not limited to, PCR for the presence of the viral genome, multiplicity of infection (MOI), and infection of a reporter cell line followed by an assay for wild-type mtND4 gene expression.

Administration of the viral particles is via injection into the vitreous space of the eye. Topical anesthetic may be applied to the surface of the eye followed by a topical antiseptic solution. Patients may receive one or more injections of an effective dose of viral particles. An effective dose may be $9\times10^{9}$ vector genomes (vg), $3\times10^{10}$ vg, or $9\times10^{10}$ vg. Alternatively, an effective dose may be $1\times10^{8}$ vg or more (e.g. $1\times10^{9}$, $1\times10^{10}$, $1\times10^{11}$, $1\times10^{12}$, or $1\times10^{13}$). Following treatment, patients are assessed for improvements to the central visual function and evaluated for cellular and humoral responses to AAV2.

EXAMPLE 2

Mitochondrial diseases, i.e. those causing primary defects in mitochondrial oxidative phosphorylation (OXPHOS), are genetically and clinically highly heterogeneous disorders, with phenotypic manifestations ranging from mild hearing impairment to severe progressive multisystem disorders. Genetically, mitochondrial disorders can be distinguished into those resulting from mutations in the mitochondrial genome (mtDNA) and those associated with alterations in nuclear genes. Whereas the latter are inherited in a Mendelian manner, pathogenic mutations in mtDNA are exclusively maternally inherited. The overall prevalence of mitochondrial disease is difficult to determine. According to population studies, the incidence of mtDNA disease is approximately 1:5,000 in adults, but as many as 1:200 individuals harbor a pathogenic mtDNA mutation that could be transmitted to offspring, and the population prevalence for specific pathogenic mtDNA mutations is as high as 1:400 (MELAS 3243A>G mtDNA mutation).

In most disorders associated with mutations in mtDNA, the individuals' cells are heteroplasmic, i.e. they contain a mixture of mutant and wild-type mitochondria, with ratios that may differ between tissues. The manifestation of defects associated with pathogenic mtDNA mutations and the severity of symptoms depend on the proportion of mutant mitochondria, and the threshold for the manifestation of defects varies substantially between mutations and between different tissues with different energy requirements. In heteroplasmic women, the risk of transmitting disease-causing loads of mutant mtDNA is unpredictable. After segregation of mtDNA molecules in primordial germ cells, mtDNA content increases dramatically during oocyte development, producing different mutation loads, followed by additional tissue-specific segregation during early embryonic and fetal development. Strategies to prevent transmission of mtDNA disorders include the use of donated oocytes, preimplantation genetic diagnosis, and mitochondrial replacement therapy (MRT), which involves the transfer of nuclear DNA from a heteroplasmic oocyte or embryo into a donor cytoplast with wild-type mitochondria by pronuclear or spindle transfer. Incompatibility between donor and host mitochondria is associated with genetic drift leading to loss of donor mtDNA and reversion to the mutant haplotype.

An alternative approach to reduce heteroplasmy for mutant mtDNA below pathogenic threshold levels could be the use of mitochondrially-targeted nucleases that selectively cleave specific mtDNA haplotypes, resulting in their degradation and shifting the heteroplasmy ratio towards the desired mtDNA haplotype. Support for this approach can be found in results demonstrated with restriction endonucleases, zinc-finger nucleases (mtZFN), and transcription activator-like effector nucleases (mito-TALENs). In contrast to restriction enzymes for which few applicable mutant sequences exist, mtZFN and mito-TALENs can be designed and engineered to selectively cleave a range of mutant mtDNA sequences. Potential drawbacks to these strategies include the relatively labor and cost-intensive production, and size compatibility with current virus-based delivery systems to tissues, and the need for repeated transfections to achieve effective heteroplasmy shift.

A powerful genome editing and targeting methodology is based on clustered regularly interspaced short palindromic repeats (CRISPR) bacterial immune systems. The most widely used constructs use the CRISPR associated (Cas) 9 nuclease and a chimeric single guide RNA (sgRNA), which incorporates an approximately 20-nucleotide region that pairs with the DNA target of interest, guiding the Cas9 nuclease to its target and resulting in sequence specific cleavage. CRISPR/Cas9 systems are relatively simple to generate, adaptable to multiple sequences, and more cost effective with smaller expression constructs that facilitate virus-based delivery. Whether CRISPR-Cas9 could be used for the effective elimination of undesired mtDNA haplotypes remains unclear because targeted approaches to effectively import the gRNA component into mitochondria have not been reported. Similar to other mito-targeted proteins, import of the Cas9 nuclease into mitochondria appears to be enhanced by the addition of mitochondrial targeting signals. This example demonstrates that an endogenous pathway for mitochondrial RNA import can be used to mediate mitochondrial localization of sgRNA species, and, in combination with mito-targeted Cas9, would result in sequence specific cleavage of selected mtDNA haplotypes.

Manipulating or targeting mitochondrial genomes is a current challenge in the quest to address mitochondrial DNA based disease. In this example, targeting mtDNA was approached by facilitating transport of the CRISPR/Cas9 endonuclease components to the mitochondria by appending the CRISPR guide RNA to a PNPase derived stem loop element and the Cas9 component to a MLS. This example demonstrates that adding a PNPase derived stem loop element to the hybrid guide RNA improves import of the CRISPR in to the mitochondria. When targeted with Cas9 protein assisted with a mitochondrial membrane localization sequence (MLS), there is both a reduction in expression of ND4 mitochondrial gene coincident with a decrease in mtDNA copy number. This tool provides a useful adjunct to manipulate the mitochondrial genome including alteration in mitochondria heteroplasmy for unwanted variants.

Materials and Methods

CRISPR/Cas9 Constructs

The expression construct pX330-U6-Chimeric_BB-CBh-hSpCas9 (Addgene; plasmid #42230) for human codon-optimized SpCas9 and chimeric guide RNA expression plasmid was modified as follows: (1) The two nuclear localization signals (NLS) that flank the N and C terminals of Cas9 were replaced with mitochondrial localization signals (MLS); and (2) the human optimized Cas9 sequence was modified with codons optimized for mouse expression. The Cas9 with MLS construct was synthesized by GenScript, NJ, USA using their OptimumGene™-Codon Optimization algorithm and cloned into pX330-U6-Chimeric_BB-CBh-hSpCas9, producing a. MLS1 was the amino-terminal leader peptide of mouse ornithine transcarbamylase and MLS 2 the 23 amino acid leader peptide of cytochrome oxidase subunit 8 (COX 8). The mouse ND4 sgRNA target sequences including the RP loop sequence were selected based using a CRISPR design online tool (crispr.mit.edu/guides), custom synthesized by Genscript and cloned into pX330 backbone. They were synthesized and cloned into plasmid pUC57 with unique restriction sites (Pcil, Xba1) for sub-cloning back into pX330 backbone vector. Pcil is in the U6 promoter.

Generation of MLS-Cas9 mRNA and RP Loop-sgRNA

RNA secondary structure predictions were performed using M-fold. The DNA template for in vitro transcription of mSpCas9 was generated by PCR amplification of pX330, using a forward primer that included a T7 promoter (T7-HAtag-Cas9-F 5'-TAATACGACTCACTATAGGGATGT ACCCATACGATGTTCCAGATTACGCT)-3') (SEQ ID NO.: 10) and a reverse primer (Cas9-R: 5'-GCGAG CTCTAGGAATTCTTAC-3') (SEQ ID NO.: 11). Cas9 mRNA was then synthesized, using the mMESSAGE mMACHINE® T7 Ultra Kit (Life Technologies, Carlsbad, Calif.) and purified by LiCl precipitation. DNA templates of RP sgRNAs were also generated by PCR amplification of RPLoop ND4sgRNA, using forward primers T7-RPloop-F that included a T7 promoter (SEQ ID NO.: 12) 5'T AATACGACTCACTATAGGGTCTCCCTGAGCTTC AGGGAGT-3' and a common reverse primer sgRNA-R: 5'-AAAAGCACCGACTCGGTGCC-3' (SEQ ID NO.: 13). The ND4-RPloop sgRNAs were then synthesized using the MEGAshort-script™ T7 Kit (Life Technologies). RNA was purified and concentrated by using RNA Clean & Concentrator-5 Kit (Zymo Research Corp. Irvine, Calif.). The integrity of the synthesized RNAs was assessed using Agilent RNA 6000 Nano Kit with Agilent 2100 bioanalyzer Bioanalyzer (Agilent Technologies, Santa Clara, Calif.).

Cell Culture

Primary mouse embryonic fibroblast (MEF) were derived from Tg(DR4) 1Jae/J mice stock No: 003208 (Jacksons Laboratories). Human HEK293K cells were ATCC CRL-1573 (American Type Culture Collection, USA). Transient transfection with synthetic Cas9 and sgRNAs was performed in either MEF or 293K cells using the TransIT®-mRNA Transfection Kit (Mirus Bio LLC) in OptiMEM medium (Invitrogen).

In Vitro Assay to Test Mito-CRISPR Functionality and Specificity

Mito CRISPR target selection was performed using the GeneArt® Genomic Cleavage Selection Kit (cat #A27663, ThermoFisher Scientific), which is based on restoration of reporter Orange Fluorescent Protein (OFP) expression if endonuclease activity at a target sequence induces DNA DSB and repair. Target DNA fragments containing the sgRNA target sequence (mtND4 112004G) and control (mtND 4 112004A) were cloned separately into the pGCS reporter vector producing pGCS-wt and pGCS-variant. Co-transfection of reporter constructs into HEK293K was performed using TranslT-2020 transfection reagent (Mirus Bio LLC), with RP-sgRNA/Cas9 or other genome editing tools (mito-TALENs). Orange fluorescence was visually assessed at 48 hrs post transfection using an Evos cell imaging system (ThermoFisher Scientific, USA).

Immunostaining

MEF cells were grown on cover slips in 12-well plates and transfected with either pX330 with NLS hCas9 or pX MLS mCas9 plasmid. hCas9 is a Cas9 with leader sequence pX330 which has a humanized nuclear localization signal (NLS) and humanized codons. After 24 hours, media was removed and cells fixed by two brief washes in ice-cold acetone. Cells were blocked in 3% goat serum in 1×TBS for 30 mins, followed by staining with Cas9 antibody monoclonal antibody 4G10 cat #: C15200216 (Diagenode Inc.) (1:200 dilution) added with gentle shaking for 2 hrs at room temperature. Cells were washed in 1% goat serum in 1×TBS. Secondary anti-mouse antibody Alexa 488 (Molecular Probes) at 3 μg/ml dilution was added for 1 h at room temperature. After washing with goat serum in 1×TBS cells were mounted Vectashield with DAPI and images taken using a confocal microscope.

Mitochondrial DNA/RNA Isolation

Mitochondrial DNA was isolated using Mitochondrial/Cytosolic Fractionation Kit (cat #K256-25 (BioVision Inc. CA)) following manufacturer's instructions. MEF cells were grown in 6-well plate to 80% confluency before transfection with RPloop-sgRNA (1.5 ug/well) using TransIT®-mRNA Transfection Kit (Mirus Bio LLC). After 24 h post transfection, 5×106 cells were harvested using trypsin (0.05% trypsin-EDTA). Cell membranes were disrupted in cytosolic buffer using a Dounce homogenizer followed by successive centrifugation steps. Mitochondrial pellets were then used for isolating mitoDNA using QIAamp DNA mini Kit (Qiagen). DNA was eluted in water and quantified by NanoDrop 2000 UV-Vis Spectrophotometer (Thermo Scientific).

Quantitative PCR

DNA and RNA were isolated using QIAamp DNA Mini Kit (Qiagen) and mirVana RNA isolation kit (Ambion-ThermoFisher), respectively. cDNA synthesis of RNA was performed by using SuperScript® VILO™ cDNA Synthesis Kit cat #11754050 (ThermoFisher Scientific). QPCR was performed using Precision Melt Supermix containing EvaGreen dye (cat #172-5110) using CFX96 Touch™ Real-Time PCR Detection System (BioRad, USA). PCR primers are provided herein as SEQ ID NOs.: 20-31.

Results

Targeting Mitochondrial DNA Using CRISPR/Cas9

CRISPR/Cas9-mediated cleavage of a mitochondrially encoded gene was evaluated using different mouse haplotypes of mitochondrially encoded NADH:ubiquinone oxidoreductase core subunit 4 (mtND4). Specifically, residue 11204 of mtND4 was targeted, at which a G->A mutation corresponds to a mutation in human MT-ND4 associated with complex I deficiency and respiration defects. Using mouse mtDNA sequences, target guide sequences were selected against base 11204G of mt-Nd4, which encodes R356, and these were used to construct hybrid guide RNAs (gRNA) composed of the CRISPR array and tracrRNAs. The guide sequence selected scored 92 with only 1 off target site. Activity and allele-specificity of gRNA in vitro in HEK293K cells following co-transfection with Cas9 expression plasmid and orange fluorescent protein (OFP)-based reporter constructs for mtND4 112004G and mtN 4 112004A. OFP fluorescence indicating base-specific cleavage was observed in cells transfected with the 11204G sequence but not with the mutant 11204A sequence.

Figure 11:
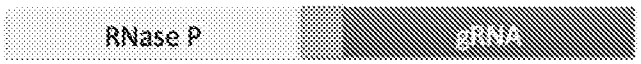
FIG. 11. Sequences and map for pX-RPloop-gRNAMLS-mSpCas9 as described in Example 2 herein. The RNaseP-spacer-gRNA sequence is presented as SEQ ID NO.: 16. The RNaseP loop region is SEQ ID NO.: 17. The spacer rest site is SEQ ID NO.: 18. The RPloop-pac1 site-mND4-gRNA #2-Chimeric gRNA scaffold is SEQ ID NO.: 19.
Figure 11:
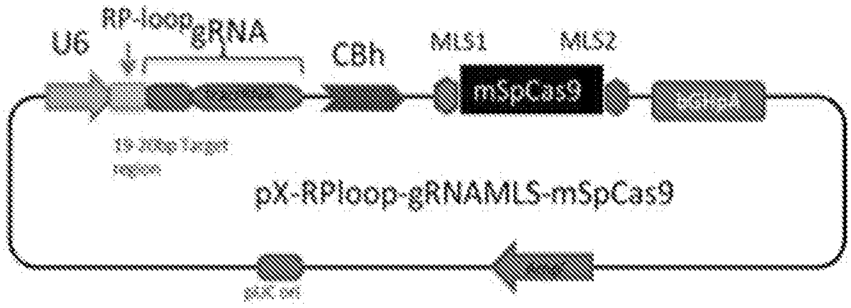
Figure 11:
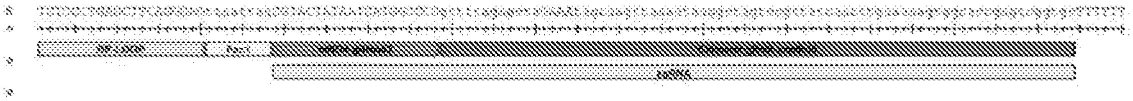

To mediate selective import of this construct into mitochondria, a 22-nucleotide stem-loop element (PR-loop) that is a component of the mRNA for polynucleotide phosphorylase (PNPASE) was used. PNPASE is localized to the inner mitochondrial membrane and regulates the import of nuclear-encoded RNAs into the mitochondrial matrix. Addition of the RP-loop to transcripts that do not normally locate mitochondria has been shown to allow for RNA import in a PNPASE-dependent manner. A hybrid sgRNA was constructed in which the RP loop was appended to the 5'-end of the sg RNA construct designed to selectively base-pair with the wild-type mtND4 target-20 nt sequence (FIG. 11). To facilitate future sub-cloning, an 8-nucleotide Pac1 restriction site separated the RP-loop and sgRNA. Based on structure predictions using the M-fold algorithm, the hybrid RP-loop-gRNA maintained the secondary structure of the stem-loop required for mitochondrial import [Initial ΔG=−45.00 kcal/mol at 370 C].

To facilitate transport of Cas9 protein to the mitochondria of mouse cells, a CRISPR/Cas9 expression plasmid (pX330-U6-Chimeric_BB-CBh-hSpCas9) was modified such that a mouse-optimized Cas9 sequence was flanked by two mitochondrial localization signals (MLS). The amino terminal signal (MLS1) consisted of the amino-terminal leader peptide of mouse ornithine transcarbamylase) and the C-terminal MLS2 of the 23 amino acid leader peptide of cytochrome oxidase subunit 8. As codon bias can affect translation and activity of Cas9 protein in cell culture systems, a Cas9 coding sequence that had been optimized for mouse expression was also used. Transfection of MEF cells with pX330-U6-Chimeric_BB-CBh-hSpCas9, in which the coding sequence of Cas9 is flanked by nuclear localization signals, resulted in strong nuclear signal of Cas9 in immunostaining assays. In contrast, cells transfected with the modified expression construct encoding Cas9 flanked by MLS1 and MLS2, lacked Cas9 signal in the nuclei and exhibited immunostaining throughout the cytoplasm, consistent with mitochondrial localization.

Figure 12:
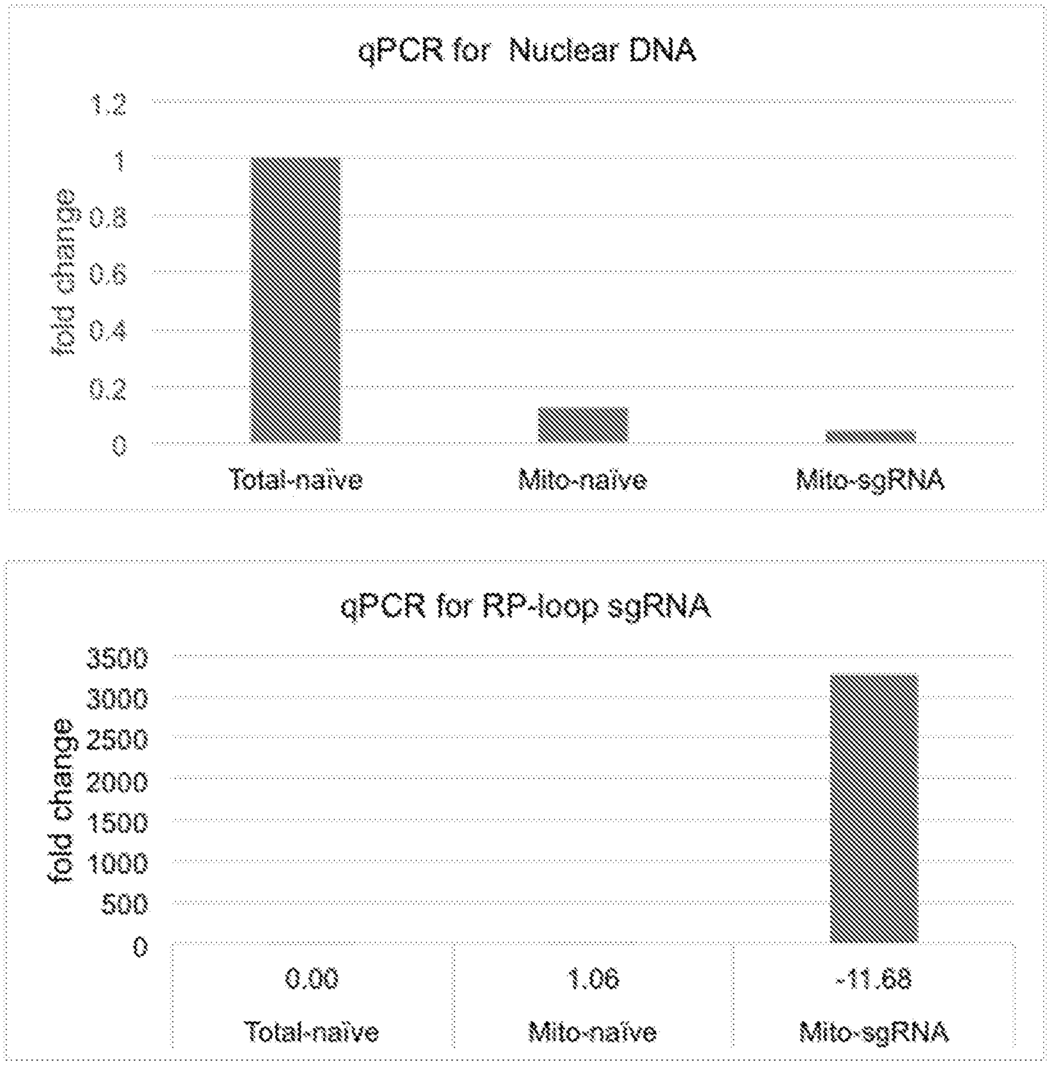
FIG. 12. RP loop-sgRNA is enriched in the mitochondrial fraction of MEF cells as described in Example 2 herein. The data is presented as fold change (ΔΔCt).

To test the mitochondrial localization of the RP-loop sgRNA construct, an sgRNA construct with RP-loop and sgRNA without RP-loop were transfected into MEFs. Quantitative PCR verified an fold enrichment of the RP-loop construct in the mitochondrial fraction (FIG. 12).

Inclusion of the Stem Loop Facilitates CRISPR Associated Reduction of Targeted mtDNA Genomes Although Crispr+Cas9 can be localised to the mitochondria, functional localization within the mitochondrial genome requires evidence of targeted mtDNA endonuclease activity. MEFs were co-transfected with the Cas9 expression construct alone (RNA or plasmid) or in combination with RP-loop-gRNA. Inclusion of RP-loop-gRNA in the RNA constructs synthesized both MLS-Cas9 and ND-4 targeting resulted in a relative (as measured by reference to nuclear genome SdhA DNA) reduction of the overall mtDNA content (SdhA as relative control for nuclear DNA versus mitochondrial DNA). The knockdown was significant in three independent experiments relative to MLS Cas9 as control.

Specificity for Mouse mtDNA ND4

Figure 13:
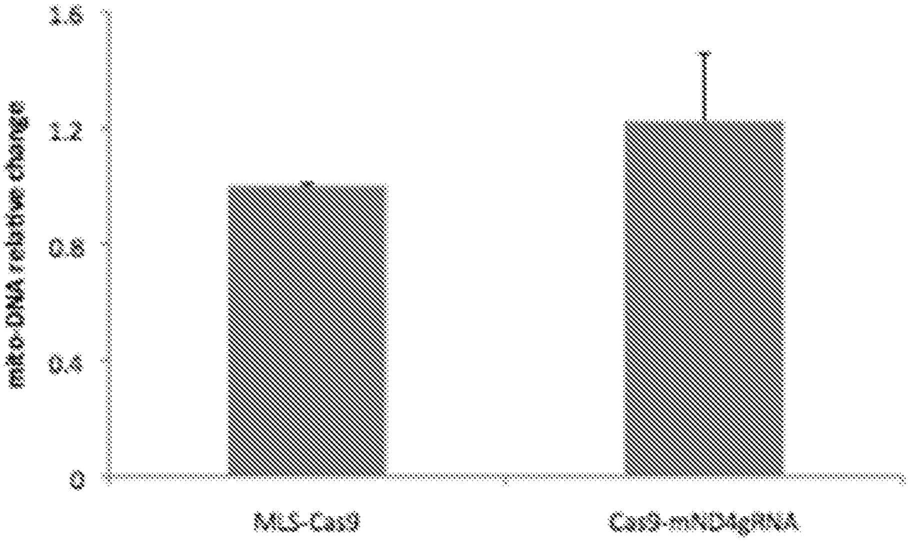
FIG. 13. Human 293K with DN4 gRNA and RP-loop as negative control for target specificity as described in Example 2 herein.

The human ND4 gene sequence differs slightly from the mouse. This difference was utilized to assay the specificity of CRISPR cleavage activity of the mouse ND4 target sequence by transfecting in into human 293K cells. Transfection with either MLS Cas9 alone, or MLS Cas9 in combination with the hybrid Cas9/hybrid RPloopgRNA guide RNA did not result in detectable changes in mtDNA levels (FIG. 13).

Next, expression levels of mitochondrially-encoded transcripts in MEFs after transfection with Cas9/hybrid RPloopgRNA were quantified. At 24 hours post transfection, a reduction of ND4 transcripts compared to transfection with the MLS Cas9 RNA alone and Gapdh as internal RNA control and reductions in ND1 and Cox 3 were observed.

Without being bound by theory, these findings are consistent with selective cleavage of mtDNA at the ND4 target sequence, abolishing ND4 transcription. Although transcription of ND1 and Cox3 would not be immediately blocked, lower transcripts levels reflect depletion of mtDNA as a consequence of CRISPR/Cas9 mediated cleavage. Specifically targeting single nucleotide residue at position 11204 (-nt G), with significant reduction of the mtND4 target and concomitant reduction of other mtDNA transcripts is associated with the gradual elimination of individual cleaved mtDNA genomes within mitochondria.

These findings indicate successful mitochondrial localization of the hybrid sgRNA. Studies with knockdown DNA or RNA were harvested after 24 h because mitochondrial DNA knockdown in non-heteroplasmic cells may affect viability at longer incubation times and non transfected cell replication could distort the results. Without being bound by theory, different incubation times may be critical in assessing efficacy. It is anticipated that other times including 4 hours, 6, hours, 8 hours, 10 hours, 12 hours, 16 hours, 18 hours, 20 hours, 22 hours, 26 hours, 28 hours, 30 hours, 36 hours, 40 hours, 44 hours, 48 hours, 54 hours, 60 hours, 64 hours, 72 hours, 96 hours, 5 days, 6 days, 7 days, 8 days, 9 days, 10 days, 11 days, 12 days, 13 days, 14 days, or 21 days will be effective.

To avoid cell death, an in vitro synthesized RNAs for both sgRNA and Cas9 was used for transient expression, instead of using a plasmid which would continuously express uncontrolled levels of the complex. DMEM medium was supplemented with 50 ug/ml of uridine and 100 mM of pyruvate.

CRISPR has limited number of target points in any genome unlike TALENS and ZFN that can target most nucleotides. However there is a rapidly developing variety of CRISPR-like gene editing molecules that are being reported in the literature and should be amenable to stem loop mediated transport into the mitochondria.

Figure 10:
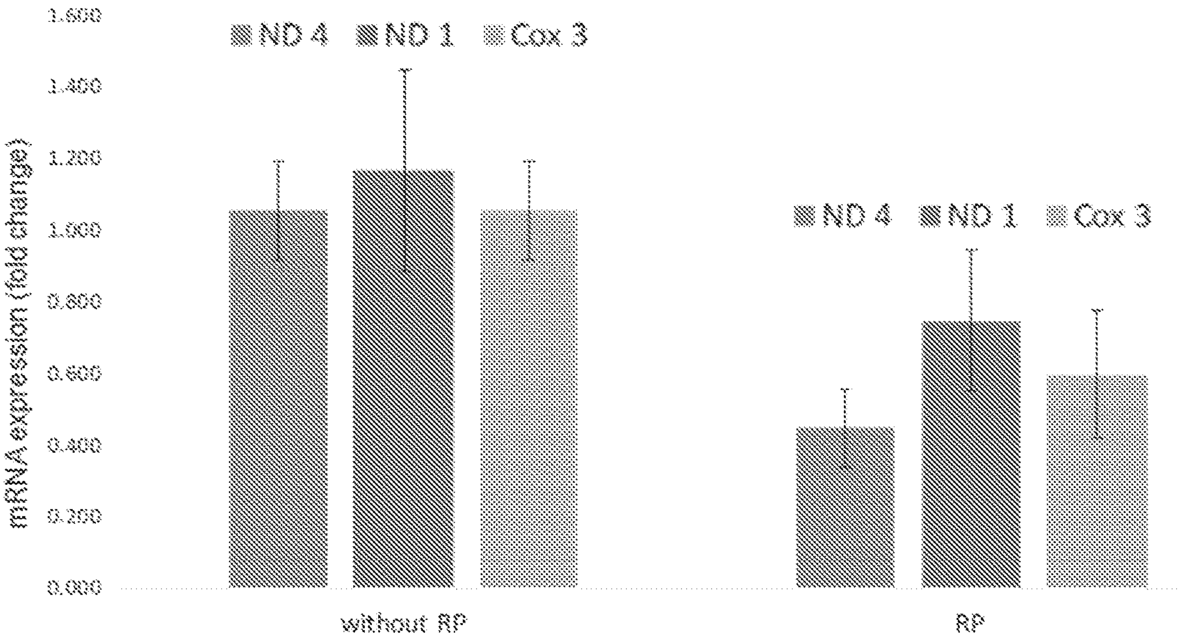
FIG. 10. RP-loop chimeric guideRNA base CRISPR/Cas9 system is significantly more efficient than the guideRNA without RP-loop. Reduction in mRNA expression of mitochondrial genes with RP loop chimeric guide relative to the corresponding guideRNA without RP loop RNA in Mouse Embryonic Fibroblast. Only the ND4 gene, which is the specific target of CRISPR/Cas9, shows significant reduction in expression ($p=0.003$). Other mitochondrial genes show a trend towards reduced expression but do not reach significance (ND1 $p=0.99$; Cox3 $p=0.07$). The reduction in the expression of non-target genes is expected because once the ND4 specific CRISPR/Cas9 cuts the mitochondrial DNA by recognizing the target sequence it causes an overall reduction in the mitochondrial population which accounts for the reduced expression of other mitochondrial genes. The effect is more significant for the gene in close proximity to the target sequence (e.g. Cox3).

The findings presented in this example indicate that CRISPR/Cas9 can be more effectively delivered to mitochondria using the RP stem loop RNA element (FIG. 10). This tool has the potential to be used to manipulate mitochondrial heteroplasmy in vivo and and with cell based therapy. These approaches could also produce more representative animal models of mtDNA disease.

Without being bound by theory, in vivo PNPASE facilitated import may not be very efficient. However, as reported herein, a relatively robust RP loop mediated mitochondrial localization was observed, resulting in reduction in total mtDNA at 24 hours and a reduction in expression of the targeted gene, ND4. Without being bound by theory, alternative approaches such as mtZFN's may be useful as well. The effectiveness of each round of treatment and the possible need to select transfected cell remain a critical factor in extension to therapeutic intervention. Without being bound by theory, a microinjection approach could provide efficient manipulation of mitochondrial heteroplasmy in zygotes or gametes by microinjection of the editing reagents.

EXAMPLE 3

Alternatives to SpCas9

The following exemplary SpCas9 alternatives require additional modifications such as the addition of an RP-loop to make chimeric guideRNAs and replace NLS with MLS as described above. These alterations will make the system appropriate for mitochondrial targeting and knockdown.

*Staphylococcus Aureus* Cas9 (SaCas9)

Figure 14:
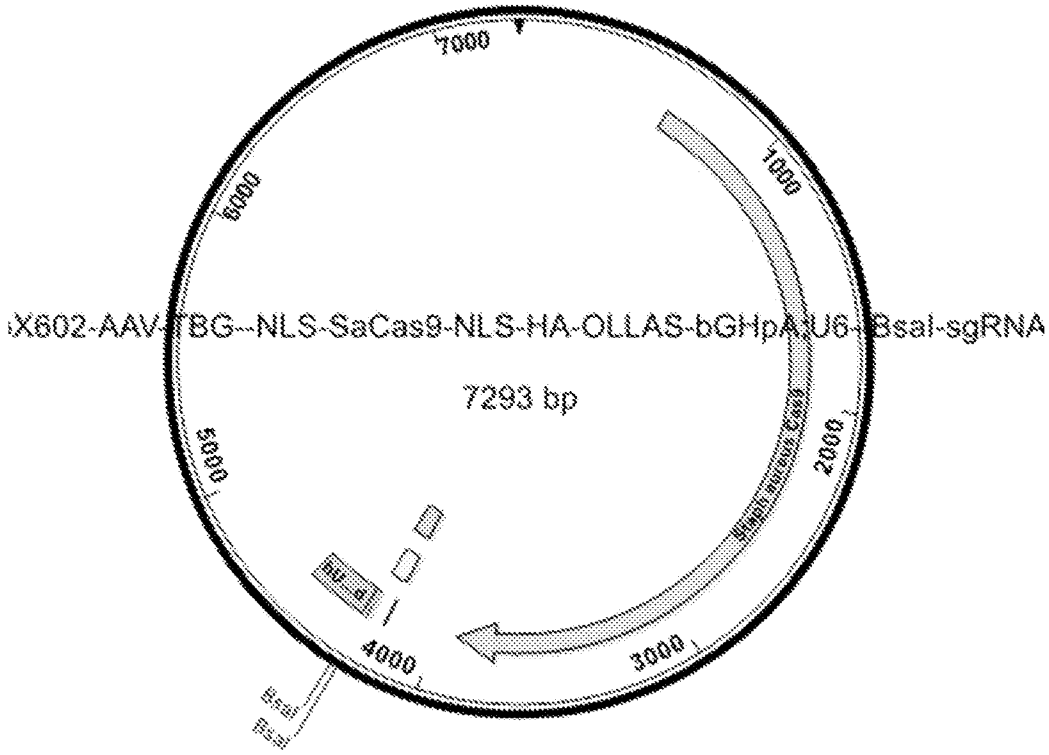
FIG. 14. Exemplary AAV vector with both saCas9 and sgRNA (pX602-AAV-TBG-NLS-SaCas9-NLS-HA-OL-LAS-bGHpA-U6-BsaI-sgRNA).
Figure 15:
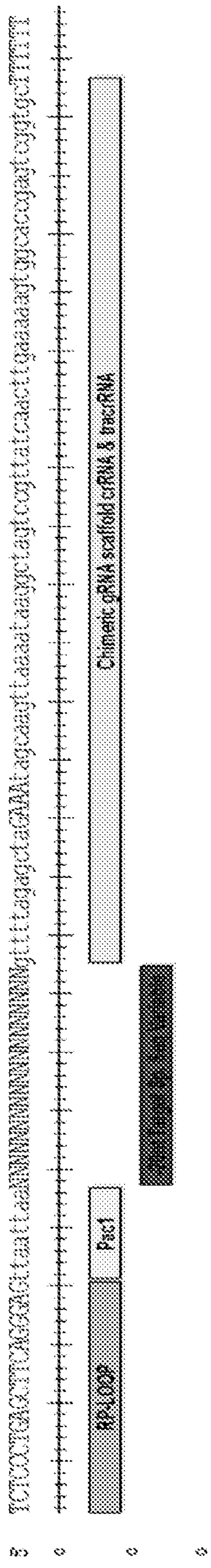
FIG. 15. Annotation of SEQ ID NO.: 6.
Figure 16:
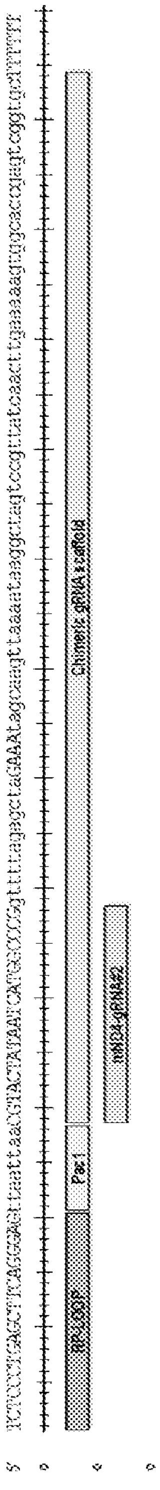
FIG. 16. Annotation of SEQ ID NO.: 7.
Figure 17:
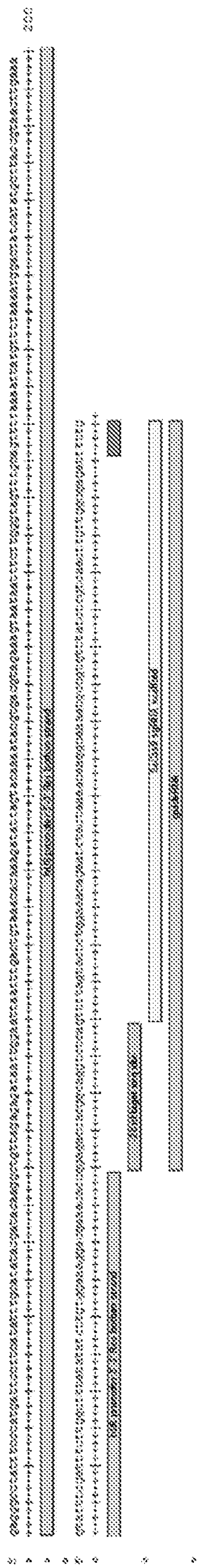
FIG. 17. Annotation of SEQ ID NO.: 38.
Figure 18A:
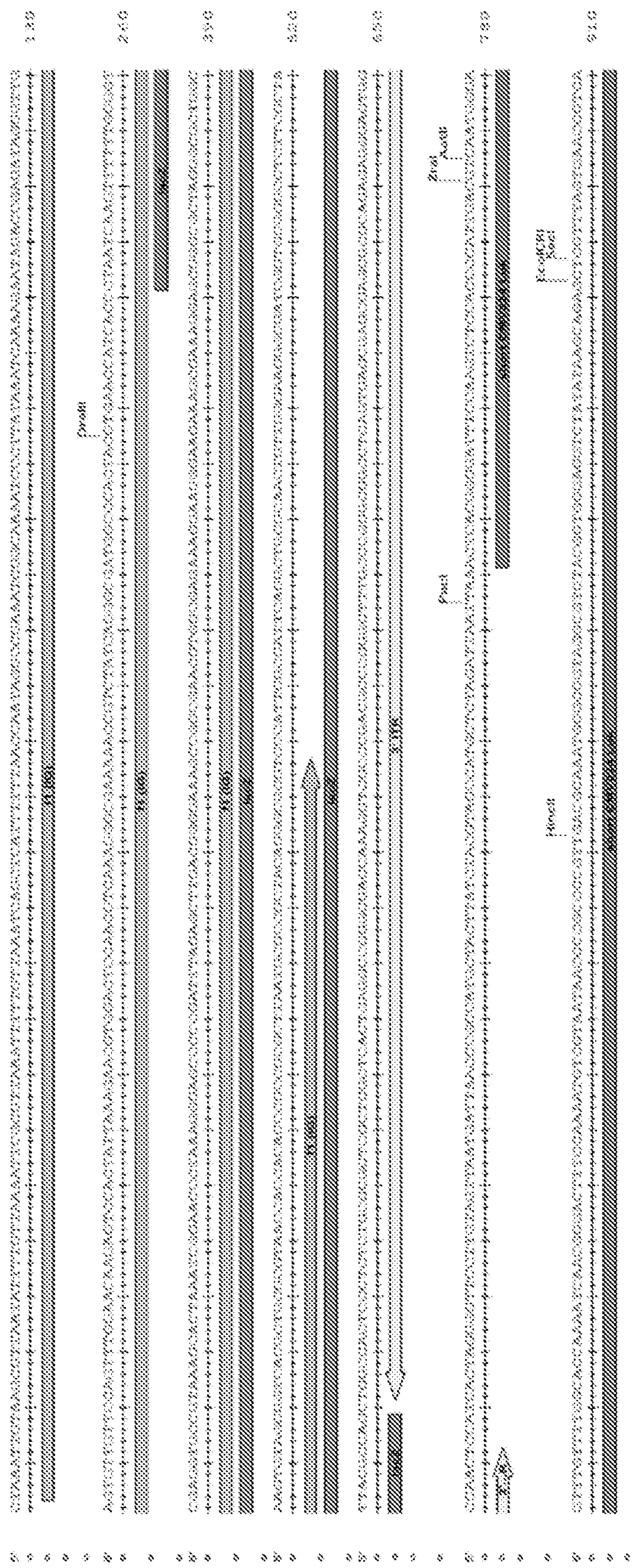
FIG. 18A-18E. Annotation of SEQ ID NO.: 32.
Figure 18B:
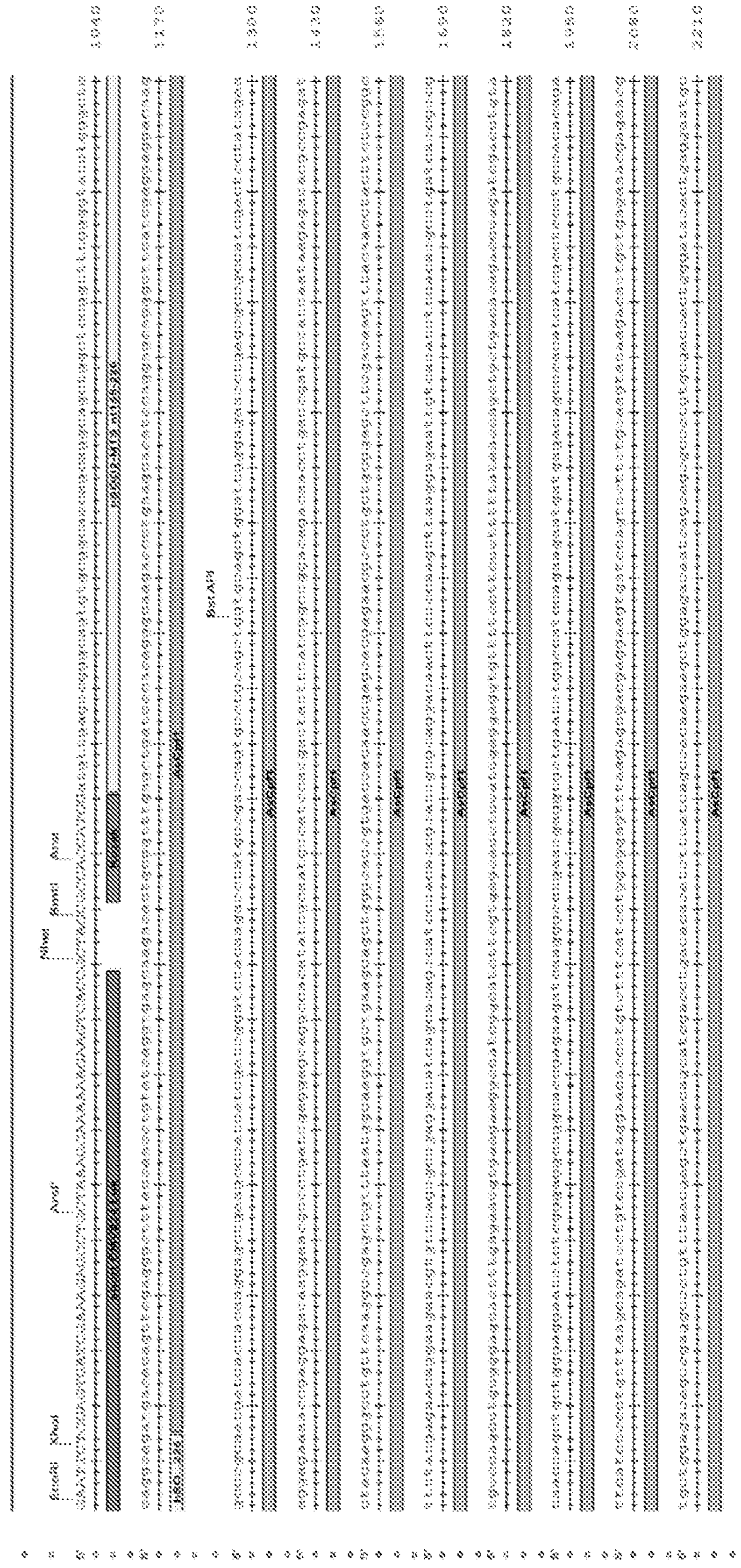
Figure 18C:
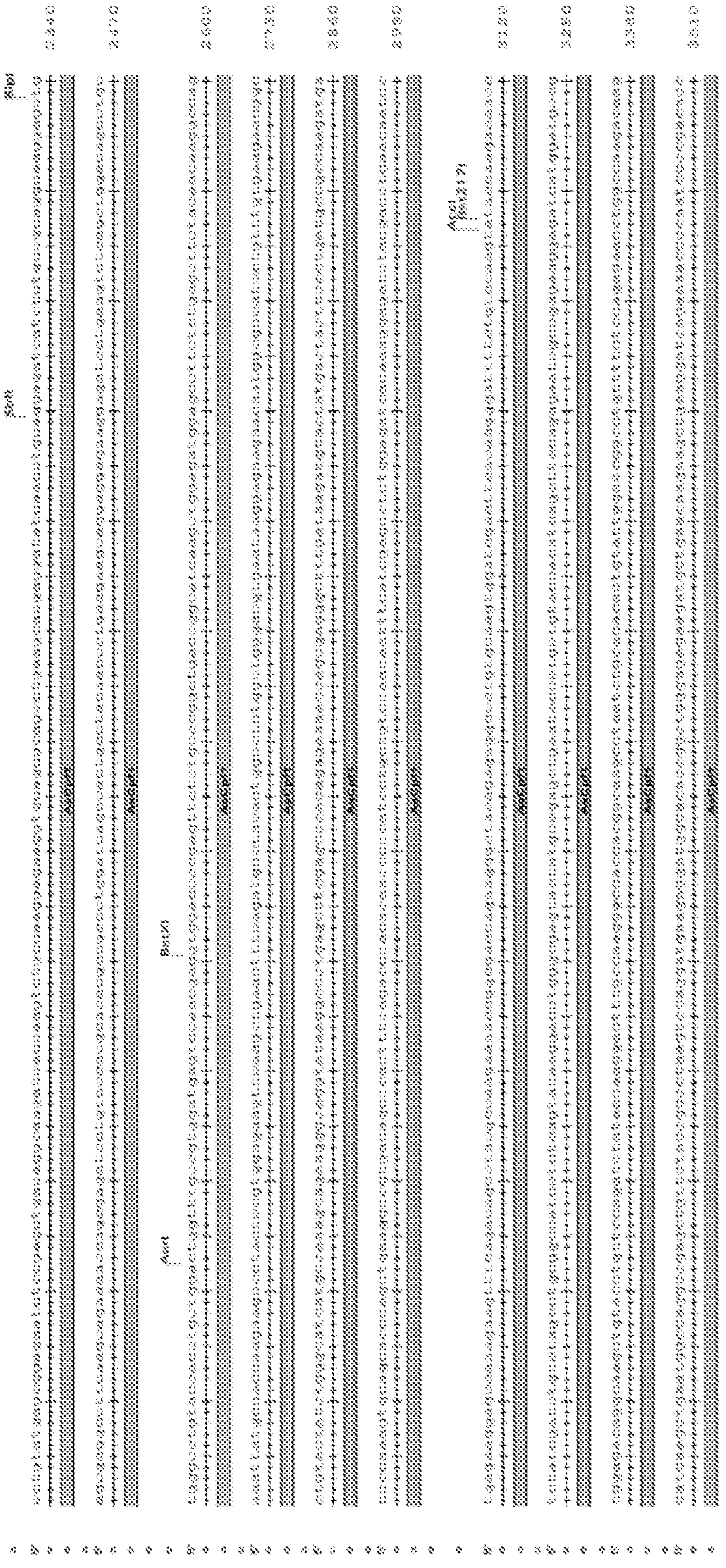
Figure 18D:
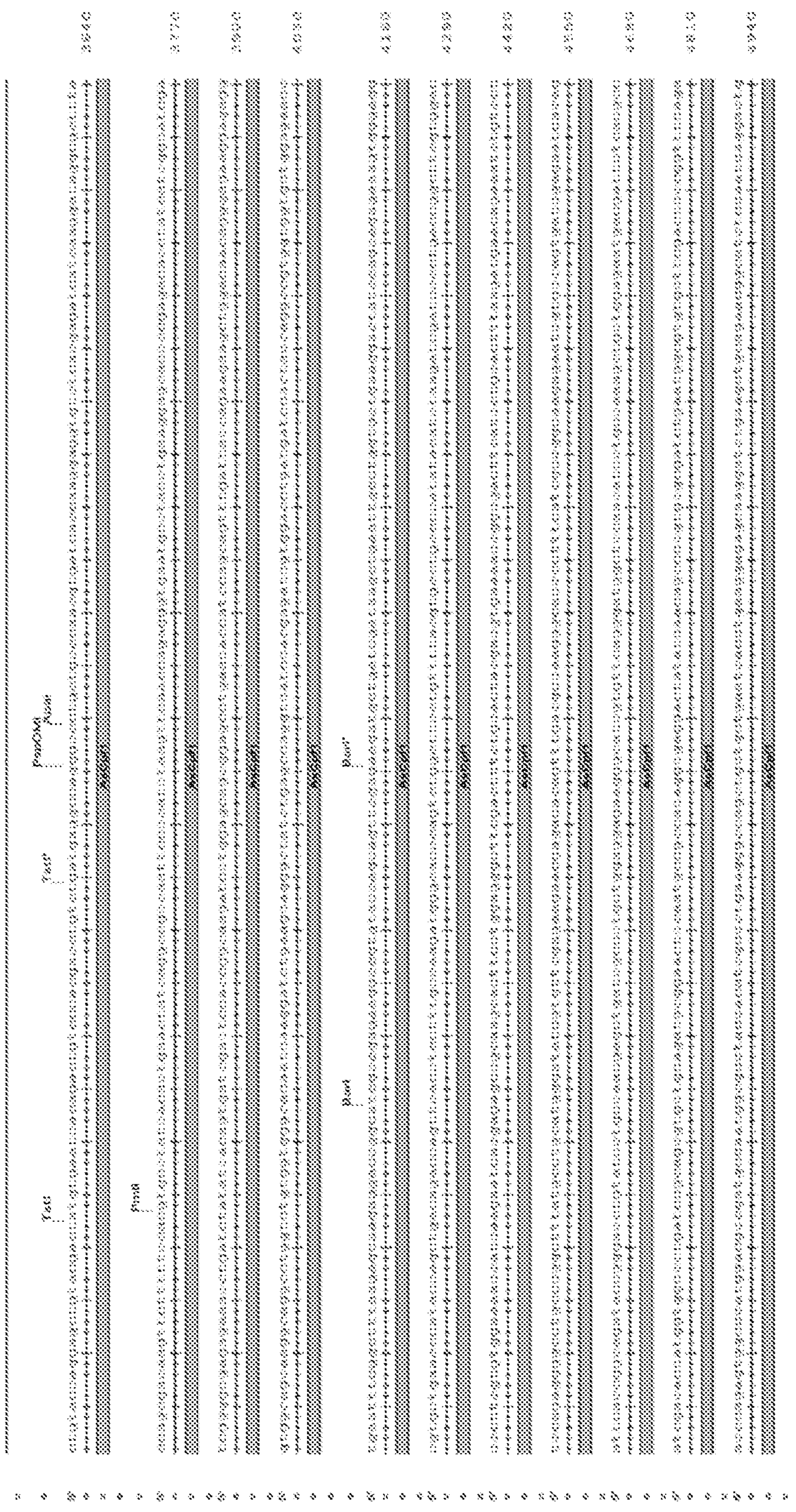
Figure 18E:
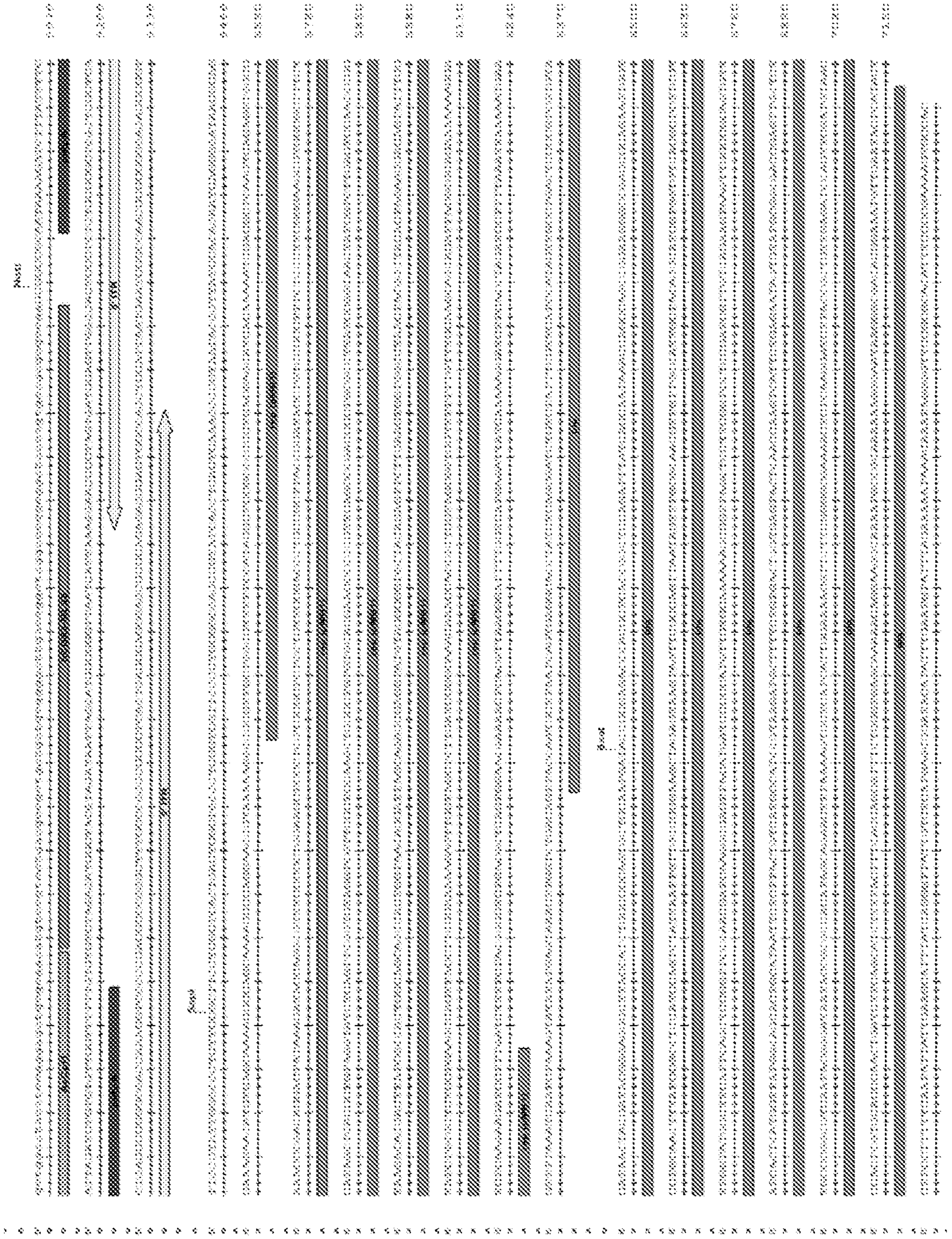
Figure 19A:
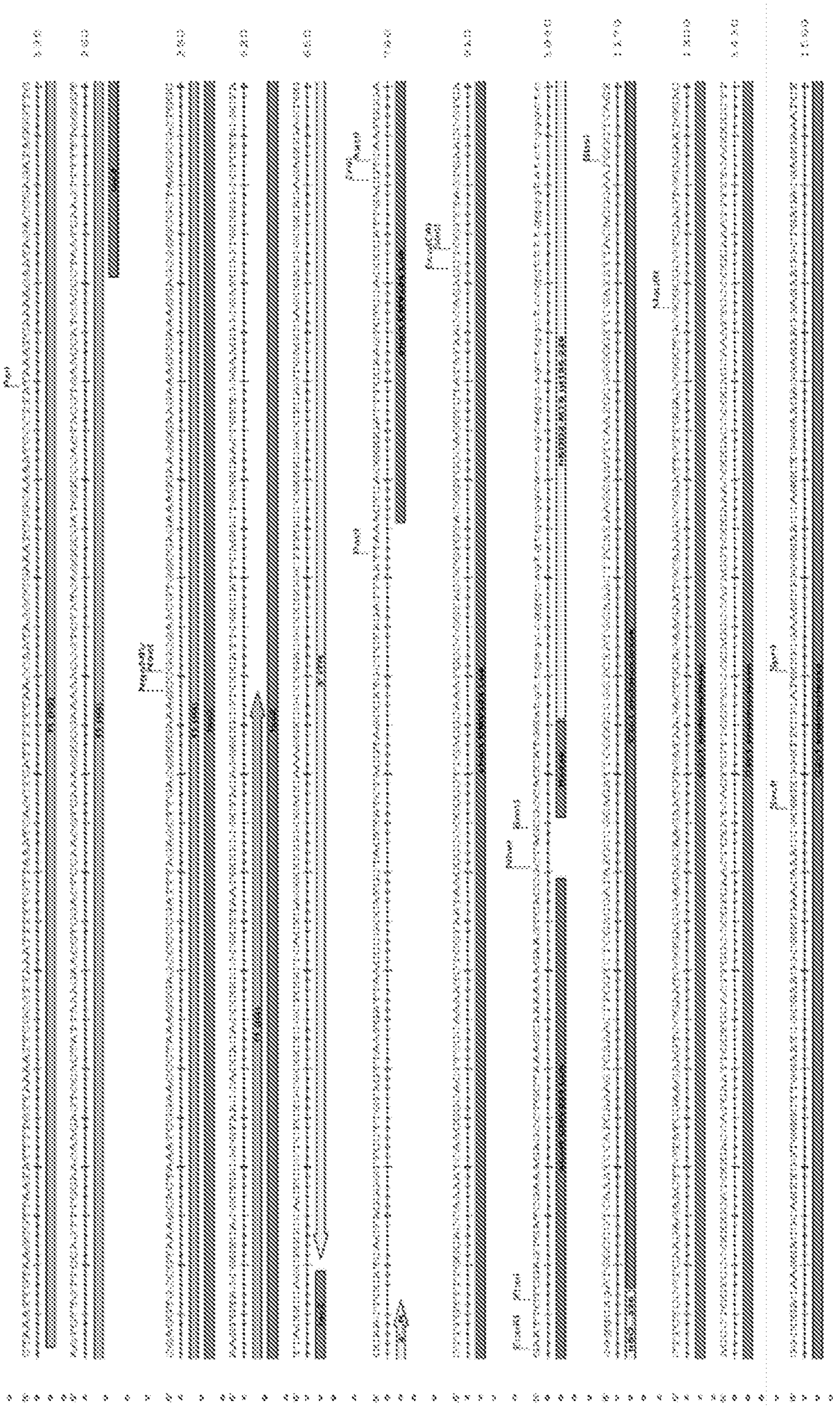
FIG. 19A-19D. Annotation of SEQ ID NO.: 33.
Figure 19B:
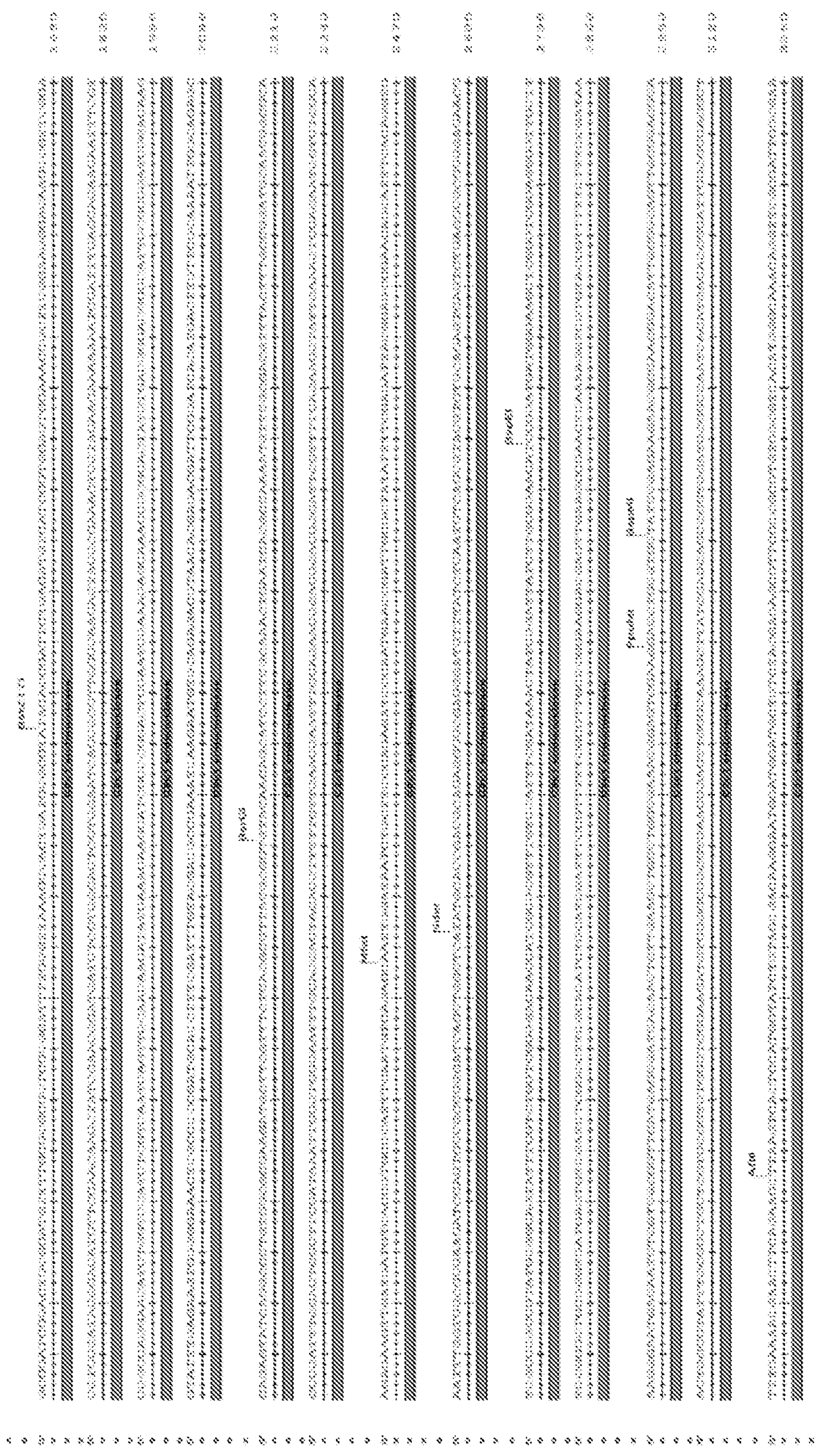
Figure 19C:
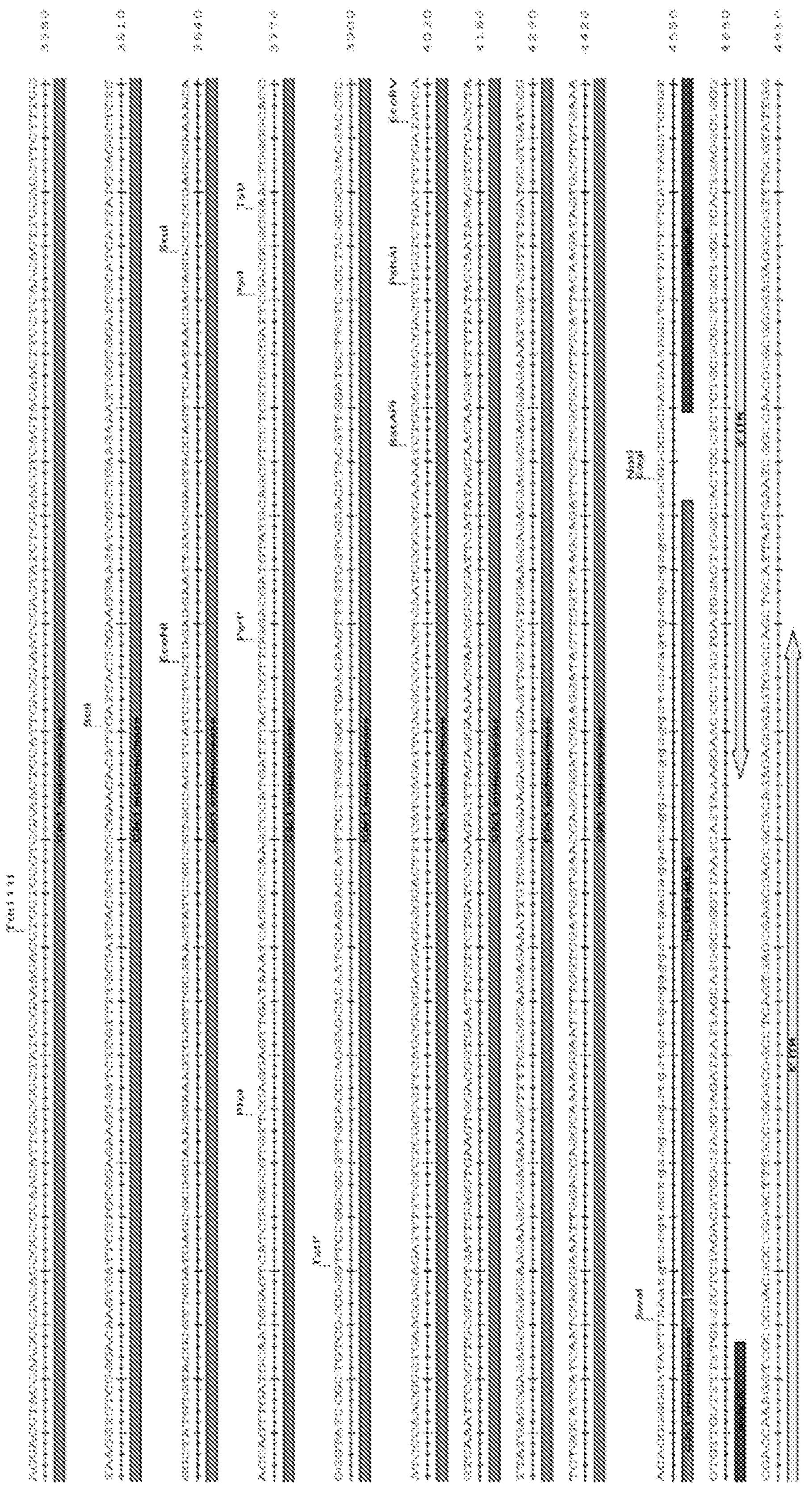
Figure 19D:
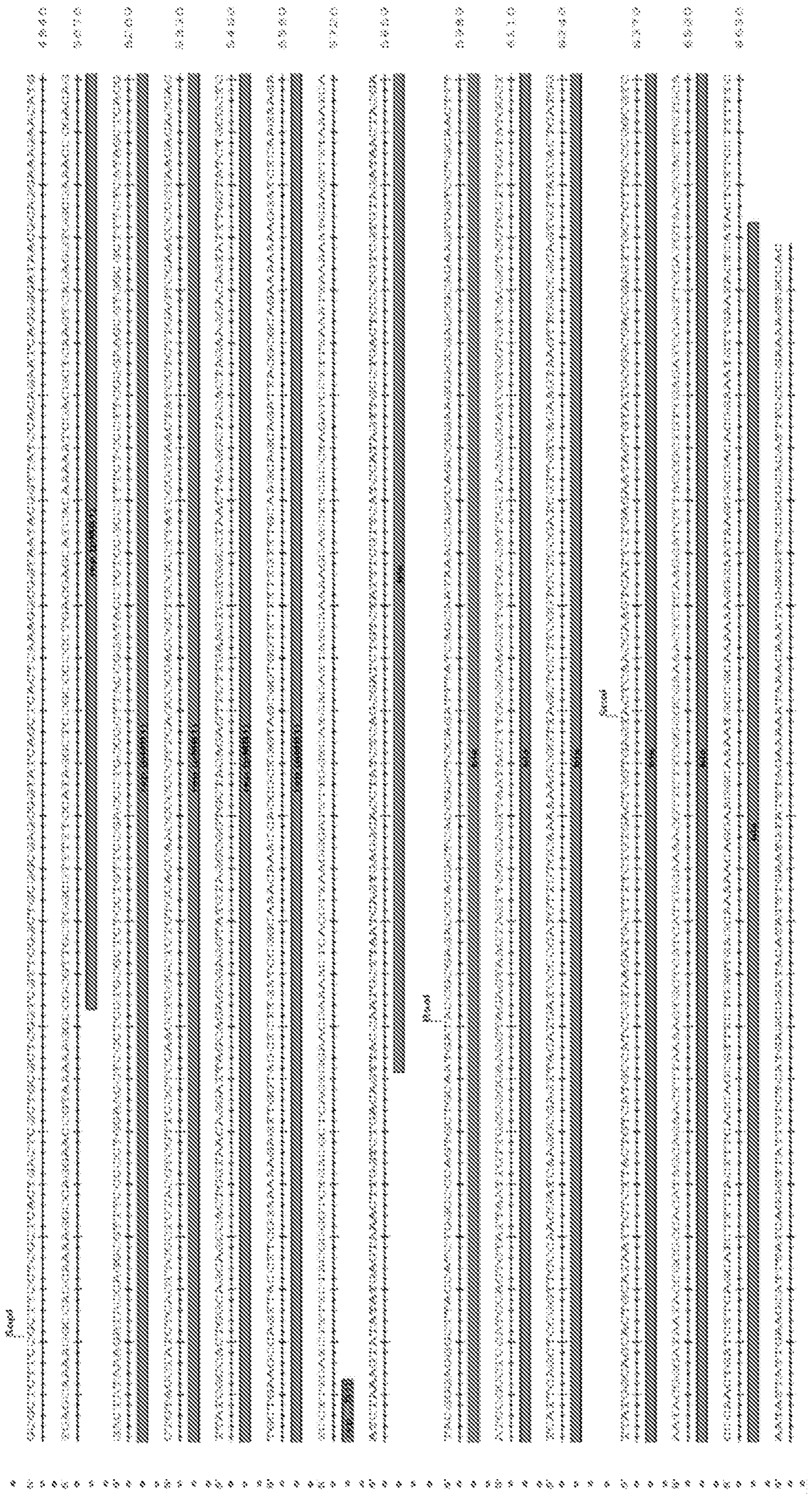
Figure 20A:
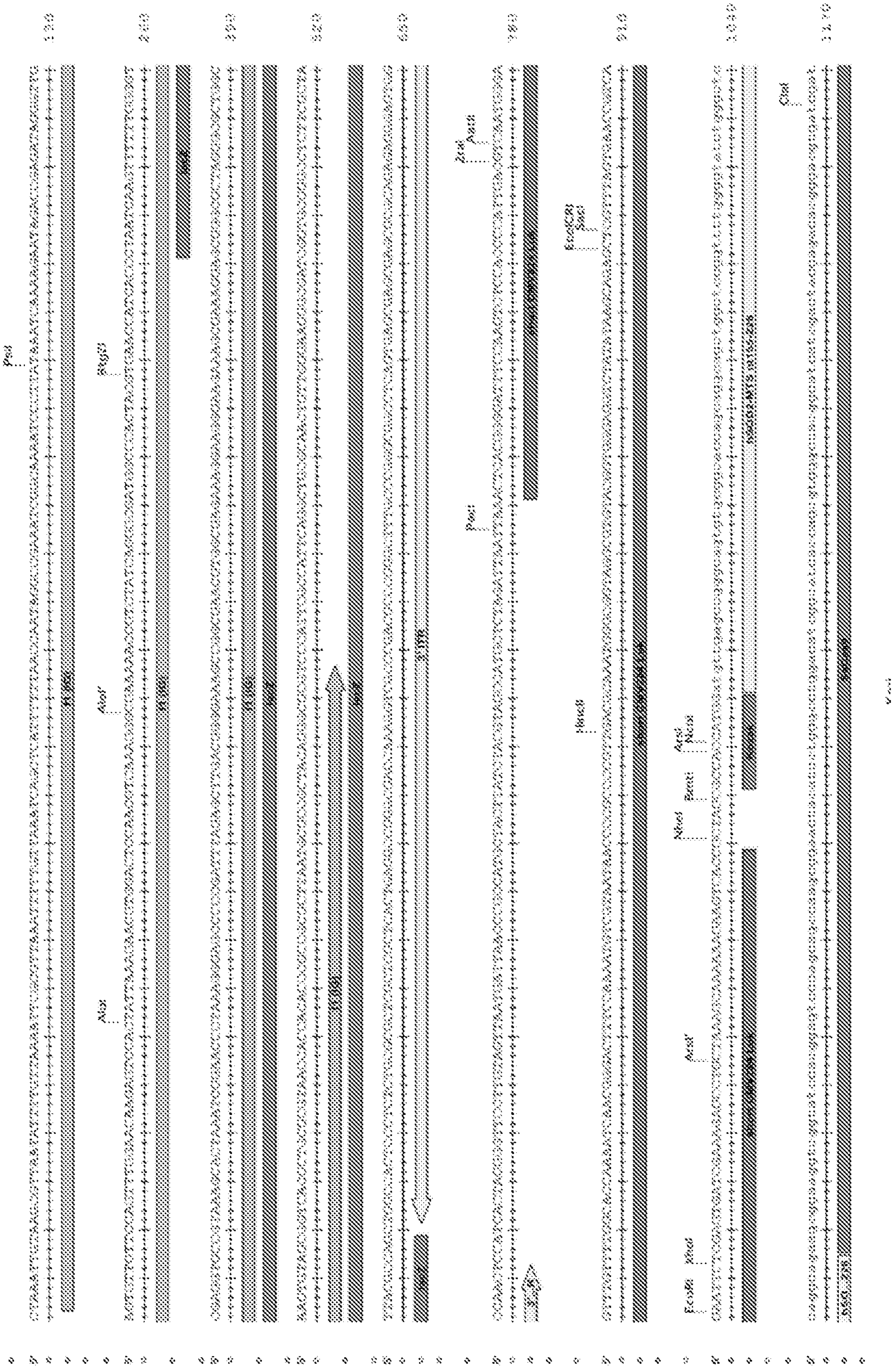
FIG. 20A-20E. Annotation of SEQ ID NO.: 34.
Figure 20B:
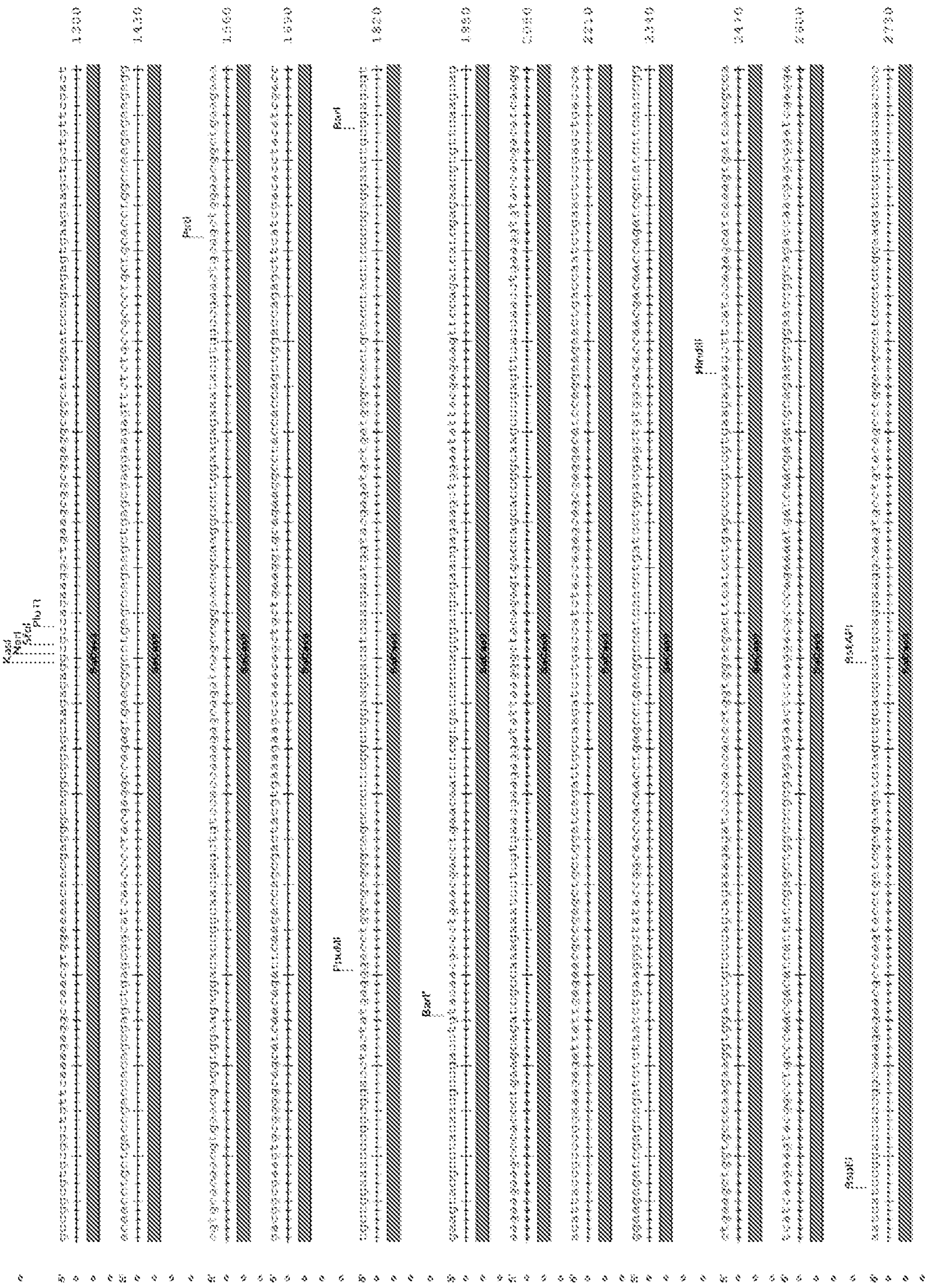
Figure 20C:
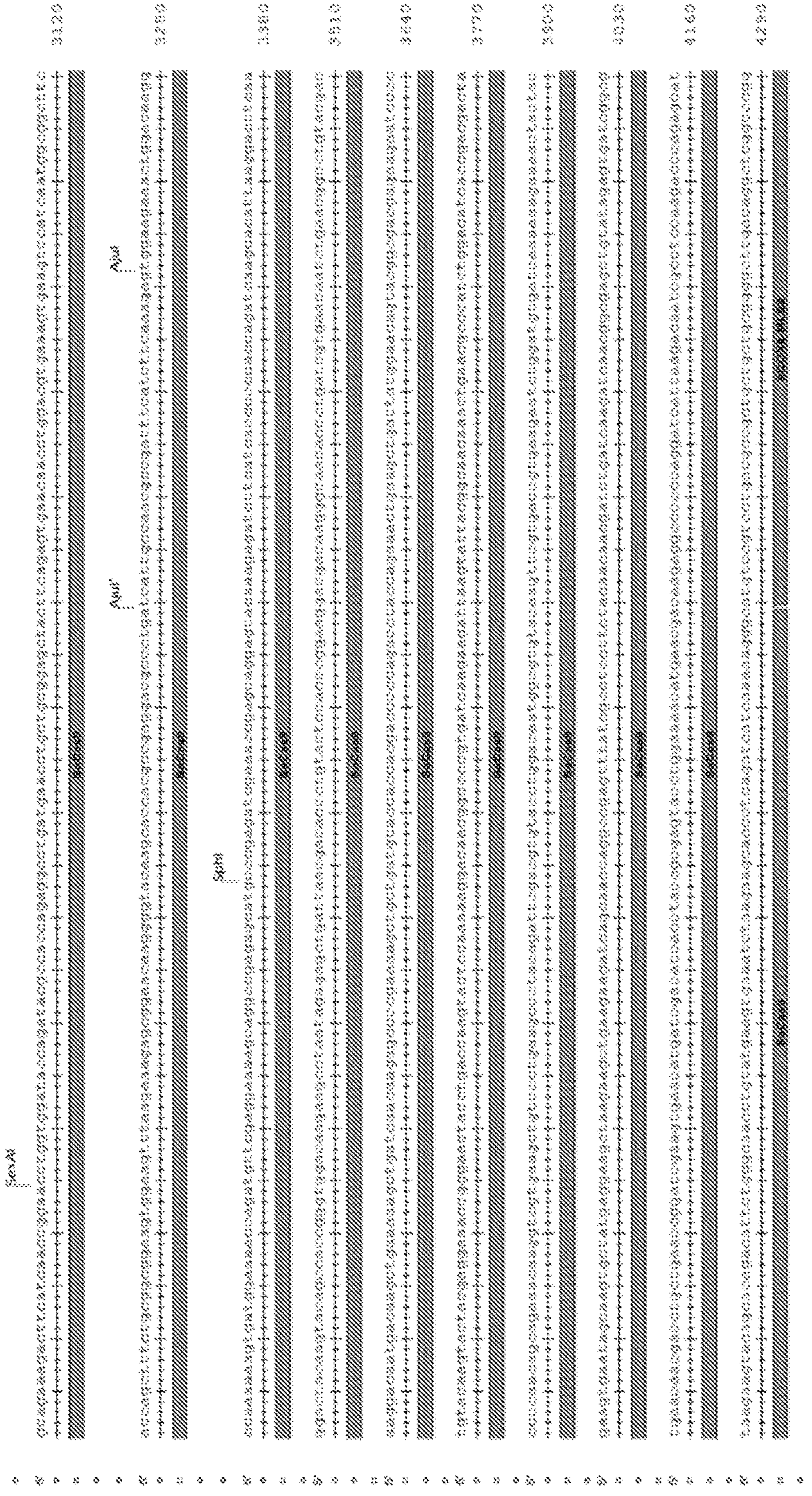
Figure 20D:
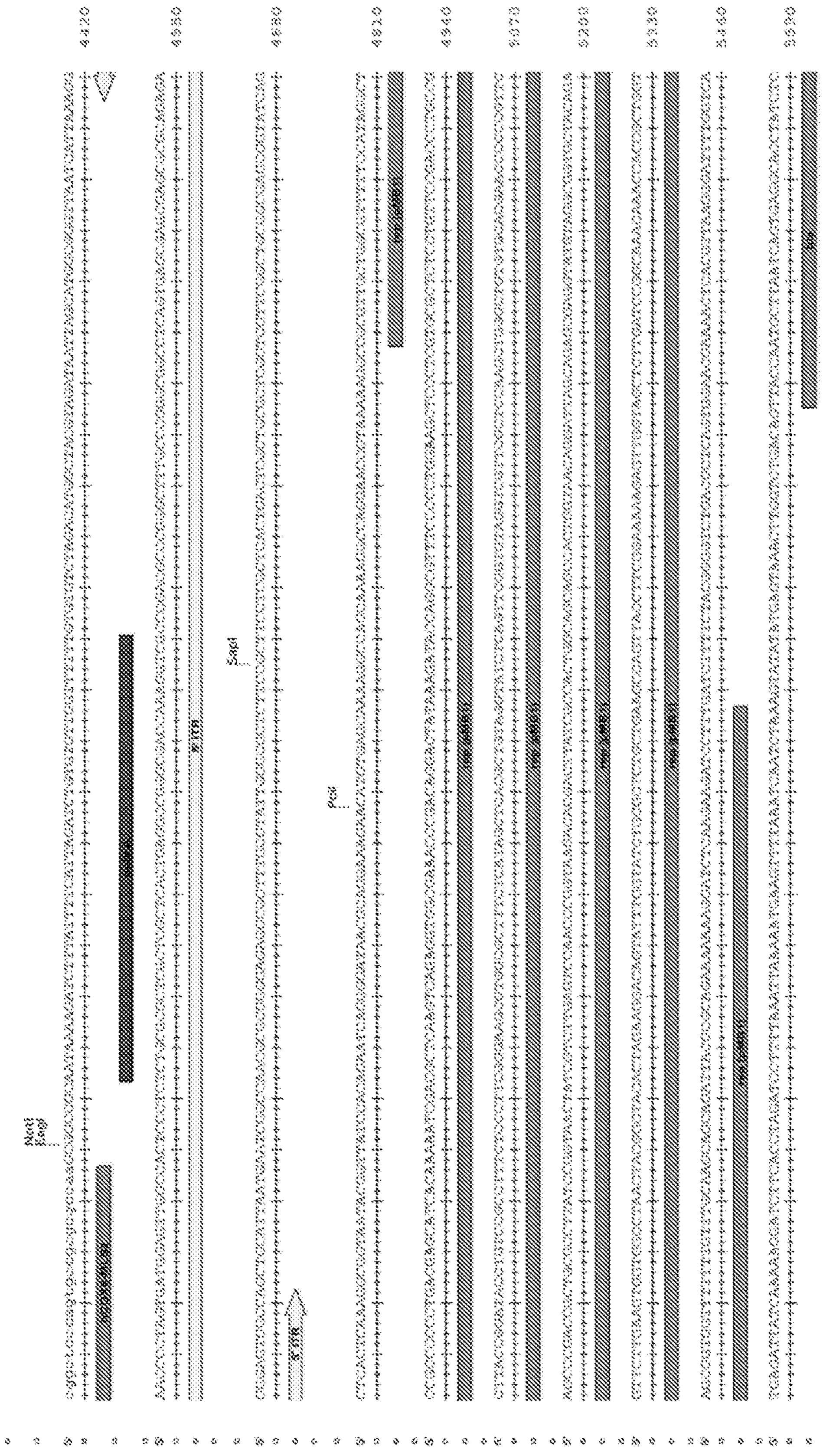
Figure 20E:
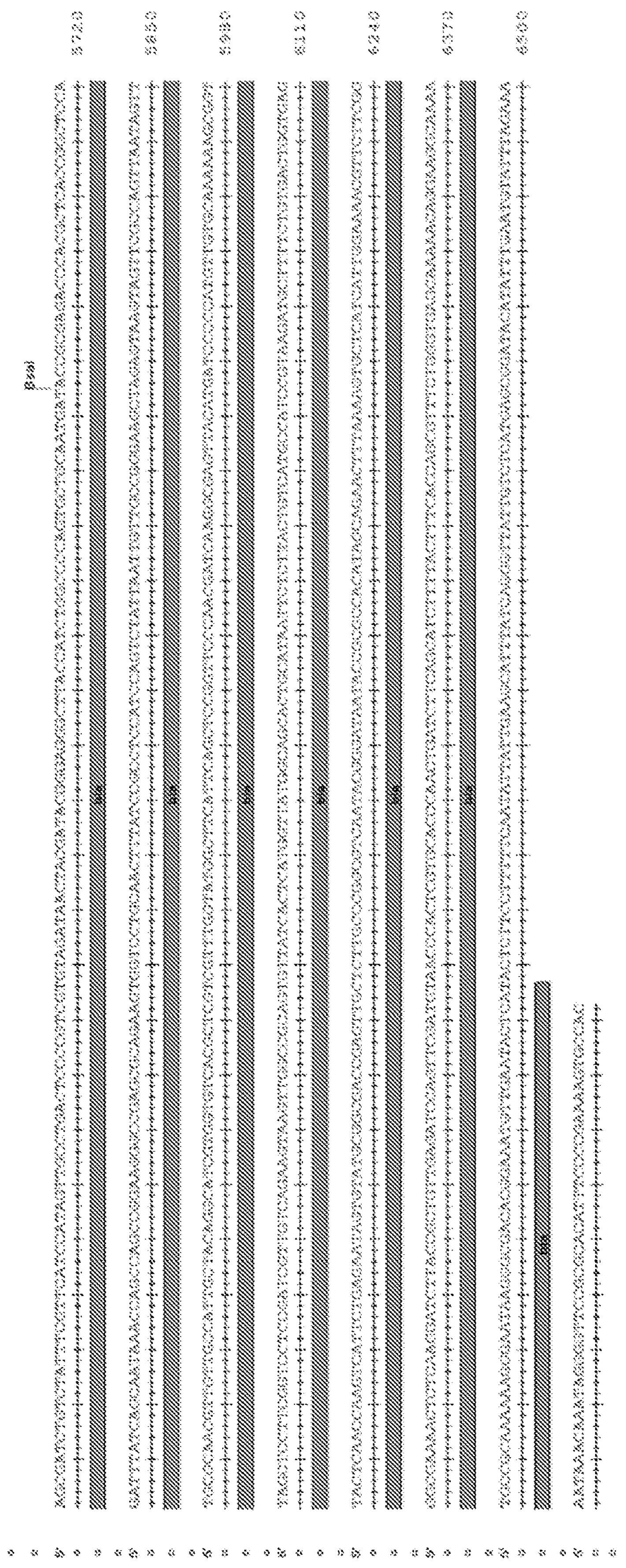

The advantage of using SaCas9 (3,288kb) is that the size is smaller than SpCas9 (4.1 kb) therefore, it is feasible to package in AAV vector with flexibility of type of promoters and other sequences that can be selected. There is a size limit of ~4.8 Kb for packaging in AAV vector. Moreover, the PAM sequence for spCas9 guideRNA limits potential target sequences. On the other hand the PAM sequence for SaCa9 is NNGRRT where (N=A, T, G, G and R=G, A) (SEQ ID NO.: 14). Lastly since SaCas9 is ~1.0 kb smaller than SpCas9 allowing both Cas9 and SgRNA to be packaged in one AAV vector for efficient delivery. An exemplary sgRNA with Scaffold sequence that is compatible with SaCas9 is provided as SEQ ID NO.: 15. Examples of AAV vectors with both SaCa9 and sgRNA are available through Addgene (FIG. 14, Ran, F. A. et al. *In vivo genome editing using Staphylococcus aureus Cas9*. Nature 520, 186-191 (2015)). A nonlimiting, exemplary sequence of an AAV vector comprising MLS modified SaCas9 (pAAV-dCMV-MLS_SaCas9) is provided as SEQ ID NO.: 34.

Endonuclease from *Prevotella* and *Francisella* (Cpf1)

This is another RNA guided endonuclease of class II CRISPR systems. The advantage of using CRISPR/Cpf1 system is that the PAM recognition sequence at 5' end is TTN (SEQ ID NO.: 16) as compared to Cas9 recognition sequence 3'-NGG (SEQ ID NO.: 17). This expands the number of sites that can be targeted. Examples of the target for CRISPR/Cpfi system: Mitochondrial DNA in two mouse strains (C57Bl/6 and NZM) with polymorphism. Multiple targets in the two strains can be knocked down with Cpf1 based CRISPR Cas System by making chimeric guide RNA with RP-loop for delivery into mitochondria. A nonlimiting, exemplary sequence of an AAV vector comprising MLS modified Cpf1 (pAAV-dCMV-MLS_Cpf1) is provided as SEQ ID NO.: 32.

Polymorphisms that can be discretely targeted by CRISPR/Cpf1 system in C57Bl/6 or NZM mice (Zetsche, Bernd, et al. "Cpf1 is a single RNA-guided endonuclease of a class 2 CRISPR-Cas system." *Cell* (2015)):

| Polymorphism (Bolded Nucleotide) | | | |
|---|---|---|---|
| Location | Variant | PAM | Target strain |
| 2201 | T > C | T**T**T | Bl6 |
| 2814 | T > C | **T**TA | Bl6 |
| 3194 | T > C | T**T**A | BL6 |
| 3422 | T > C | T**T**A | Bl6 |
| 4123 | C > T | T **C/T** C | NZM |
| 5552 | T > C | TTG | Bl6 |
| 6041 | T > C | TT**T** | Bl6 |
| 6407 | C > T | **C/T**TC | NZM |
| 6575 | C > T | T **C/t** A | NZM |
| 8467 | T > C | **T**TA | Bl6 |
| 8568 | C > T | TT**C/t** | NZM |
| 8858 | T > C | TT**C** | Bl6 |
| 8864 | C > T | TT**C/T** | NZM |

*Alicyclobacillus Acideoterrestris* Endonuclease (C2c1)

C2c1 is another class II type V endonuclease which has similar cleavage properties as Cpf1 but is distinct from Cas9. It also recognizes the same PAM sequence, TTN, at the 5' end as Cpf1. However, the variation is in the guide RNA scaffold as C2c1 requires both crRNA and tracrRNA for DNA cleavage while Cpf1 is a single-RNA-guided nuclease.

The major advantage over Cpf1 is higher sensitivity to single-nucleotide mismatches between guide RNA and target DNA. Therefore, this makes the CRISPR/C2c1 system least amenable to off-target cleavage. See, e.g., Liu et al. (2017) Molecular Cell 65(2): p310-22; Shmakov S, et al. Mol Cell. (2015) 60:385-97. A nonlimiting, exemplary sequence of an AAV vector comprising MLS modified C2c1 (pAAV-dCMV-MLS_C2c1) is provided as SEQ ID NO.: 33.

EXAMPLE 4

Non-Viral Delivery of CRISPR System

In addition to viral vector based delivery which is an efficient method of choice for in vivo delivery, a non-viral based delivery system may be used as an alternative. AAV based delivery has a packaging size limitation and risks triggering potential an immune response. Furthermore, extended expression of endonucleases which may be caused by viral delivery can cause DNA damage. Recent studies have used lipid nanoparticles for systemic delivery and cutting of target DNA by Cas9 mRNA coupled with AAV particles carrying guideRNA.

Due to the anionic nature of Cas9 mRNA and plasmid DNA, it is feasible to integrate either mRNA or DNA for a Cas9-gRNA complex into anionic liposomes.

For this approach, a lipid-like material, C12-200 that has been shown to be effective in delivering mRNA in primates and rodents will be used to make the liposome as described in Yin et al. (2016) Nat Biotechnol.; 34(3): 328-33. In addition to making complexes of liposome:endonuclease (Cas9 or Cpf1, C2c1) mRNA, a linear rAAV Cas9 plasmid may be used for complex with liposome. Liposomes with Cas9 with viral terminal repeats (ITRs) is more stable and induce transgene expression with similar efficacy to AAV based transduction. See, e.g. U.S. Pat. No. 5,834,441; Yin et al (2016). In some embodiments, an sgRNA and optionally a repair template can be delivered by AAV vector with the liposomes.

Unless defined otherwise, all technical and scientific terms used herein have the same meanings as commonly understood by one of ordinary skill in the art to which this technology belongs. Although exemplary methods, devices and materials are described herein, any methods and materials similar or equivalent to those expressly described herein can be used in the practice or testing of the present technology.

REFERENCES

1. Hsu P D, Lander E S, Zhang F. 2014. Development and applications of CRISPR-Cas9 for genome engineering. Cell 157: 1262-1278.
2. Bacman S R, Williams S L, Pinto M, Peralta S, Moraes C T. Specific elimination of mutant mitochondrial genomes in patient-derived cells by mitoTALENs. Nature Medicine. 2013; 19(9):1111-1113.
3. Gammage P A, Rorbach J, Vincent A I, Rebar E J, Minczuk M. Mitochondrially targeted ZFNs for selective degradation of pathogenic mitochondrial genomes bearing large-scale deletions or point mutations. EMBO Molecular Medicine. 2014; 6(4):458-466.
4. Jo A, Ham S, Lee G H, et al. Efficient Mitochondrial Genome Editing by CRISPR/Cas9. 2015. BioMed Research International. 2015:305716.
5. Moser R, Hirsch M. 2016. AAV Vectorization of DSB-mediated Gene Editing Technologies. Curr Gene Ther. 16(3): 2017-19.
6. Reddy P, Ocampo A, Suzuki K, et al. 2015. Selective elimination of mitochondrial mutations in the germline by genome editing. Cell. 161(3):459-469.
7. Wang G, Chen H W, Oktay Y, Zhang J, Allen E L, Smith G M, Fan K C, Hong J S, French S W, McCaffery J M, Lightowlers R N, Morse H C 3rd, Koehler C M, Teitell M A. 2010. PNPASE regulates RNA import into mitochondria. Cell 142: 456-467.
8. Zetsche B, Volz S, Zhang F. 2015. A split-Cas9 architecture for inducible genome editing and transcription modulation. Nat Biotechnol. 33(2): 139-42.
9. Bacman, S. R., Williams, S. L., Pinto, M. and Moraes, C. T. (2014). The use of mitochondria-targeted endonucleases to manipulate mtDNA. Methods Enzymol 547, 373-397.
10. Bacman, S. R., Williams, S. L., Pinto, M., Peralta, S. and Moraes, C. T. (2013). Specific elimination of mutant mitochondrial genomes in patient-derived cells by mitoTALENs. Nat Med 19, 1111-1113.
11. Comte, C., Tonin, Y., Heckel-Mager, A. M., Boucheham, A., Smirnov, A., Aure, K., Lombes, A., Martin, R. P., Entelis, N. and Tarassov, I. (2013). Mitochondrial targeting of recombinant RNAs modulates the level of a heteroplasmic mutation in human mitochondrial DNA associated with Kearns Sayre Syndrome. Nucleic Acids Res 41, 418-433.
12. Cong, L., Ran, F. A., Cox, D., Lin, S., Barretto, R., Habib, N., Hsu, P. D., Wu, X., Jiang, W., Marraffini, L. A. et al. (2013). Multiplex genome engineering using CRISPR/Cas systems. Science 339, 819-823.
13. Craven, L., Tuppen, H. A., Greggains, G. D., Harbottle, S. J., Murphy, J. L., Cree, L. M., Murdoch, A. P., Chinnery, P. F., Taylor, R. W., Lightowlers, R. N. et al. (2010). Pronuclear transfer in human embryos to prevent transmission of mitochondrial DNA disease. Nature 465, 82-85.
14. Dhillon, V. S. and Fenech, M. (2014). Mutations that affect mitochondrial functions and their association with neurodegenerative diseases. Mutat Res Rev Mutat Res 759, 1-13.
15. Diot, A., Dombi, E., Lodge, T., Liao, C., Morten, K., Carver, J., Wells, D., Child, T., Johnston, I. G., Williams, S. et al. (2016). Modulating mitochondrial quality in disease transmission: towards enabling mitochondrial DNA disease carriers to have healthy children. Biochem Soc Trans 44, 1091-1100.
16. Elliott, H. R., Samuels, D. C., Eden, J. A., Relton, C. L. and Chinnery, P. F. (2008). Pathogenic mitochondrial DNA mutations are common in the general population. Am J Hum Genet 83, 254-260.
17. Fayzulin, R. Z., Perez, M., Kozhukhar, N., Spadafora, D., Wilson, G. L. and Alexeyev, M. F. (2015). A method for mutagenesis of mouse mtDNA and a resource of mouse mtDNA mutations for modeling human pathological conditions. Nucleic Acids Res 43, e62.
18. Gammage, P. A., Gaude, E., Van Haute, L., Rebelo-Guiomar, P., Jackson, C. B., Rorbach, J., Pekalski, M. L., Robinson, A. J., Charpentier, M., Concordet, J. P. et al. (2016a). Near-complete elimination of mutant mtDNA by iterative or dynamic dose-controlled treatment with mtZFNs. Nucleic Acids Res 44, 7804-7816.
19. Gammage, P. A., Rorbach, J., Vincent, A. I., Rebar, E. J. and Minczuk, M. (2014). Mitochondrially targeted ZFNs for selective degradation of pathogenic mitochondrial genomes bearing large-scale deletions or point mutations. EMBO Mol Med 6, 458-466.

20. Gammage, P. A., Van Haute, L. and Minczuk, M. (2016b). Engineered mtZFNs for Manipulation of Human Mitochondrial DNA Heteroplasmy. Methods Mol Biol 1351, 145-162.
21. Hashimoto, M., Bacman, S. R., Peralta, S., Falk, M. J., Chomyn, A., Chan, D. C., Williams, S. L. and Moraes, C. T. (2015). MitoTALEN: A General Approach to Reduce Mutant mtDNA Loads and Restore Oxidative Phosphorylation Function in Mitochondrial Diseases. Mol Ther 23, 1592-1599.
22. Jo, A., Ham, S., Lee, G. H., Lee, Y. I., Kim, S., Lee, Y. S., Shin, J. H. and Lee, Y. (2015). Efficient Mitochondrial Genome Editing by CRISPR/Cas9. Biomed Res Int 2015, 305716.
23. Johnston, I. G., Burgstaller, J. P., Havlicek, V., Kolbe, T., Rülicke, T., Brem, G., Poulton, J. and Jones, N. S. (2015). Stochastic modelling, Bayesian inference, and new in vivo measurements elucidate the debated mtDNA bottleneck mechanism. Elife 4, e07464.
24. Kang, E., Wu, J., Gutierrez, N. M., Koski, A., Tippner-Hedges, R., Agaronyan, K., Platero-Luengo, A., Martinez-Redondo, P., Ma, H., Lee, Y. et al. (2016). Mitochondrial replacement in human oocytes carrying pathogenic mitochondrial DNA mutations. Nature
25. Lightowlers, R. N., Taylor, R. W. and Turnbull, D. M. (2015). Mutations causing mitochondrial disease: What is new and what challenges remain. Science 349, 1494-1499.
26. Manwaring, N., Jones, M. M., Wang, J. J., Rochtchina, E., Howard, C., Mitchell, P. and Sue, C. M. (2007). Population prevalence of the MELAS A3243G mutation. Mitochondrion 7, 230-233.
27. Patananan, A. N., Wu, T. H., Chiou, P. Y. and Teitell, M. A. (2016). Modifying the Mitochondrial Genome. Cell Metab 23, 785-796.
28. Pyle, A., Hudson, G., Wilson, I. J., Coxhead, J., Smertenko, T., Herbert, M., Santibanez-Koref, M. and Chinnery, P. F. (2015). Extreme-Depth Re-sequencing of Mitochondrial DNA Finds No Evidence of Paternal Transmission in Humans. PLoS Genet 11, e1005040.
29. Reddy, P., Ocampo, A., Suzuki, K., Luo, J., Bacman, S. R., Williams, S. L., Sugawara, A., Okamura, D., Tsunekawa, Y., Wu, J. et al. (2015). Selective elimination of mitochondrial mutations in the germline by genome editing. Cell 161, 459-469.
30. Seibel, P., Trappe, J., Villani, G., Klopstock, T., Papa, S. and Reichmann, H. (1995). Transfection of mitochondria: strategy towards a gene therapy of mitochondrial DNA diseases. Nucleic Acids Res 23, 10-17.
31. Wallace, D. C. (2010). Mitochondrial DNA mutations in disease and aging. Environ Mol Mutagen 51, 440-450.
32. Wallace, D. C. and Chalkia, D. (2013). Mitochondrial DNA genetics and the heteroplasmy conundrum in evolution and disease. Cold Spring Harb Perspect Biol 5, a021220.
33. Wang, G., Chen, H. W., Oktay, Y., Zhang, J., Allen, E. L., Smith, G. M., Fan, K. C., Hong, J. S., French, S. W., McCaffery, J. M. et al. (2010). PNPASE regulates RNA import into mitochondria. Cell 142, 456-467.
34. Wang, H., La Russa, M. and Qi, L. S. (2016). CRISPR/Cas9 in Genome Editing and Beyond. Annu Rev Biochem 85, 227-264.
35. Weninger, A., Hatzl, A. M., Schmid, C., Vogl, T. and Glieder, A. (2016). Combinatorial optimization of CRISPR/Cas9 expression enables precision genome engineering in the methylotrophic yeast Pichia pastoris. J Biotechnol
36. Wolf, D. P., Mitalipov, N. and Mitalipov, S. (2015). Mitochondrial replacement therapy in reproductive medicine. Trends Mol Med 21, 68-76.
37. Yamada, M., Emmanuele, V., Sanchez-Quintero, M. J., Sun, B., Lallos, G., Paull, D., Zimmer, M., Pagett, S., Prosser, R. W., Sauer, M. V. et al. (2016). Genetic Drift Can Compromise Mitochondrial Replacement by Nuclear Transfer in Human Oocytes. Cell Stem Cell 18, 749-754.
38. Zuker, M. (2003). Mfold web server for nucleic acid folding and hybridization prediction. Nucleic Acids Res 31, 3406-3415.
39. Shmakov S., Abudayyeh O. O., Makarova K. S., Wolf Y. I., Gootenberg J. S., Semenova E., Minakhin L., Joung J., Konermann S., Severinov K., Zhang F., Koonin E. V. Discovery and functional characterization of diverse class 2 CRISPR-Cas systems. Mol. Cell 60:385-397(2015)

PARTIAL SEQUENCE LISTING

A description of the non-limiting exemplary effectors and the sequences thereof discussed herein is provided below:

```
RP Loop (DNA) (SEQ ID NO.: 1)
TCTCCCTGAGCTTCAGGGAG

RP Loop (RNA) (SEQ ID NO.: 2)
UCUCCCUGAGCUUCAGGGAG

MRP Loop (DNA) (SEQ ID NO.: 3)
AGAAGCGTATCCCGCTGAGC

MRP Loop (RNA) (SEQ ID NO.: 4)
AGAAGCGUAUCCCGCUGAGC

Spacer (SEQ ID NO.: 5)
ttaattaa

Hybrid Guide RNA Template (SEQ ID NO.: 6)
TCTCCCTGAGCTTCAGGGAGttaattaaNNNNNNNNNNNNNNNNNNNNgttttagagctaG
AAAtagcaagttaaaataaggctagtccgttatcaacttgaaaaagtggcaccgagtcggtgcTTTTTT

Hybrid Guide RNA for mtND4 Target (SEQ ID NO.: 7)
TCTCCCTGAGCTTCAGGGAGttaattaaCGTACTATAATCATGGCCCGgttttagagctaGA
AAtagcaagttaaaataaggctagtccgttatcaacttgaaaaagtggcaccgagtcggtgcTTTTTT
```

-continued pX-U6-RP-sgRNA-MLS-mSpCas9 system construct (SEQ ID NO.: 8)
gagggcctatacccatgattccacatatagcatatacgatacaaggctgaagagagataattggaattaatttgactgtaaacaca
aagatattagtacaaaatacgtgacgtagaaagtaataatacagggtagtagcagattaaaattatgattaaaatggactatcatat
gcttaccgtaacttgaaagtatacgatttcaggcatatatatcaGTGGAAAGGACGAAACACCgTCTCCC
TGAGCTTCAGGGAGttaattaaNNNNNNNNNNNNNNNNNNNgattagagctaGAAAtagca
agttaaaataaggctagtccgttatcaacttgaaaaagtggcaccgagtcggtgcTTTTTTgattagagctagaaatagcaa
gttaaaataaggctagtccgtTTTTagcgcgtgcgccaattctgcagacaaatggctctagaggtacccgttacataacttacg
gtaaatggcccgcctggctgaccgcccaacgacccccgcccattgacgtcaatagtaacgccaatagggactaccattgacgt
caatgggtggagtatttacggtaaactgcccacaggcagtacatcaagtgtatcatatgccaagtacgccccctattgacgtcaat
gacggtaaatggcccgcctggcattGtgcccagtacatgaccttatgggactacctacaggcagtacatctacgtattagtcatc
gctattaccatggtcgaggtgagccccacgactgcttcactctccccatctcccccccctccccacccccaattagtatttatttattt
ataattattagtgcagcgatgggggcgggggggggggggggcgcgcgccaggcggggcggggcggggcgaggggcg
gggcggggcgaggcggagaggtgcggcggcagccaatcagagcggcgcgctccgaaagtttccttttatggcgaggcggc
ggcggcggcggccctataaaaagcgaagcgcgcggcgggcgggagtcgctgcgacgctgccttcgccccgtgccccgctc
cgccgccgcctcgcgccgcccgccccggctctgactgaccgcgttactcccacaggtgagcgggcgggacggcccttctcct
ccgggctgtaattagctgagcaagaggtaagggtttaagggatggttggttggtggggtattaatgtttaattacctggagcacctg
cctgaaatcactttttttcaggttGGACCGGTGCCACCATGTACCCATACGATGTTCCAGATT
ACGCTCGCGAATGCTGTCTAATTTGAGGATCCTGCTCAACAATGCAGCTCTTA
GAAAGGGTCACACTTCTGTGGTTCGACATTTTTGGTGTGGGAAGCCAGTCCAA
AGTCAAGTACAGCTGAAAGGCCGTGACCTCCTCACCTTGTCGCGAGACAAGA
AATATTCTATCGGCCTGGATATTGGAACTAACAGTGTGGGCTGGGCCGTCATC
ACCGACGAGTACAAAGTGCCAAGCAAGAAGTTCAAGGTCCTGGGAAACACC
GATAGACACAGCATCAAGAAAAATCTGATTGGGGCCCTGCTCTTCGACTCCG
GCGAGACAGCTGAAGCAACTAGGCTGAAAAGAACAGCTAGGAGACGGTATA
CTCGCCGAAAGAATCGGATCTGCTACCTGCAGGAGATTTTCAGCAACGAAAT
GGCCAAGGTGGACGATAGTTTCTTTCACAGGCTGGAGGAATCATTCCTGGTCG
AGGAAGATAAGAAACACGAGAGGCATCCCATCTTTGGCAACATTGTGGACGA
GGTCGCTTATCACGAAAAGTACCCTACAATCTATCATCTCAGGAAGAAACTG
GTGGACAGCACTGATAAGGCAGACCTGAGACTCATCTATCTGGCCCTCGCTC
ACATGATTAAGTTCCGGGGCCATTTTCTCATCGAGGGAGATCTGAACCCAGAC
AATTCCGATGTGGACAAGCTCTTCATCCAGCTGGTCCAGACATACAATCAGCT
GTTTGAGGAAAACCCCATTAATGCATCAGGCGTGGACGCAAAAGCCATCCTC
AGCGCCAGACTGTCTAAGAGTAGGAGACTGGAGAACCTCATCGCTCAGCTGC
CAGGCGAAAAGAAAAACGGGCTCTTTGGTAATCTGATTGCACTGTCCCTCGG
ACTGACCCCCAACTTCAAGTCTAATTTTGATCTGGCCGAGGACGCTAAACTCC
AGCTGAGCAAGGACACATATGACGATGACCTGGATAACCTGCTCGCTCAGAT
CGGAGATCAGTACGCAGACCTCTTCCTGGCCGCTAAGAATCTGTCTGACGCCA
TCCTGCTCAGTGATATTCTGAGGGTGAACACCGAGATTACAAAAGCCCCCCTG
TCAGCTAGCATGATCAAGAGATATGACGAGCACCATCAGGATCTGACCCTGC
TCAAGGCTCTCGTGCGGCAGCAGCTGCCTGAGAAGTACAAAGAAATCTTCTTT
GATCAGTCTAAGAACGGCTACGCCGGATATATTGACGGCGGAGCTAGTCAGG
AGGAGTTCTACAAGTTTATCAAACCCATTCTGGAGAAGATGGACGGGACTGA
GGAACTGCTCGTGAAACTGAATAGAGAGGACCTGCTCCGGAAGCAGCGCACC
TTCGATAACGGCTCCATCCCTCACCAGATTCATCTGGGAGAGCTCCACGCAAT
CCTGCGGCGCCAGGAGGACTTCTACCCATTTCTGAAGGATAACCGGGAGAAG
ATCGAAAAAATTCTGACTTTCCGCATCCCCTACTATGTGGGGCCTCTGGCAAG
AGGTAATAGTCGGTTTGCCTGGATGACCCGCAAGTCAGAGGAAACAATCACT
CCCTGGAACTTCGAGGAAGTGGTCGATAAGGGAGCTTCCGCACAGTCTTTCAT
TGAGAGGATGACAAATTTTGACAAGAACCTCCCAAATGAAAAAGTGCTGCCC
AAGCACTCTCTGCTCTACGAGTATTTCACCGTCTATAACGAACTGACAAAGGT
GAAATACGTCACTGAGGGGATGAGAAAGCCTGCCTTCCTGAGTGGTGAACAG
AAGAAAGCTATCGTGGACCTGCTCTTTAAAACCAATCGGAAGGTGACAGTCA
AGCAGCTGAAAGAGGACTATTTCAAGAAAATTGAATGTTTCGATTCTGTGGA
GATCAGTGGCGTCGAGGACAGGTTCAACGCCTCCCTGGGAACCTACCACGAT
CTGCTCAAGATCATTAAGGATAAAGACTTCCTCGACAACGAGGAAAATGAGG
ATATCCTGGAGGACATTGTGCTCACCCTGACACTCTTTGAGGATCGGGAAATG
ATCGAGGAACGCCTCAAGACATATGCCCATCTGTTCGATGACAAAGTGATGA
AACAGCTGAAGCGAAGGAGATACACTGGGTGGGGTCGACTCTCTAGGAAGCT
GATCAACGGCATCAGGGACAAACAGAGCGGAAAGACAATCCTGGACTTTCTC
AAGTCCGATGGCTTCGCTAACAGGAACTTCATGCAGCTCATTCACGATGACTC
CCTGACTTTCAAAGAGGATATCCAGAAGGCACAGGTGTCCGGCCAGGGAGAC
TCTCTCCACGAGCATATCGCAAACCTGGCCGGGTCTCCTGCCATCAAGAAAG
GTATTCTGCAGACCGTGAAGGTGGTCGACGAGCTGGTGAAAGTCATGGGGAG
ACATAAGCCAGAAAACATCGTGATTGAGATGGCCAGGGAGAATCAGACCAC
ACAGAAGGGTCAGAAGAACTCACGGGAGCGCATGAAACGGATCGAGGAAGG
CATTAAGGAACTCGGAAGCCAGATCCTGAAGGAGCACCCCGTGGAAAACACA
CAGCTGCAGAATGAGAAGCTGTATCTCTACTATCTGCAGAATGGACGCGATA
TGTACGTGGACCAGGAGCTCGATATTAACCGACTGTCCGATTACGACGTGGA
TCATATCGTCCCACAGTCATTCCTGAAAGATGACAGCATTGACAATAAGGTGC
TGACTCGCTCTGACAAAAACCGAGGGAAGAGTGATAATGTCCCCTCAGAGGA
AGTGGTCAAGAAAATGAAGAACTACTGGAGGCAGCTGCTCAATGCCAAACTG
ATCACCCAGCGAAAGTTTGATAACCTGACAAAAGCTGAGAGGGGGGGTCTGA
GTGAACTCGACAAAGCAGGCTTCATCAAGCGACAGCTGGTGGAGACCAGGCA
GATCACAAAGCACGTCGCTCAGATTCTGGACTCACGCATGAACACCAAGTAC
GATGAGAATGACAAACTGATCCGAGAAGTGAAGGTCATTACACTCAAGTCAA
AACTGGTGAGCGACTTTAGGAAAGATTTCCAGTTTTATAAGGTCAGAGAGAT
CAACAACTACCACCATGCTCATGACGCATACCTGAACGCAGTGGTCGGGACT
GCCCTCATTAAGAAATACCCTAAACTGGAGTCCGAGTTCGTGTACGGTGACTA
TAAGGTGTACGATGTCAGAAAAATGATCGCCAAGTCTGAGCAGGAAATTGGC -continued AAAGCCACCGCTAAGTATTTCTTTTACAGTAACATCATGAATTTCTTTAAGAC
TGAGATCACCCTGGCAAATGGAGAAATCCGAAAGAGGCCACTGATTGAGACT
AACGGGGAGACCGGCGAAATCGTGTGGGACAAAGGGAGAGATTTTGCTACA
GTGCGGAAGGTCCTGAGCATGCCCCAAGTGAATATTGTCAAGAAAACAGAGG
TGCAGACTGGCGGATTCAGTAAGGAATCAATTCTCCCTAAACGCAACTCCGA
TAAGCTGATCGCCCGAAAGAAAGACTGGGATCCTAAGAAATATGGGGGTTTC
GACTCCCCAACCGTGGCTTACTCTGTCCTGGTGGTCGCAAAGGTGGAGAAGG
GGAAAAGCAAGAAACTGAAATCCGTCAAGGAACTGCTCGGTATCACAATTAT
GGAGCGGAGCTCCTTCGAAAAGAATCCTATCGATTTTCTGGAGGCTAAAGGC
TATAAGGAAGTGAAGAAAGACCTCATCATCAAGCTGCCAAAGTACTCACTGT
TTGAGCTCGAAAACGGAAGAAAGCGAATGCTCGCAAGCGCCGGAGAGCTGC
AGAAGGGTAATGAACTGGCCCTCCCCTCCAAGTACGTGAACTTCCTGTATCTC
GCTAGCCACTACGAGAAGCTGAAAGGCTCCCCTGAGGATAACGAACAGAAAC
AGCTGTTTGTGGAGCAGCACAAGCATTATCTGGACGAGATCATTGAACAGAT
TAGCGAGTTCTCCAAACGCGTGATCCTGGCTGACGCAAATCTCGATAAGGTCC
TGTCTGCATACAACAAACACAGGGACAAGCCAATCAGAGAGCAGGCCGAAA
ATATCATTCATCTGTTCACTCTCACCAACCTGGGAGCACCAGCAGCCTTCAAG
TATTTTGACACTACCATCGATCGCAAACGATACACAAGCACTAAGGAGGTGC
TCGACGCTACCCTGATCCACCAGTCTATTACTGGCCTGTACGAGACCCGGATC
GACCTCAGTCAGCTGGGCGGAGATatgtccgtcctgacgccgctgctgctgcggggcttgacaggctcg
gcccggcggctcccagtgccgcgcgccaaCTCGAGAAGAATTCCTAGAGCTCGCTGATCAGC
CTCGACTGTGCCTTCTAGTTGCCAGCCATCTGTTGTTTGCCCCTCCCCCGTGCC
TTCCTTGACCCTGGAAGGTGCCACTCCCACTGTCCTTTCCTAATAAAATGAGG
AAATTGCATCGCATTGTCTGAGTAGGTGTCATTCTATTCTGGGGGGTGGGGTG
GGGCAGGACAGCAAGGGGGAGGATTGGGAAGAgAATAGCAGGCATGCTGGG
GAgcggccgcaggaacccctagtgatggagttggccactccctctctgcgcgctcgctcgctcactgaggccgggcgacca
aaggtcgcccgacgcccgggctttgcccgggcggcctcagtgagcgagcgagcgcgcagctgcctgcaggggcgcctgat
gcggtattttctccttacgcatctgtgcggtatttcacaccgcatacgtcaaagcaaccatagtacgcgccctgtagcggcgcatta
agcgcggcgggtgtggtggttacgcgcagcgtgaccgctacacttgccagcgccctagcgcccgctcctttcgctttcttcccttc
ctttctcgccacgttcgccggctttccccgtcaagctctaaatcgggggctccctttagggttccgatttagtgctttacggcacctc
gaccccaaaaaacttgatttgggtgatggttcacgtagtgggccatcgccctgatagacggtttttcgccctttgacgttggagtcc
acgttctttaatagtggactcttgttccaaactggaacaacactcaaccctatctcgggctattcttttgatttataagggattttgccga
tttcggcctattggttaaaaaatgagctgatttaacaaaaatttaacgcgaattttaacaaaatattaacgtttacaattttatggtgcact
ctcagtacaatctgctctgatgccgcatagttaagccagccccgacacccgccaacacccgctgacgcgccctgacgggcttgt
ctgctcccggcatccgcttacagacaagctgtgaccgtctccgggagctgcatgtgtcagaggttttcaccgtcatcaccgaaac
gcgcgagacgaaagggcctcgtgatacgcctatttttataggttaatgtcatgataataatggtttcttagacgtcaggtggcactttt
cggggaaatgtgcgcggaacccctatttgtttatttttctaaatacattcaaatatgtatccgctcatgagacaataaccctgataaat
gcttcaataatattgaaaaaggaagagtatgagtattcaacatttccgtgtcgcccttattcccttattgcggcattttgccttcctgatt
tgctcacccagaaacgctggtgaaagtaaaagatgctgaagatcagttgggtgcacgagtgggttacatcgaactggatctcaac
agcggtaagatccttgagagttttcgccccgaagaacgttttccaatgatgagcacttttaaagttctgctatgtggcgcggtattatc
ccgtattgacgccgggcaagagcaactcggtcgccgcatacactattctcagaatgacttggttgagtactcaccagtcacagaa
aagcatcttacggatggcatgacagtaagagaattatgcagtgctgccataaccatgagtgataacactgcggccaacttacttct
gacaacgatcggaggaccgaaggagctaaccgcttattgcacaacatgggggatcatgtaactcgccttgatcgttgggaacc
ggagctgaatgaagccataccaaacgacgagcgtgacaccacgatgcctgtagcaatggcaacaacgttgcgcaaactattaa
ctggcgaactacttactctagcttcccggcaacaattaatagactggatggaggcggataaagttgcaggaccacttctgcgctcg
gcccttccggctggctggtttattgctgataaatctggagccggtgagcgtggaagccgcggtatcattgcagcactggggccag
atggtaagccctcccgtatcgtagttatctacacgacggggagtcaggcaactatggatgaacgaaatagacagatcgctgagat
aggtgcctcactgattaagcattggtaactgtcagaccaagtttactcatatatactttagattgatttaaaacttcatttttaatttaaaa
ggatctaggtgaagatcatttttgataatctcatgaccaaaatcccttaacgtgagttttcgttccactgagcgtcagaccccgtaga
aaagatcaaaggatcttcttgagatcctttttttctgcgcgtaatctgctgcttgcaaacaaaaaaaccaccgctaccagcggtggtt
tgtttgccggatcaagagctaccaactctttttccgaaggtaactggcttcagcagagcgcagataccaaatactgtccttctagtgt
agccgtagttaggccaccacttcaagaactctgtagcaccgcctacatacctcgctctgctaatcctgttaccagtggctgctgcca
gtggcgataagtcgtgtcttaccgggttggactcaagacgatagttaccggataaggcgcagcggtcgggctgaacggggggt
tcgtgcacacagcccagcttggagcgaacgacctacaccgaactgagatacctacagcgtgagctatgagaaagcgccacgct
tcccgaagggagaaaggcggacaggtatccggtaagcggcagggtcggaacaggagagcgcacgagggagcttccaggg
ggaaacgcctggtatctttatagtcctgtcgggtttcgccacctctgacttgagcgtcgatttttgtgatgctcgtcaggggggcgg
agcctatggaaaaacgccagcaacgcggcctttttacggttcctggccttttgctggccttttgctcacatgt
Nucleotide:

1-250 Human U6 promoter 251-270 RP loop 279-297 Target specific sequence 298-373 Chimeric guideRNA scaffold 1311-1450 MLS1-OTC 1457-5557 mSpCas9

5558-5631 MLS2-hCox8 scAAV-U6-RP-sgRNA-deltaCMV-eGFP (SEQ ID NO.: 9)
5'CAGCAGCTGCGCGCTCGCTCGCTCACTGAGGCCGCCCGGGCAAAGCCCGGG
CGTCGGGCGACCTTTGGTCGCCCGGCCTCAGTGAGCGAGCGAGCGCGCAGAG
AGGGAGTGGGGTTATCGGCGCGCCAAGGTCGGGCAGGAAGAGGGCCTATTTC
CCATGATTCCTTCATATTTGCATATACGATACAAGGCTGTTAGAGAGATAATT
AGAATTAATTTGACTGTAAACACAAAGATATTAGTACAAAATACGTGACGTA -continued

```
GAAAGTAATAATTTCTTGGGTAGTTTGCAGTTTTTAAAATTATGTTTTAAAAT
GGACTATCATATGCTTACCGTAACTTGAAAGTATTTCGATTTCTTGGCTTTATA
TATCTTGTGGAAAGGACGAAACACCGTCTCCCTGAGCTTCAGGGAGttaattaaNN
NNNNNNNNNNNNNNNNNNgttttagagctaGAAAtagcaagttaaaataaggctagtccgttatcaacttgaa
aaagtggcaccgagtcggtgcTTTTTTcaattgTCGTTACATAACTTACGGTAAATGGCCCGC
CTGGCTGACCGCCCAACGACCCCCGGACTCACGGGGATTTCCAAGTCTCCAC
CCCATTGACGTCAATGGGAGTTTGTTTTGGCACCAAAATCAACGGGACTTTCC
AAAATGTCGTAACAACTCCGCCCCATTGACGCAAATGGGCGGTAGGCGTGTA
CGGTGGGAGGTCTATATAAGCAGAGCTCGTTTAGTGAACCGTCAGATCGCCT
GGAGACGCCATCCACGCTGTTTTGACCTCCATAGAAGACACCGGGACCGATC
CAGCCTCCGGacCTAGAGGATCCGGTACTCGAGGAACTGAAAAACCAGAAAG
TTAACTGGTAAGTTTAGTCTTTTTGTCTTTTATTTCAGGTCCCGGATCCGGTGG
TGGTGCAAATCAAAGAACTGCTCCTCAGTGGATGTTGCCTTTACTTCTAGGCC
TGTACGGAAGTGTTACTTCTGCTCTAAAAGCTGCGGAATTGTACCCctgcagtcgac
ggtaccgcgggcccgggatccaccggtcgccaccATGGTGAGCAAGGGCGAGGAGCTGTTCACC
GGGGTGGTGCCCATCCTGGTCGAGCTGGACGGCGACGTAAACGGCCACAAGT
TCAGCGTGTCCGGCGAGGGCGAGGGCGATGCCACCTACGGCAAGCTGACCCT
GAAGTTCATCTGCACCACCGGCAAGCTGCCCGTGCCCTGGCCCACCCTCGTGA
CCACCCTGACCTACGGCGTGCAGTGCTTCAGCCGCTACCCCGACCACATGAA
GCAGCACGACTTCTTCAAGTCCGCCATGCCCGAAGGCTACGTCCAGGAGCGC
ACCATCTTCTTCAAGGACGACGGCAACTACAAGACCCGCGCCGAGGTGAAGT
TCGAGGGCGACACCCTGGTGAACCGCATCGAGCTGAAGGGCATCGACTTCAA
GGAGGACGGCAACATCCTGGGGCACAAGCTGGAGTACAACTACAACAGCCA
CAACGTCTATATCATGGCCGACAAGCAGAAGAACGGCATCAAGGTGAACTTC
AAGATCCGCCACAACATCGAGGACGGCAGCGTGCAGCTCGCCGACCACTACC
AGCAGAACACCCCCATCGGCGACGGCCCCGTGCTGCTGCCCGACAACCACTA
CCTGAGCACCCAGTCCGCCCTGAGCAAAGACCCCAACGAGAAGCGCGATCAC
ATGGTCCTGCTGGAGTTCGTGACCGCCGCCGGGATCACTCTCGGCATGGACG
AGCTGTACAAGTAAagaggccggccgcggggatCCAGACATGATAAGATACATTGATG
AGTTTGGACAAACCACAACTAGAATGCAGTGAAAAAAATGCTTTATTTGTGA
AATTTGTGATGCTATTGCTTTATTTGTAACCATTATAAGCTGCAATAAACAAG
TTAACAACAACAATTGCAACTAGTGCTAGAAGCATGGCTACGTAGATAAGTA
GCATGGCGGGTTAATCATTAACTACAAGGAACCCCTAGTGATGGAGTTGGCC
ACTCCCTCTCTGCGCGCTCGCTCGCTCACTGAGGCCGGGCGACCAAAGGTCGC
CCGACGCCCGGGCTTTGCCCGGGCGGCCTCAGTGAGCGAGCGAGCGCGCAGC
TGGCGTAATAGCGAAGAGGCCCGCACCGATCGCCCTTCCCAACAGTTGCGCA
GCCTGAATGGCGAATGGcgattccGTTGCAATGGCTGGCGGTAATATTGTTCTGG
ATATTACCAGCAAGGCCGATAGTTTGAGTTCTTCTACTCAGGCAAGTGATGTT
ATTACTAATCAAAGAAGTATTGCGACAACGGTTAATTTGCGTGATGGACAGA
CTCTTTTACTCGGTGGCCTCACTGATTATAAAAACACTTCTCAGGATTCTGGC
GTACCGTTCCTGTCTAAAATCCCTTTAATCGGCCTCCTGTTTAGCTCCCGCTCT
GATTCTAACGAGGAAAGCACGTTATACGTGCTCGTCAAAGCAACCATAGTAC
GCGCCCTGTAGCGGCGCATTAAGCGCGGCGGGTGTGGTGGTTACGCGCAGCG
TGACCGCTACACTTGCCAGCGCCCTAGCGCCCGCTCCTTTCGCTTTCTTCCCTT
CCTTTCTCGCCACGTTCGCCGGCTTTCCCCGTCAAGCTCTAAATCGGGGGCTC
CCTTTAGGGTTCCGATTTAGTGCTTTACGGCACCTCGACCCCAAAAAACTTGA
TTAGGGTGATGGTTCACGTAGTGGGCCATCGCCCTGATAGACGGTTTTTCGCC
CTTTGACGTTGGAGTCCACGTTCTTTAATAGTGGACTCTTGTTCCAAACTGGA
ACAACACTCAACCCTATCTCGGTCTATTCTTTTGATTTATAAGGGATTTTGCCG
ATTTCGGCCTATTGGTTAAAAAATGAGCTGATTTAACAAAAATTTAACGCGAA
TTTTAACAAAATATTAACGTTTACAATTTAAATATTTGCTTATACAATCTTCCT
GTTTTTGGGGCTTTTCTGATTATCAACCGGGGTACATATGATTGACATGCTAG
TTTTACGATTACCGTTCATCGATTCTCTTGTTTGCTCCAGACTCTCAGGCAATG
ACCTGATAGCCTTTGTAGAGACCTCTCAAAAATAGCTACCCTCTCCGGCATGA
ATTTATCAGCTAGAACGGTTGAATATCATATTGATGGTGATTTGACTGTCTCC
GGCCTTTCTCACCCGTTTGAATCTTTACCTACACATTACTCAGGCATTGCATTT
AAAATATATGAGGGTTCTAAAAATTTTTATCCTTGCGTTGAAATAAAGGCTTC
TCCCGCAAAAGTATTACAGGGTCATAATGTTTTTGGTACAACCGATTTAGCTT
TATGCTCTGAGGCTTTATTGCTTAATTTTGCTAATTCTTTGCCTTGCCTGTATG
ATTTATTGGATGTTGGAATCCTGATGCGGTATTTTCTCCTTACGCATCTGTGCG
GTATTTCACACCGCATATGGTGCACTCTCAGTACAATCTGCTCTGATGCCGCA
TAGTTAAGCCAGCCCCGACACCCGCCAACACCCGCTGACGCGCCCTGACGGG
CTTGTCTGCTCCCGGCATCCGCTTACAGACAAGCTGTGACCGTCTCCGGGAGC
TGCATGTGTCAGAGGTTTTCACCGTCATCACCGAAACGCGCGAGACGAAAGG
GCCTCGTGATACGCCTATTTTTATAGGTTAATGTCATGATAATAATGGTTTCTT
AGACGTCAGGTGGCACTTTTCGGGGAAATGTGCGCGGAACCCCTATTTGTTTA
TTTTTCTAAATACATTCAAATATGTATCCGCTCATGAGACAATAACCCTGATA
AATGCTTCAATAATATTGAAAAAGGAAGAGTATGAGTATTCAACATTTCCGT
GTCGCCCTTATTCCCTTTTTTGCGGCATTTTGCCTTCCTGTTTTTGCTCACCCAG
AAACGCTGGTGAAAGTAAAAGATGCTGAAGATCAGTTGGGTGCACGAGTGGG
TTACATCGAACTGGATCTCAACAGCGGTAAGATCCTTGAGAGTTTTCGCCCCG
AAGAACGTTTTCCAATGATGAGCACTTTTAAAGTTCTGCTATGTGGCGCGGTA
TTATCCCGTATTGACGCCGGGCAAGAGCAACTCGGTCGCCGCATACACTATTC
TCAGAATGACTTGGTTGAGTACTCACCAGTCACAGAAAAGCATCTTACGGAT
GGCATGACAGTAAGAGAATTATGCAGTGCTGCCATAACCATGAGTGATAACA
CTGCGGCCAACTTACTTCTGACAACGATCGGAGGACCGAAGGAGCTAACCGC
TTTTTTGCACAACATGGGGGATCATGTAACTCGCCTTGATCGTTGGGAACCGG
AGCTGAATGAAGCCATACCAAACGACGAGCGTGACACCACGATGCCTGTAGC
AATGGCAACAACGTTGCGCAAACTATTAACTGGCGAACTACTTACTCTAGCTT
```

-continued

CCCGGCAACAATTAATAGACTGGATGGAGGCGGATAAAGTTGCAGGACCACT
TCTGCGCTCGGCCCTTCCGGCTGGCTGGTTTATTGCTGATAAATCTGGAGCCG
GTGAGCGTGGGTCTCGCGGTATCATTGCAGCACTGGGGCCAGATGGTAAGCC
CTCCCGTATCGTAGTTATCTACACGACGGGGAGTCAGGCAACTATGGATGAA
CGAAATAGACAGATCGCTGAGATAGGTGCCTCACTGATTAAGCATTGGTAAC
TGTCAGACCAAGTTTACTCATATATACTTTAGATTGATTTAAAACTTCATTTTT
AATTTAAAAGGATCTAGGTGAAGATCCTTTTTGATAATCTCATGACCAAAATC
CCTTAACGTGAGTTTTCGTTCCACTGAGCGTCAGACCCCGTAGAAAAGATCAA
AGGATCTTCTTGAGATCCTTTTTTTCTGCGCGTAATCTGCTGCTTGCAAACAAA
AAAACCACCGCTACCAGCGGTGGTTTGTTTGCCGGATCAAGAGCTACCAACT
CTTTTTCCGAAGGTAACTGGCTTCAGCAGAGCGCAGATACCAAATACTGTCCT
TCTAGTGTAGCCGTAGTTAGGCCACCACTTCAAGAACTCTGTAGCACCGCCTA
CATACCTCGCTCTGCTAATCCTGTTACCAGTGGCTGCTGCCAGTGGCGATAAG
TCGTGTCTTACCGGGTTGGACTCAAGACGATAGTTACCGGATAAGGCGCAGC
GGTCGGGCTGAACGGGGGGTTCGTGCACACAGCCCAGCTTGGAGCGAACGAC
CTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACA
GGAGAGCGCACGAGGGAGCTTCCAGGGGGAAACGCCTGGTATCTTTATAGTC
CTGTCGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTCCT
GGCCTTTTGCTGGCCTTTTGCTCACATGTTCTTTCCTGCGTTATCCCCTGATTCT
GTGGATAACCGTATTACCGCCTTTGAGTGAGCTGATACCGCTCGCCGCAGCCG
AACGACCGAGCGCAGCGAGTCAGTGAGCGAGGAAGCGGAAGAGCGCCCAAT
ACGCAAACCGCCTCTCCCCGCGCGTTGGCCGATTCATTAATG

Nucleotide:

| | |
|---|---|
| 8-116 | 5'-ITR |
| 128-393 | Human U6 promoter |
| 394-516 | RP-loop sgRNA |
| 524-639 | Delta CMV promoter |
| 1078-1789 | eGFP |
| 2016-2147 | 3'-ITR |

T7-HAtag-Cas9-F (SEQ ID NO.: 10)
TAATACGACTCACTATAGGGATGTACCCATACGATGTTCCAGATTACGCT Cas9-R (SEQ ID NO.: 11)
GCGAGCTCTAGGAATTCTTAC T7-RPloop-F (SEQ ID NO.: 12)
5'-TAATACGACTCACTATAGGGTCTCCCTGAGCTTCAGGGAGT-3'

Common reverse primer sgRNA-R (SEQ ID NO.: 13)
5'-AAAAGCACCGACTCGGTGCC-3'

PAM sequence for SaCa9 (SEQ ID NO.: 14)
NNGRRT where (N, A, T, G, G and R = G, A)

SaCas9 sgRNA with Scaffold sequence (SEQ ID NO.: 15)
GAGGGCCTATTTCCCATGATTCCTTCATATTTGCATATACGATACAAGGCTGTTA
GAGAGATAATTGGAATTAATTTGACTGTAAACACAAAGATATTAGTACAAAATA
CGTGACGTAGAAAGTAATAATTTCTTGGGTAGTTTGCAGTTTTAAAATTATGTTTT
AAAATGGACTATCATATGCTTACCGTAACTTGAAAGTATTTCGATTTCTTGGCTTT
ATATATCTTGTGGAAAGGACGAAACACCGGAGACCACGGCAGGTCTCAGTTTTA
GTACTCTGGAAACAGAATCTACTAAAACAAGGCAAAATGCCGTGTTTATCTCGTC
AACTTGTTGGCGAGATTTTTG 9i4Melt-F2 (mND4) mouse (SEQ ID NO.: 20)
AGT TAG CCA CAT AGC ACT TGT 9i4Melt-R2(mND4) mouse (SEQ ID NO.: 21)
GCT AGA CTT GCT ATC AGT CAT CAT mCox3-Melt-F mouse (SEQ ID NO.: 22)
GAA ACC ACA TAA ATC AAG CCC TAC mCox3-Melt-R mouse (SEQ ID NO.: 23)
GTT GTC GTA GTA GGC AAA CAA TAA G mND1-2820-F mouse (SEQ ID NO.: 24)
TCC TAA CAC TCC TCG TCC CC mND1-2820-R mouse (SEQ ID NO.: 25)
TGG CGT CTG CAA ATG GTT GT -continued mSdhA-F mouse (SEQ ID NO.: 26)
TAC TAC AGC CCC AAG TCT mSdhA-R mouse (SEQ ID NO.: 27)
TGG ACC CAT CTT CTA TGC RPloop-F (SEQ ID NO.: 28)
CCT GAG CTT CAG GGA GTT AAT RPloo-R (SEQ ID NO.: 29)
CGA CTC GGT GCC ACT TTT TC hND1-F human (SEQ ID NO.: 30)
TAC AAC TAC GCA AAG GCC CC hND1-R (SEQ ID NO.: 31)
TGG CGT CTG CAA ATG GTT GT pAAV-dCMV-MLS_AsCpf1 (SEQ ID NO.: 32)
Lowercase: MLS-AsCpf1
Lowercase bold: AsCpf1
CTAAATTGTAAGCGTTAATATTTTGTTAAAATTCGCGTTAAATTTTTGTTAAATCA
GCTCATTTTTTAACCAATAGGCCGAAATCGGCAAAATCCCTTATAAATCAAAAGA
ATAGACCGAGATAGGGTTGAGTGTTGTTCCAGTTTGGAACAAGAGTCCACTATTA
AAGAACGTGGACTCCAACGTCAAAGGGCGAAAAACCGTCTATCAGGGCGATGGC
CCACTACGTGAACCATCACCCTAATCAAGTTTTTTGGGGTCGAGGTGCCGTAAAG
CACTAAATCGGAACCCTAAAGGGAGCCCCCGATTTAGAGCTTGACGGGGAAAGC
CGGCGAACGTGGCGAGAAAGGAAGGGAAGAAAGCGAAAGGAGCGGGCGCTAGG
GCGCTGGCAAGTGTAGCGGTCACGCTGCGCGTAACCACCACACCCGCCGCGCTT
AATGCGCCGCTACAGGGCGCGTCCCATTCGCCATTCAGGCTGCGCAACTGTTGGG
AAGGGCGATCGGTGCGGGCCTCTTCGCTATTACGCCAGCTGGCCACTCCCTCTCT
GCGCGCTCGCTCGCTCACTGAGGCCGGGCGACCAAAGGTCGCCCGACGCCCGGG
CTTTGCCCGGGCGGCCTCAGTGAGCGAGCGAGCGCGCAGAGAGGGAGTGGCCAA
CTCCATCACTAGGGGTTCCTTGTAGTTAATGATTAACCCGCCATGCTACTTATCTA
CGTAGCCATGCTCTAGATTAATTAAACTCACGGGGATTTCCAAGTCTCCACCCCA
TTGACGTCAATGGGAGTTTGTTTTGGCACCAAAATCAACGGGACTTTCCAAAATG
TCGTAATAACCCCGCCCCGTTGACGCAAATGGGCGGTAGGCGTGTACGGTGGGA
GGTCTATATAAGCAGAGCTCGTTTAGTGAACCGTCAGAATTCTCGAGTGATCGAA
AGAGCCTGCTAAAGCAAAAAAGAAGTCACCGCTAGCGCCACCATGGatgttgagccggg
cagtgtgcggcaccagcaggcagctggctccggttttggggtatctgggctccaggcagatgacacagttcgagggctttaccaac
ctgtatcaggtgagcaagacactgcggtttgagctgatcccacagggcaagaccctgaagcacatccaggagcagggcttca
tcgaggaggacaaggcccgcaatgatcactacaaggagctgaagcccatcatcgatcggatctacaagacctatgccgacc
agtgcctgcagctggtgcagctggattgggagaacctgagcgccgccatcgactcctatagaaaggagaaaaccgaggaga
caaggaacgccctgatcgaggagcaggccacatatcgcaatgccatccacgactacttcatcggccggacagacaacctgac
cgatgccatcaataagagacacgccgagatctacaagggcctgttcaaggccgagctgtttaatggcaaggtgctgaagcag
ctgggcaccgtgaccacaaccgagcacgagaacgccctgctgcggagcttcgacaagtttacaacctacttctccggcttttat
gagaacaggaagaacgtgttcagcgccgaggatatcagcacagccatcccacaccgcatcgtgcaggacaacttccccaag
tttaaggagaattgtcacatcttcacacgcctgatcaccgccgtgcccagcctgcgggagcactttgagaacgtgaagaaggc
catcggcatcttcgtgagcacctccatcgaggaggtgttttccttcccttttataaccagctgctgacacagacccagatcgacc
tgtataaccagctgctgggaggaatctctcgggaggcaggcaccgagaagatcaagggcctgaacgaggtgctgaatctgg
ccatccagaagaatgatgagacagcccacatcatcgcctccctgccacacagattcatcccctgtttaagcagatcctgtccg
ataggaacaccctgtctttcatcctggaggagtttaagagcgacgaggaagtgatccagtccttctgcaagtacaagacactg
ctgagaaacgagaacgtgctggagacagccgaggccctgtttaacgagctgaacagcatcgacctgacacacatcttcatca
gccacaagaagctggagacaatcagcagcgccctgtgcgaccactgggatacactgaggaatgccctgtatgagcggagaa
tctccgagctgacaggcaagatcaccaagtctgccaaggagaaggtgcagcgcagcctgaagcacgaggatatcaacctgc
aggagatcatctctgccgcaggcaaggagctgagcgaggccttcaagcagaaaaccagcgagatcctgtcccacgcacacg
ccgccctggatcagccactgcctacaaccctgaagaagcaggaggagaaggagatcctgaagtctcagctggacagcctgct
gggcctgtaccacctgctggactggtttgccgtggatgagtccaacgaggtggaccccgagttctctgcccggctgaccggcat
caagctggagatggagccttctctgagcttctacaacaaggccagaaattatgccaccaagaagccctactccgtggagaagt
tcaagctgaactttcagatgcctacactggcctctggctgggacgtgaataaggagaagaacaatggcgccatcctgtttgtga
agaacggcctgtactatctgggcatcatgccaaagcagaagggcaggtataaggccctgagcttcgagcccacagagaaaa
ccagcgagggctttgataagatgtactatgactacttccctgatgccgccaagatgatcccaaagtgcagcacccagctgaag
gccgtgacagcccactttcagacccacacaacccccatcctgctgtccaacaatttcatcgagcctctggagatcacaaagga
gatctacgacctgaacaatcctgagaaggagccaaagaagtttcagacagcctacgccaagaaaaccggcgaccagaagg
gctacagagaggccctgtgcaagtggatcgacttcacaagggattttctgtccaagtataccaagacaacctctatcgatctgt
ctagcctgcggccatcctctcagtataaggacctgggcgagtactatgccgagctgaatcccctgctgtaccacatcagcttcc
agagaatcgccgagaaggagatcatggatgccgtggagacaggcaagctgtacctgttccagatctataacaaggactttgc
caagggccaccacggcaagcctaatctgcacacactgtattggaccggcctgttttctccagagaacctggccaagacaagc
atcaagctgaatggccaggccgagctgttctaccgccctaagtccaggatgaagaggatggcacaccggctgggagagaag
atgctgaacaagaagctgaaggatcagaaaaccccaatccccgacaccctgtaccaggagctgtacgactatgtgaatcaca
gactgtcccacgacctgtctgatgaggccagggccctgctgcccaacgtgatcaccaaggaggtgtctcacgagatcatcaag
gataggcgctttaccagcgacaagttctttttccacgtgcctatcacactgaactatcaggccgccaattccccatctaagttca
accagagggtgaatgcctacctgaaggagcaccccgagacacctatcatcggcatcgatcggggcgagagaaacctgatct
atatcacagtgatcgactccaccggcaagatcctggagcagcggagcctgaacaccatccagcagtttgattaccagaagaa
gctggacaacagggagaaggagagggtggcagcaaggcaggcctggtctgtggtgggcacaatcaaggatctgaagcagg
gctatctgagccaggtcatccacgagatcgtggacctgatgatccactaccaggccgtggtggtgctggagaacctgaatttcg
gctttaagagcaagaggaccggcatcgccgagaaggccgtgtaccagcagttcgagaagatgctgatcgataagctgaattg
cctggtgctgaaggactatccagcagagaaagtgggaggcgtgctgaacccataccagctgacagaccagttcacctccttttg

-continued ccaagatgggcacccagtctggcttcctgttttacgtgcctgccccatatacatctaagatcgatcccctgaccggcttcgtgga
ccccttcgtgtggaaaaccatcaagaatcacgagagccgcaagcacttcctggagggcttcgactttctgcactacgacgtga
aaaccggcgacttcatcctgcactttaagatgaacagaaatctgtccttccagaggggcctgcccggctttatgcctgcatggg
atatcgtgttcgagaagaacgagacacagtttgacgccaagggcacccctttcatcgccggcaagagaatcgtgccagtgatc
gagaatcacagattcaccggcagataccgggacctgtatcctgccaacgagctgatcgccctgctggaggagaagggcatcg
tgttcagggatggctccaacatcctgccaaagctgctggagaatgacgattctcacgccatcgacaccatggtggccctgatcc
gcagcgtgctgcagatgcggaactccaatgccgccacaggcgaggactatatcaacagccccgtgcgcgatctgaatggcgt
gtgcttcgactcccggtttcagaacccagagtggcccatggacgccgatgccaatggcgcctaccacatcgccctgaagggcc
agctgctgctgaatcacctgaaggagagcaaggatctgaagctgcagaacggcatctccaatcaggactggctggcctacat
ccaggagctgcgcaacatgtccgtcctgacgccgctgctgctgcggggcttgacaggctcggcccggcggctcccagtgccgcgc
gccaaGCGGCCGCAATAAAAGATCTTTATTTTCATTAGATCTGTGTGTTGGTTTTTTG
TGTGTCTAGACATGGCTACGTAGATAATTAGCATGGCGGGTTAATCATTAAAGGA
ACCCCTAGTGATGGAGTTGGCCACTCCCTCTCTGCGCGCTCGCTCGCTCACTGAG
GCCGGGCGACCAAAGGTCGCCCGACGCCCGGGCTTTGCCCGGGCGGCCTCAGTG
AGCGAGCGAGCGCGCAGAGAGGGAGTGGCCAGCTGCATTAATGAATCGGCCAAC
GCGCGGGGAGAGGCGGTTTGCGTATTGGGCGCTCTTCCGCTTCCTCGCTCACTGA
CTCGCTGCGCTCGGTCGTTCGGCTGCGGCGAGCGGTATCAGCTCACTCAAAGGCG
GTAATACGGTTATCCACAGAATCAGGGGATAACGCAGGAAAGAACATGTGAGCA
AAAGGCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCAGAGG
TGGCGAAACCCGACAGGACTATAAAGATACCAGGCGTTTCCCCCTGGAAGCTCC
CTCGTGCGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCAGTTCG
GTGTAGGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGACACGA
CTTATCGCCACTGGCAGCAGCCACTGGTAACAGGATTAGCAGAGCGAGGTATGT
AGGCGGTGCTACAGAGTTCTTGAAGTGGTGGCCTAACTACGGCTACACTAGAAG
GACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGATCT
TTTCTACGGGGTCTGACGCTCAGTGGAACGAAAACTCACGTTAAGGGATTTTGGT
CATGAGATTATCAAAAAGGATCTTCACCTAGATCCTTTTAAATTAAAAATGAAGT
TTTAAATCAATCTAAAGTATATATGAGTAAACTTGGTCTGACAGTTACCAATGCT
TAATCAGTGAGGCACCTATCTCAGCGATCTGTCTATTTCGTTCATCCATAGTTGCC
TGACTCCCCGTCGTGTAGATAACTACGATACGGGAGGGCTTACCATCTGGCCCCA
GTGCTGCAATGATACCGCGAGACCCACGCTCACCGGCTCCAGATTTATCAGCAAT
AAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTT
AATAGTTTGCGCAACGTTGTTGCCATTGCTACAGGCATCGTGGTGTCACGCTCGT
CGTTTGGTATGGCTTCATTCAGCTCCGGTTCCCAACGATCAAGGCGAGTTACATG
ATCCCCCATGTTGTGCAAAAAAGCGGTTAGCTCCTTCGGTCCTCCGATCGTTGTC
AGAAGTAAGTTGGCCGCAGTGTTATCACTCATGGTTATGGCAGCACTGCATAATT
CTCTTACTGTCATGCCATCCGTAAGATGCTTTTCTGTGACTGGTGAGTACTCAACC
AAGTCATTCTGAGAATAGTGTATGCGGCGACCGAGTTGCTCTTGCCCGGCGTCAA
TACGGGATAATACCGCGCCACATAGCAGAACTTTAAAAGTGCTCATCATTGGAA
AACGTTCTTCGGGGCGAAAACTCTCAAGGATCTTACCGCTGTTGAGATCCAGTTC
GATGTAACCCACTCGTGCACCCAACTGATCTTCAGCATCTTTTACTTTCACCAGCG
TTTCTGGGTGAGCAAAAACAGGAAGGCAAAATGCCGCAAAAAAGGGAATAAGG
GCGACACGGAAATGTTGAATACTCATACTCTTCCTTTTTCAATATTATTGAAGCAT
TTATCAGGGTTATTGTCTCATGAGCGGATACATATTTGAATGTATTTAGAAAAAT
AAACAAATAGGGGTTCCGCGCACATTTCCCCGAAAAGTGCCAC pAAV-dCMV-MLS_C2c1 (SEQ ID NO.: 33)
Lowercase: MLS-C2c1
Lowercase bold: C2c1
CTAAATTGTAAGCGTTAATATTTTGTTAAAATTCGCGTTAAATTTTTGTTAAATCA
GCTCATTTTTTAACCAATAGGCCGAAATCGGCAAAATCCCTTATAAATCAAAAGA
ATAGACCGAGATAGGGTTGAGTGTTGTTCCAGTTTGGAACAAGAGTCCACTATTA
AAGAACGTGGACTCCAACGTCAAAGGGCGAAAAACCGTCTATCAGGGCGATGGC
CCACTACGTGAACCATCACCCTAATCAAGTTTTTTGGGGTCGAGGTGCCGTAAAG
CACTAAATCGGAACCCTAAAGGGAGCCCCCGATTTAGAGCTTGACGGGGAAAGC
CGGCGAACGTGGCGAGAAAGGAAGGGAAGAAAGCGAAAGGAGCGGGCGCTAGG
GCGCTGGCAAGTGTAGCGGTCACGCTGCGCGTAACCACCACACCCGCCGCGCTT
AATGCGCCGCTACAGGGCGCGTCCCATTCGCCATTCAGGCTGCGCAACTGTTGGG
AAGGGCGATCGGTGCGGGCCTCTTCGCTATTACGCCAGCTGGCCACTCCCTCTCT
GCGCGCTCGCTCGCTCACTGAGGCCGGGCGACCAAAGGTCGCCCGACGCCCGGG
CTTTGCCCGGGCGGCCTCAGTGAGCGAGCGAGCGCGCAGAGAGGGAGTGGCCAA
CTCCATCACTAGGGGTTCCTTGTAGTTAATGATTAACCCGCCATGCTACTTATCTA
CGTAGCCATGCTCTAGATTAATTAAACTCACGGGGATTTCCAAGTCTCCACCCCA
TTGACGTCAATGGGAGTTTGTTTTGGCACCAAAATCAACGGGACTTTCCAAAATG
TCGTAATAACCCCGCCCCGTTGACGCAAATGGGCGGTAGGCGTGTACGGTGGGA
GGTCTATATAAGCAGAGCTCGTTTAGTGAACCGTCAGAATTCTCGAGTGATCGAA
AGAGCCTGCTAAAGCAAAAAAGAAGTCACCGCTAGCGCCACCATGGatgttgagccggg
cagtgtgcggcaccagcaggcagctggctccggttttggggtatctgggctccaggcagatggccgtcaaatccatcaaagtgaa
acttcgtctcgacgatatgccggagattcgggccggtctatggaaacttcataaggaagtcaatgcgggggttcgatattacac
ggaatggctcagtcttctccgtcaagagaacttgtatcgaagaagtccgaatggggacggagagcaagaatgtgataagact
gcagaagaatgcaaagccgaattgttggagcggctgcgcgcgcgtcaagtggagaatggacaccgtggtccggcgggatcg
gacgatgaattgctgcagttggcgcgtcaactctatgagttgttggttccgcaggcgataggtgcgaaaggcgacgcgcagca
aattgcccgcaaattttgagccccttggccgacaaggacgcagttggtgggcttggaatcgcgaaggcggggaacaaaccg

-continued cggtgggttcgcatgcgcgaagcgggggaaccaggctgggaagaggagaaggagaaggctgagacgaggaaatctgcgg
atcggactgcggatgttttgcgcgcgctcgcggattttgggttaaagccactgatgcgcgtatacaccgattctgagatgtcatc
ggtggagtggaaaccgcttcggaagggacaagccgttcggacgtgggatagggacatgttccaacaagctatcgaacggat
gatgtcgtgggagtcgtggaatcagcgcgttgggcaagagtacgcgaaactcgtagaacaaaaaaatcgatttgagcagaa
gaatttcgtcggccaggaacatctggtccatctcgtcaatcagttgcaacaagatatgaaagaagcatcgcccggactcgaat
cgaaagagcaaaccgcgcactatgtgacgggacgggcattgcgcggatcggacaaggtatttgagaagtgggggaaactcg
cccccgatgcacctttcgatttgtacgacgccgaaatcaagaatgtgcagagacgtaacacgagacgattcggatcacatgac
ttgttcgcaaaattggcagagccagagtatcaggccctgtggcgcgaagatgcttcgtttctcacgcgttacgcggtgtacaac
agcatccttcgcaaactgaatcacgccaaaatgttcgcgacgtttactttgccggatgcaacggcgcacccgatttggactcgc
ttcgataaattgggtgggaatttgcaccagtacaccttttttgttcaacgaatttggagaacgcaggcacgcgattcgttttcaca
agctattgaaagtcgagaatggtgtcgcaagagaagttgatgatgtcaccgtgcccatttcaatgtcagagcaattggataatc
tgcttcccagagatcccaatgaaccgattgcgctatatttcgagattacggagccgaacagcatttcacaggtgaatttggtgg
cgcgaagatccagtgccgccgggatcagctggctcatatgcaccgacgcagaggggcgagggatgtttatctcaatgtcagc
gtacgtgtgcagagtcagtctgaggcgcggggagaacgtcgcccgccgtatgcggcagtatttcgtctggtcggggacaacc
atcgcgcgtttgtccatttcgataaactatcggattatcttgcggaacatccggatgatgggaagctcgggtcggaggggttgct
ttccgggctgcgggtgatgagtgtcgatctcggccttcgcacatctgcatcgatttccgtttttcgcgttgcccggaaggacgagt
tgaagccgaactcaaaaggtcgtgtaccgtttttctttccgataaaagggaatgacaatctcgtcgcggttcatgagcgatcac
aactcttgaagctgcctggcgaaacggagtcgaaggacctgcgtgctatccgagaagaacgccaacggacattgcggcagtt
gcggacgcaactggcgtatttgcggctgctcgtgcggtgtgggtcggaagatgtggggcggcgtgaacggagttgggcaaag
cttatcgagcagccggtggatgcggccaatcacatgacaccggattggcgcgaggcttttgaaaacgaacttcagaagcttaa
gtcactccatggtatctgtagcgacaaggaatggatggatgctgtctacgagagcgttcgccgcgtgtggcgtcacatgggca
aacaggttcgcgattggcgaaaggacgtacgaagcggagagcggcccaagattcgcggctatgcgaaagacgtggtcggtg
gaaactcgattgagcaaatcgagtatctggaacgtcagtacaagttcctcaagagttggagcttctttggtaaggtgtcgggac
aagtgattcgtgcggagaagggatctcgttttgcgatcacgctgcgcgaacacattgatcacgcgaaggaagatcggctgaa
gaaattggcggatcgcatcattatggaggctctcggctatgtgtacgcgttggatgagcgcggcaaaggaaagtgggttgcga
agtatccgccgtgccagctcatcctgctggaggaattgagcgagtaccagttcaataacgacaggcctccgagcgaaaacaa
ccagttgatgcaatggagtcatcgcggcgtgttccaggagttgataaatcaggcccaagtccatgatttactcgttggacgat
gtatgcagcgttctcgtcgcgattcgacgcgcgaactggggcaccgggtatccgctgtcgccgggttccggcgcgttgcaccca
ggagcacaatccagaaccatttccttggtggctgaacaagtttgtggtggaacatacgttggatgcttgtcccctacgcgcaga
cgacctcatcccaacgggtgaaggagagatttttgtctcgccgttcagcgcggaggagggggactttcatcagattcacgccg
acctgaatgcggcgcaaaatctgcagcagcgactctggtctgattttgatatcagtcaaattcggttgcggtgtgattggggtga
agtggacggtgaactcgttctgatcccaaggcttacaggaaaacgaacggcggattcatatagcaacaaggtgttttatacca
atacaggtgtcacctattatgagcgagagcgggggaagaagcggagaaaggttttcgcgcaagagaaattgtcggaggaag
aggcggagttgctcgtggaagcagacgaggcgagggagaaatcggtcgttttgatgcgtgatccgtctggcatcatcaatcgg
ggaaattggaccaggcaaaaggaattttggtcgatggtgaaccagcggatcgaaggatacttggtcaagcagattcgctcgc
gcgttccattacaagatagtgcgtgtgaaaacacggggggatatttaaatgtccgtcctgacgccgctgctgctgcggggcttgac
aggctcggcccggcggctcccagtgccgcgcgccaaGCGGCCGCAATAAAAGATCTTTATTTTCATT
AGATCTGTGTGTTGGTTTTTTGTGTGTCTAGACATGGCTACGTAGATAATTAGCAT
GGCGGGTTAATCATTAAAGGAACCCCTAGTGATGGAGTTGGCCACTCCCTCTCTG
CGCGCTCGCTCGCTCACTGAGGCCGGGCGACCAAAGGTCGCCCGACGCCCGGGC
TTTGCCCGGGCGGCCTCAGTGAGCGAGCGAGCGCGCAGAGAGGGAGTGGCCAGC
TGCATTAATGAATCGGCCAACGCGCGGGGAGAGGCGGTTTGCGTATTGGGCGCT
CTTCCGCTTCCTCGCTCACTGACTCGCTGCGCTCGGTCGTTCGGCTGCGGCGAGC
GGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAA
AGGCCGCGTTGCTGGCGTTTTTCCATAGGCTCCGCCCCCCTGACGAGCATCACAA
AAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTA
CCGGATACCTGTCCGCCTTTCTCCCTTCGGGAAGCGTGGCGCTTTCTCATAGCTCA
CGCTGTAGGTATCTCAGTTCGGTGTAGGTCGTTCGCTCCAAGCTGGGCTGTGTGC
ACGAACCCCCCGTTCAGCCCGACCGCTGCGCCTTATCCGGTAACTATCGTCTTGA
GTCCAACCCGGTAAGACACGACTTATCGCCACTGGCAGCAGCCACTGGTAACAG
GATTAGCAGAGCGAGGTATGTAGGCGGTGCTACAGAGTTCTTGAAGTGGTGGCC
TAACTACGGCTACACTAGAAGGACAGTATTTGGTATCTGCGCTCTGCTGAAGCCA
GTTACCTTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAAAGGATC
TCAAGAAGATCCTTTGATCTTTTCTACGGGGTCTGACGCTCAGTGGAACGAAAAC
TCACGTTAAGGGATTTTGGTCATGAGATTATCAAAAAGGATCTTCACCTAGATCC
TTTTAAATTAAAAATGAAGTTTTAAATCAATCTAAAGTATATATGAGTAAACTTG
GTCTGACAGTTACCAATGCTTAATCAGTGAGGCACCTATCTCAGCGATCTGTCTA
TTTCGTTCATCCATAGTTGCCTGACTCCCCGTCGTGTAGATAACTACGATACGGG
AGGGCTTACCATCTGGCCCCAGTGCTGCAATGATACCGCGAGACCCACGCTCACC
GGCTCCAGATTTATCAGCAATAAACCAGCCAGCCGGAAGGGCCGAGCGCAGAAG
TGGTCCTGCAACTTTATCCGCCTCCATCCAGTCTATTAATTGTTGCCGGGAAGCTA
GAGTAAGTAGTTCGCCAGTTAATAGTTTGCGCAACGTTGTTGCCATTGCTACAGG
CATCGTGGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGCTCCTT
CGGTCCTCCGATCGTTGTCAGAAGTAAGTTGGCCGCAGTGTTATCACTCATGGTT
ATGGCAGCACTGCATAATTCTCTTACTGTCATGCCATCCGTAAGATGCTTTTCTGT
GACTGGTGAGTACTCAACCAAGTCATTCTGAGAATAGTGTATGCGGCGACCGAG
TTGCTCTTGCCCGGCGTCAATACGGGATAATACCGCGCCACATAGCAGAACTTTA
AAAGTGCTCATCATTGGAAAACGTTCTTCGGGGCGAAAACTCTCAAGGATCTTAC
CGCTGTTGAGATCCAGTTCGATGTAACCCACTCGTGCACCCAACTGATCTTCAGC
ATCTTTTACTTTCACCAGCGTTTCTGGGTGAGCAAAAACAGGAAGGCAAAATGCC
GCAAAAAAGGGAATAAGGGCGACACGGAAATGTTGAATACTCATACTCTTCCTT
TTTCAATATTATTGAAGCATTTATCAGGGTTATTGTCTCATGAGCGGATACATATT
TGAATGTATTTAGAAAAATAAACAAATAGGGGTTCCGCGCACATTTCCCCGAAA
AGTGCCAC-3'

-continued pAAV-dCMV-MLS_SaCas9 (SEQ ID NO.: 34)
Lowercase: MLS-SaCas9
Lowercase bold: SaCas9
CTAAATTGTAAGCGTTAATATTTTGTTAAAATTCGCGTTAAATTTTTGTTAAATCA
GCTCATTTTTTAACCAATAGGCCGAAATCGGCAAAATCCCTTATAAATCAAAAGA
ATAGACCGAGATAGGGTTGAGTGTTGTTCCAGTTTGGAACAAGAGTCCACTATTA
AAGAACGTGGACTCCAACGTCAAAGGGCGAAAAACCGTCTATCAGGGCGATGGC
CCACTACGTGAACCATCACCCTAATCAAGTTTTTTGGGGTCGAGGTGCCGTAAAG
CACTAAATCGGAACCCTAAAGGGAGCCCCCGATTTAGAGCTTGACGGGGAAAGC
CGGCGAACGTGGCGAGAAAGGAAGGGAAGAAAGCGAAAGGAGCGGGCGCTAGG
GCGCTGGCAAGTGTAGCGGTCACGCTGCGCGTAACCACCACACCCGCCGCGCTT
AATGCGCCGCTACAGGGCGCGTCCCATTCGCCATTCAGGCTGCGCAACTGTTGGG
AAGGGCGATCGGTGCGGGCCTCTTCGCTATTACGCCAGCTGGCCACTCCCTCTCT
GCGCGCTCGCTCGCTCACTGAGGCCGGGCGACCAAAGGTCGCCCGACGCCCGGG
CTTTGCCCGGGCGGCCTCAGTGAGCGAGCGAGCGCGCAGAGAGGGAGTGGCCAA
CTCCATCACTAGGGGTTCCTTGTAGTTAATGATTAACCCGCCATGCTACTTATCTA
CGTAGCCATGCTCTAGATTAATTAAACTCACGGGGATTTCCAAGTCTCCACCCCA
TTGACGTCAATGGGAGTTTGTTTTGGCACCAAAATCAACGGGACTTTCCAAAATG
TCGTAATAACCCCGCCCCGTTGACGCAAATGGGCGGTAGGCGTGTACGGTGGGA
GGTCTATATAAGCAGAGCTCGTTTAGTGAACCGTCAGAATTCTCGAGTGATCGAA
AGAGCCTGCTAAAGCAAAAAAGAAGTCACCGCTAGCGCCACCATGGatgttgagccggg
cagtgtgcggcaccagcaggcagctggctccggttttggggtatctgggctccaggcagaagcggaaggtcggtatccacggagt
cccagcagccaagcggaactacatcctgggcctggacatcggcatcaccagcgtgggctacggcatcatcgactacgagaca
cgggacgtgatcgatgccggcgtgcggctgttcaaagaggccaacgtggaaaacaacgagggcaggcggagcaagagag
gcgccagaaggctgaagcggcggaggcggcatagaatccagagagtgaagaagctgctgttcgactacaacctgctgaccg
accacagcgagctgagcggcatcaacccctacgaggccagagtgaagggcctgagccagaagctgagcgaggaagagttc
tctgccgccctgctgcacctggccaagagaagaggcgtgcacaacgtgaacgaggtggaagaggacaccggcaacgagct
gtccaccaaagagcagatcagccggaacagcaaggccctggaagagaaatacgtggccgaactgcagctggaacggctga
agaaagacggcgaagtgcggggcagcatcaacagattcaagaccagcgactacgtgaaagaagccaaacagctgctgaa
ggtgcagaaggcctaccaccagctggaccagagcttcatcgacacctacatcgacctgctggaaacccggcggacctactat
gagggacctggcgagggcagccccttcggctggaaggacatcaaagaatggtacgagatgctgatgggccactgcacctac
ttccccgaggaactgcggagcgtgaagtacgcctacaacgccgacctgtacaacgccctgaacgacctgaacaatctcgtga
tcaccagggacgagaacgagaagctggaatattacgagaagttccagatcatcgagaacgtgttcaagcagaagaagaag
cccaccctgaagcagatcgccaaagaaatcctcgtgaacgaagaggatattaagggctacagagtgaccagcaccggcaag
cccgagttcaccaacctgaaggtgtaccacgacatcaaggacattaccgcccggaaagagattattgagaacgccgagctgc
tggatcagattgccaagatcctgaccatctaccagagcagcgaggacatccaggaagaactgaccaatctgaactccgagct
gacccaggaagagatcgagcagatctctaatctgaagggctataccggcacccacaacctgagcctgaaggccatcaacctg
atcctggacgagctgtggcacaccaacgacaaccagatcgctatcttcaaccggctgaagctggtgcccaagaaggtggacc
tgtcccagcagaaagagatccccaccaccctggtggacgacttcatcctgagccccgtcgtgaagagaagcttcatccagagc
atcaaagtgatcaacgccatcatcaagaagtacggcctgcccaacgacatcattatcgagctggcccgcgagaagaactcca
aggacgcccagaaaatgatcaacgagatgcagaagcggaaccggcagaccaacgagcggatcgaggaaatcatccggac
caccggcaaagagaacgccaagtacctgatcgagaagatcaagctgcacgacatgcaggaaggcaagtgcctgtacagcct
ggaagccatccctctggaagatctgctgaacaaccccttcaactatgaggtggaccacatcatccccagaagcgtgtccttcg
acaacagcttcaacaacaaggtgctcgtgaagcaggaagaaaacagcaagaagggcaaccggaccccattccagtacctg
agcagcagcgacagcaagatcagctacgaaaccttcaagaagcacatcctgaatctggccaagggcaagggcagaatcag
caagaccaagaaagagtatctgctggaagaacgggacatcaacaggttctccgtgcagaaagacttcatcaaccggaacct
ggtggataccagatacgccaccagaggcctgatgaacctgctgcggagctacttcagagtgaacaacctggacgtgaaagtg
aagtccatcaatggcggcttcaccagctttctgcggcggaagtggaagtttaagaaagagcggaacaaggggtacaagcac
cacgccgaggacgccctgatcattgccaacgccgatttcatcttcaaagagtggaagaaactggacaaggccaaaaaagtg
atggaaaaccagatgttcgaggaaaagcaggccgagagcatgcccgagatcgaaaccgagcaggagtacaaagagatctt
catcacccccccaccagatcaagcacattaaggacttcaaggactacaagtacagccaccgggtggacaagaagcctaatag
agagctgattaacgacaccctgtactccacccggaaggacgacaagggcaacaccctgatcgtgaacaatctgaacggcctg
tacgacaaggacaatgacaagctgaaaaagctgatcaacaagagccccgaaaagctgctgatgtaccaccacgacccccca
gacctaccagaaactgaagctgattatggaacagtacggcgacgagaagaatcccctgtacaagtactacgaggaaaccgg
gaactacctgaccaagtactccaaaaaggacaacggccccgtgatcaagaagattaagtattacggcaacaaactgaacgc
ccatctggacatcaccgacgactaccccaacagcagaaacaaggtcgtgaagctgtccctgaagccctacagattcgacgtg
tacctggacaatggcgtgtacaagttcgtgaccgtgaagaatctggatgtgatcaaaaaagaaaactactacgaagtgaata
gcaagtgctatgaggaagctaagaagctgaagaagatcagcaaccaggccgagtttatcgcctccttctacaacaacgatct
gatcaagatcaacggcgagctgtatagagtgatcggcgtgaacaacgacctgctgaaccggatcgaagtgaacatgatcga
catcacctaccgcgagtacctggaaaacatgaacgacaagaggcccccccaggatcattaagacaatcgcctccaagaccca
gagcattaagaagtacagcacagacattctgggcaacctgtatgaagtgaaatctaagaagcaccctcagatcatcaaaaag
ggcatgtccgtcctgacgccgctgctgctgcggggcttgacaggctcggcccggcggctcccagtgccgcgcgccaaGCGGC
CGCAATAAAAGATCTTTATTTTCATTAGATCTGTGTGTTGGTTTTTTGTGTGTCTA
GACATGGCTACGTAGATAATTAGCATGGCGGGTTAATCATTAAAGGAACCCCTA
GTGATGGAGTTGGCCACTCCCTCTCTGCGCGCTCGCTCGCTCACTGAGGCCGGGC
GACCAAAGGTCGCCCGACGCCCGGGCTTTGCCCGGGCGGCCTCAGTGAGCGAGC
GAGCGCGCAGAGAGGGAGTGGCCAGCTGCATTAATGAATCGGCCAACGCGCGGG
GAGAGGCGGTTTGCGTATTGGGCGCTCTTCCGCTTCCTCGCTCACTGACTCGCTG
CGCTCGGTCGTTCGGCTGCGGCGAGCGGTATCAGCTCACTCAAAGGCGGTAATAC
GGTTATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCATAGG
CTCCGCCCCCCTGACGAGCATCACAAAAATCGACGCTCAAGTCAGAGGTGGCGA
AACCCGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGTGTAGG
TCGTTCGCTCCAAGCTGGGCTGTGTGCACGAACCCCCCGTTCAGCCCGACCGCTG
CGCCTTATCCGGTAACTATCGTCTTGAGTCCAACCCGGTAAGACACGACTTATCG
CCACTGGCAGCAGCCACTGGTAACAGGATTAGCAGAGCGAGGTATGTAGGCGGT
GCTACAGAGTTCTTGAAGTGGTGGCCTAACTACGGCTACACTAGAAGGACAGTA -continued

```
TTTGGTATCTGCGCTCTGCTGAAGCCAGTTACCTTCGGAAAAAGAGTTGGTAGCT
CTTGATCCGGCAAACAAACCACCGCTGGTAGCGGTGGTTTTTTTGTTTGCAAGCA
GCAGATTACGCGCAGAAAAAAAGGATCTCAAGAAGATCCTTTGATCTTTTCTACG
GGGTCTGACGCTCAGTGGAACGAAAACTCACGTTAAGGGATTTTGGTCATGAGA
TTATCAAAAAGGATCTTCACCTAGATCCTTTTAAATTAAAAATGAAGTTTTAAAT
CAATCTAAAGTATATATGAGTAAACTTGGTCTGACAGTTACCAATGCTTAATCAG
TGAGGCACCTATCTCAGCGATCTGTCTATTTCGTTCATCCATAGTTGCCTGACTCC
CCGTCGTGTAGATAACTACGATACGGGAGGGCTTACCATCTGGCCCCAGTGCTGC
AATGATACCGCGAGACCCACGCTCACCGGCTCCAGATTTATCAGCAATAAACCA
GCCAGCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTAATAGT
TTGCGCAACGTTGTTGCCATTGCTACAGGCATCGTGGTGTCACGCTCGTCGTTTG
GTATGGCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCAGAAGT
AAGTTGGCCGCAGTGTTATCACTCATGGTTATGGCAGCACTGCATAATTCTCTTA
CTGTCATGCCATCCGTAAGATGCTTTTCTGTGACTGGTGAGTACTCAACCAAGTC
ATTCTGAGAATAGTGTATGCGGCGACCGAGTTGCTCTTGCCCGGCGTCAATACGG
GATAATACCGCGCCACATAGCAGAACTTTAAAAGTGCTCATCATTGGAAAACGTT
CTTCGGGGCGAAAACTCTCAAGGATCTTACCGCTGTTGAGATCCAGTTCGATGTA
ACCCACTCGTGCACCCAACTGATCTTCAGCATCTTTTACTTTCACCAGCGTTTCTG
GGTGAGCAAAAACAGGAAGGCAAAATGCCGCAAAAAAGGGAATAAGGGCGACA
CGGAAATGTTGAATACTCATACTCTTCCTTTTTCAATATTATTGAAGCATTTATCA
GGGTTATTGTCTCATGAGCGGATACATATTTGAATGTATTTAGAAAAATAAACAA
ATAGGGGTTCCGCGCACATTTCCCCGAAAAGTGCCAC

SEQ ID NO.: 35
GCAAACTCCAACTACGAACGGATCCACAGCCGTACTATAATCATGGCCCGAG
```

What is claimed is:

1. A hybrid guide RNA comprising an RP loop sequence, a spacer, a target polynucleotide sequence, a crRNA sequence, and a tracrRNA sequence, wherein the hybrid guide RNA comprises the nucleotide sequence of SEQ ID NO: 6 or wherein nucleotides corresponding to nucleotides 1 to 27 and 47 to 129 of SEQ ID NO: 6 are at least 85% identical to nucleotides 1 to 27 and 47 to 129 of the nucleotide sequence of SEQ ID NO: 6.

2. The hybrid guide RNA of claim 1, wherein the hybrid guide RNA comprises the nucleotide sequence of SEQ ID NO: 7, or a nucleotide sequence having at least 85% sequence identity thereto.

3. The hybrid guide RNA of claim 1, wherein nucleotides 28 to 46 of SEQ ID NO: 6 are a target polynucleotide sequence targeted to a polynucleotide sequence located inside a mitochondrion.

4. The hybrid guide RNA of claim 1, wherein nucleotides 28 to 46 of SEQ ID NO: 6 are a target polynucleotide sequence targeted to a mtND4 gene hybrid.

5. A recombinant expression system for CRISPR-based mitochondrial gene editing comprising:

(a) one or more expression vectors;

(b) a polynucleotide encoding a recombinant Cas9 endonuclease; and (c) the hybrid guide RNA of claim 1.

6. The recombinant expression system of claim 5, wherein the expression vector is a recombinant AAV of the serotypes AAV1, AAV2, AAV3, AAV4, AAV5, AAV6, AAV7, AAV8, AAV9, AAV10, or AAV11; or an AAV hybrid vector combining the capsid of any of serotypes AAV1, AAV2, AAV3, AAV4, AAV5, AAV6, AAV7, AAV8, AAV9, AAV10, or AAV11 with the viral genome of any other serotypes AAV1, AAV2, AAV3, AAV4, AAV5, AAV6, AAV7, AAV8, AAV9, AAV10, or AAV11; or a self-complementary recombinant AAV vector; and/or one of scAAV2, scAAV9, rAAV2, or rAAV9 recombinant AAV vector.

7. A recombinant expression system for CRISPR-based mitochondrial gene editing comprising:

(a) a polynucleotide encoding a recombinant Cas9 endonuclease;

(b) C12-200;

(c) one or more expression vectors; and (d) the hybrid guide RNA of claim 1.

8. The recombinant expression system of claim 5, wherein the polynucleotide encoding the recombinant Cas9 endonuclease encodes an spCas9, saCas9, C2c1, nickase or Cpf1.

9. The recombinant expression system of claim 5, further comprising a donor polynucleotide that encodes an edited version of a mitochondrial polynucleotide.

10. The recombinant expression system of claim 5, wherein the Cas9 polynucleotide further comprises one or more mitochondrial localization signals (MLS) selected from the group of MLS1, Cox8A-MLS2, or hSORD2-MLS and the expression vector comprises the nucleotide sequence of SEQ ID NO: 8 or 9, or a nucleotide sequence having at least 85% sequence identity to each thereof.

11. A viral packaging system comprising the recombinant expression system of claim 5 and a packaging cell line.

12. A viral particle comprising the recombinant expression system of claim 5.

13. The viral particle of claim 12, wherein said viral particle is a plurality of viral particles.

14. A composition comprising the plurality of viral particles of claim 13 and pharmaceutically acceptable carrier.

15. A method for shifting mitochondrial heteroplasmy in a cell, comprising administering an effective amount of the recombinant expression system of claim 5, thereby shifting mitochondrial heteroplasmy in the cell.

16. The method of claim 15, further comprising assaying for the expression of mtND4.

17. A method of CRISPR-based mitochondrial gene editing in a subject, comprising administering an effective amount of the viral particle of claim 12 to the subject, thereby editing a mitochondrial gene in the subject.

18. A method of treating a mitochondrial condition in a subject, the method comprising administering an effective amount of the recombinant expression system of claim 5 to the subject, thereby treating the mitochondrial condition in the subject.

19. The method of claim 18, wherein the mitochondrial condition is Pearson Syndrome, Kearns-Sayre Syndrome, progressive external ophthalmoplegia, mitochondrial myopathy, encephalopathy, lactic acidosis, stroke-like syndrome (MELAS), myoclonic epilepsy with ragged-red fibers (MERFF), Leber hereditary optic neuropathy (LHON) or Leigh Syndrome.

* * * * *

```
                              SEQUENCE LISTING

<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

tctccctgag cttcagggag                                                  20


<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2

ucucccugag cuucagggag                                                  20


<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

agaagcgtat cccgctgagc                                                  20


<210> SEQ ID NO 4
<211> LENGTH: 20
<212> TYPE: RNA
<213> ORGANISM: Artificial Sequence
```

<220> FEATURE:
<223> OTHER INFORMATION: Description of Artificial Sequence: Synthetic
oligonucleotide

<400> SEQUENCE: 4
agaagcguau cccgcugagc 20

<210> SEQ ID NO 5
<211> LENGTH: 8
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5 ttaattaa 8

<210> SEQ ID NO 6
<211> LENGTH: 129
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (29)..(47)
<223> OTHER INFORMATION: a, c, t, g, unknown or other

<400> SEQUENCE: 6
tctccctgag cttcagggag ttaattaann nnnnnnnnnn nnnnnnngtt ttagagctag 60
aaatagcaag ttaaaataag gctagtccgt tatcaacttg aaaaagtggc accgagtcgg 120
tgcttttt 129

<210> SEQ ID NO 7
<211> LENGTH: 130
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7
tctccctgag cttcagggag ttaattaacg tactataatc atggcccggt tttagagcta 60
gaaatagcaa gttaaaataa ggctagtccg ttatcaactt gaaaaagtgg caccgagtcg 120
gtgctttttt 130

<210> SEQ ID NO 8
<211> LENGTH: 8623
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (279)..(297)
<223> OTHER INFORMATION: a, c, t, g, unknown or other

<400> SEQUENCE: 8
gagggcctat ttcccatgat tccttcatat ttgcatatac gatacaaggc tgttagagag 60
ataattggaa ttaatttgac tgtaaacaca aagatattag tacaaaatac gtgacgtaga 120
aagtaataat ttcttgggta gtttgcagtt ttaaaattat gttttaaaat ggactatcat 180

-continued

```
atgcttaccg taacttgaaa gtatttcgat ttcttggctt tatatatctt gtggaaagga    240
cgaaacaccg tctccctgag cttcagggag ttaattaann nnnnnnnnnn nnnnnnngtt    300
ttagagctag aaatagcaag ttaaaataag gctagtccgt tatcaacttg aaaaagtggc    360
accgagtcgg tgcttttttg ttttagagct agaaatagca agttaaaata aggctagtcc    420
gtttttagcg cgtgcgccaa ttctgcagac aaatggctct agaggtaccc gttacataac    480
ttacggtaaa tggcccgcct ggctgaccgc ccaacgaccc ccgcccattg acgtcaatag    540
taacgccaat agggactttc cattgacgtc aatgggtgga gtatttacgg taaactgccc    600
acttggcagt acatcaagtg tatcatatgc caagtacgcc ccctattgac gtcaatgacg    660
gtaaatggcc cgcctggcat tgtgcccagt acatgacctt atgggacttt cctacttggc    720
agtacatcta cgtattagtc atcgctatta ccatggtcga ggtgagcccc acgttctgct    780
tcactctccc catctccccc ccctccccac ccccaatttt gtatttattt atttttttaat    840
tattttgtgc agcgatgggg gcgggggggg gggggggggcg cgcgccaggc ggggcggggc    900
ggggcgaggg gcggggcggg gcgaggcgga gaggtgcggc ggcagccaat cagagcggcg    960
cgctccgaaa gtttcctttt atggcgaggc ggcggcggcg gcggccctat aaaaagcgaa   1020
gcgcgcggcg ggcgggagtc gctgcgacgc tgccttcgcc ccgtgccccg ctccgccgcc   1080
gcctcgcgcc gcccgccccg gctctgactg accgcgttac tcccacaggt gagcgggcgg   1140
gacggccctt ctcctccggg ctgtaattag ctgagcaaga ggtaagggtt taagggatgg   1200
ttggttggtg gggtattaat gtttaattac ctggagcacc tgcctgaaat cacttttttt   1260
caggttggac cggtgccacc atgtacccat acgatgttcc agattacgct cgcgaatgct   1320
gtctaatttg aggatcctgc tcaacaatgc agctcttaga aagggtcaca cttctgtggt   1380
tcgacatttt tggtgtggga agccagtcca aagtcaagta cagctgaaag gccgtgacct   1440
cctcaccttg tcgcgagaca agaaatattc tatcggcctg gatattggaa ctaacagtgt   1500
gggctgggcc gtcatcaccg acgagtacaa agtgccaagc aagaagttca aggtcctggg   1560
aaacaccgat agacacagca tcaagaaaaa tctgattggg gccctgctct tcgactccgg   1620
cgagacagct gaagcaacta ggctgaaaag aacagctagg agacggtata ctcgccgaaa   1680
gaatcggatc tgctacctgc aggagatttt cagcaacgaa atggccaagg tggacgatag   1740
tttctttcac aggctggagg aatcattcct ggtcgaggaa gataagaaac acgagaggca   1800
tcccatcttt ggcaacattg tggacgaggt cgcttatcac gaaaagtacc ctacaatcta   1860
tcatctcagg aagaaactgg tggacagcac tgataaggca gacctgagac tcatctatct   1920
ggccctcgct cacatgatta agttccgggg ccattttctc atcgagggag atctgaaccc   1980
agacaattcc gatgtggaca agctcttcat ccagctggtc cagacataca atcagctgtt   2040
tgaggaaaac cccattaatg catcaggcgt ggacgcaaaa gccatcctca gcgccagact   2100
gtctaagagt aggagactgg agaacctcat cgctcagctg ccaggcgaaa agaaaaacgg   2160
gctctttggt aatctgattg cactgtccct cggactgacc cccaacttca agtctaattt   2220
tgatctggcc gaggacgcta aactccagct gagcaaggac acatatgacg atgacctgga   2280
taacctgctc gctcagatcg gagatcagta cgcagacctc ttcctggccg ctaagaatct   2340
gtctgacgcc atcctgctca gtgatattct gagggtgaac accgagatta caaaagcccc   2400
cctgtcagct agcatgatca agagatatga cgagcaccat caggatctga ccctgctcaa   2460
ggctctcgtg cggcagcagc tgcctgagaa gtacaaagaa atcttctttg atcagtctaa   2520
```

-continued

```
gaacggctac gccggatata ttgacggcgg agctagtcag gaggagttct acaagtttat   2580
caaacccatt ctggagaaga tggacgggac tgaggaactg ctcgtgaaac tgaatagaga   2640
ggacctgctc cggaagcagc gcaccttcga taacggctcc atccctcacc agattcatct   2700
gggagagctc cacgcaatcc tgcggcgcca ggaggacttc tacccatttc tgaaggataa   2760
ccgggagaag atcgaaaaaa ttctgacttt ccgcatcccc tactatgtgg ggcctctggc   2820
aagaggtaat agtcggtttg cctggatgac ccgcaagtca gaggaaacaa tcactccctg   2880
gaacttcgag gaagtggtcg ataagggagc ttccgcacag tctttcattg agaggatgac   2940
aaattttgac aagaacctcc caaatgaaaa agtgctgccc aagcactctc tgctctacga   3000
gtatttcacc gtctataacg aactgacaaa ggtgaaatac gtcactgagg ggatgagaaa   3060
gcctgccttc ctgagtggtg aacagaagaa agctatcgtg gacctgctct ttaaaaccaa   3120
tcggaaggtg acagtcaagc agctgaaaga ggactatttc aagaaaattg aatgtttcga   3180
ttctgtggag atcagtggcg tcgaggacag gttcaacgcc tccctgggaa cctaccacga   3240
tctgctcaag atcattaagg ataaagactt cctcgacaac gaggaaaatg aggatatcct   3300
ggaggacatt gtgctcaccc tgacactctt tgaggatcgg gaaatgatcg aggaacgcct   3360
caagacatat gcccatctgt tcgatgacaa agtgatgaaa cagctgaagc gaaggagata   3420
cactgggtgg ggtcgactct ctaggaagct gatcaacggc atcagggaca aacagagcgg   3480
aaagacaatc ctggactttc tcaagtccga tggcttcgct aacaggaact tcatgcagct   3540
cattcacgat gactccctga ctttcaaaga ggatatccag aaggcacagg tgtccggcca   3600
gggagactct ctccacgagc atatcgcaaa cctggccggg tctcctgcca tcaagaaagg   3660
tattctgcag accgtgaagg tggtcgacga gctggtgaaa gtcatgggga gacataagcc   3720
agaaaacatc gtgattgaga tggccaggga gaatcagacc acacagaagg gtcagaagaa   3780
ctcacgggag cgcatgaaac ggatcgagga aggcattaag gaactcggaa gccagatcct   3840
gaaggagcac cccgtggaaa acacacagct gcagaatgag aagctgtatc tctactatct   3900
gcagaatgga cgcgatatgt acgtggacca ggagctcgat attaaccgac tgtccgatta   3960
cgacgtggat catatcgtcc cacagtcatt cctgaaagat gacagcattg acaataaggt   4020
gctgactcgc tctgacaaaa accgagggaa gagtgataat gtcccctcag aggaagtggt   4080
caagaaaatg aagaactact ggaggcagct gctcaatgcc aaactgatca cccagcgaaa   4140
gtttgataac ctgacaaaag ctgagagggg gggtctgagt gaactcgaca aagcaggctt   4200
catcaagcga cagctggtgg agaccaggca gatcacaaag cacgtcgctc agattctgga   4260
ctcacgcatg aacaccaagt acgatgagaa tgacaaactg atccgagaag tgaaggtcat   4320
tacactcaag tcaaaactgg tgagcgactt taggaaagat ttccagtttt ataaggtcag   4380
agagatcaac aactaccacc atgctcatga cgcatacctg aacgcagtgg tcgggactgc   4440
cctcattaag aaataccccta aactggagtc cgagttcgtg tacggtgact ataaggtgta   4500
cgatgtcaga aaaatgatcg ccaagtctga gcaggaaatt ggcaaagcca ccgctaagta   4560
tttcttttac agtaacatca tgaatttctt taagactgag atcaccctgg caaatggaga   4620
aatccgaaag aggccactga ttgagactaa cggggagacc ggcgaaatcg tgtgggacaa   4680
agggagagat tttgctacag tgcggaaggt cctgagcatg ccccaagtga atattgtcaa   4740
gaaaacagag gtgcagactg gcggattcag taaggaatca attctcccta aacgcaactc   4800
cgataagctg atcgcccgaa agaaagactg ggatcctaag aaatatgggg gtttcgactc   4860
cccaaccgtg gcttactctg tcctggtggt cgcaaaggtg gagaagggga aaagcaagaa   4920
```

```
actgaaatcc gtcaaggaac tgctcggtat cacaattatg gagcggagct ccttcgaaaa   4980
gaatcctatc gattttctgg aggctaaagg ctataaggaa gtgaagaaag acctcatcat   5040
caagctgcca aagtactcac tgtttgagct cgaaaacgga agaaagcgaa tgctcgcaag   5100
cgccggagag ctgcagaagg gtaatgaact ggccctcccc tccaagtacg tgaacttcct   5160
gtatctcgct agccactacg agaagctgaa aggctcccct gaggataacg aacagaaaca   5220
gctgtttgtg gagcagcaca agcattatct ggacgagatc attgaacaga ttagcgagtt   5280
ctccaaacgc gtgatcctgg ctgacgcaaa tctcgataag gtcctgtctg catacaacaa   5340
acacagggac aagccaatca gagagcaggc cgaaaatatc attcatctgt tcactctcac   5400
caacctggga gcaccagcag ccttcaagta ttttgacact accatcgatc gcaaacgata   5460
cacaagcact aaggaggtgc tcgacgctac cctgatccac cagtctatta ctggcctgta   5520
cgagacccgg atcgacctca gtcagctggg cggagatatg tccgtcctga cgccgctgct   5580
gctgcggggc ttgacaggct cggcccggcg gctcccagtg ccgcgcgcca actcgagaag   5640
aattcctaga gctcgctgat cagcctcgac tgtgccttct agttgccagc catctgttgt   5700
ttgcccctcc cccgtgcctt ccttgaccct ggaaggtgcc actcccactg tcctttccta   5760
ataaaatgag gaaattgcat cgcattgtct gagtaggtgt cattctattc tggggggtgg   5820
ggtggggcag gacagcaagg gggaggattg ggaagagaat agcaggcatg ctggggagcg   5880
gccgcaggaa cccctagtga tggagttggc cactccctct ctgcgcgctc gctcgctcac   5940
tgaggccggg cgaccaaagg tcgcccgacg cccgggcttt gcccgggcgg cctcagtgag   6000
cgagcgagcg cgcagctgcc tgcaggggcg cctgatgcgg tattttctcc ttacgcatct   6060
gtgcggtatt tcacaccgca tacgtcaaag caaccatagt acgcgccctg tagcggcgca   6120
ttaagcgcgg cgggtgtggt ggttacgcgc agcgtgaccg ctacacttgc cagcgcccta   6180
gcgcccgctc ctttcgcttt cttcccttcc tttctcgcca cgttcgccgg ctttccccgt   6240
caagctctaa atcgggggct ccctttaggg ttccgattta gtgctttacg gcacctcgac   6300
cccaaaaaac ttgatttggg tgatggttca cgtagtgggc catcgccctg atagacggtt   6360
tttcgccctt tgacgttgga gtccacgttc tttaatagtg gactcttgtt ccaaactgga   6420
acaacactca accctatctc gggctattct tttgatttat aagggatttt gccgatttcg   6480
gcctattggt taaaaaatga gctgatttaa caaaaattta acgcgaattt taacaaaata   6540
ttaacgttta caattttatg gtgcactctc agtacaatct gctctgatgc cgcatagtta   6600
agccagcccc gacacccgcc aacacccgct gacgcgccct gacgggcttg tctgctcccg   6660
gcatccgctt acagacaagc tgtgaccgtc tccgggagct gcatgtgtca gaggttttca   6720
ccgtcatcac cgaaacgcgc gagacgaaag ggcctcgtga tacgcctatt tttataggtt   6780
aatgtcatga taataatggt ttcttagacg tcaggtggca cttttcgggg aaatgtgcgc   6840
ggaaccccta tttgtttatt tttctaaata cattcaaata tgtatccgct catgagacaa   6900
taaccctgat aaatgcttca ataatattga aaaaggaaga gtatgagtat tcaacatttc   6960
cgtgtcgccc ttattccctt ttttgcggca ttttgccttc ctgtttttgc tcacccagaa   7020
acgctggtga aagtaaaaga tgctgaagat cagttgggtg cacgagtggg ttacatcgaa   7080
ctggatctca acagcggtaa gatccttgag agttttcgcc ccgaagaacg ttttccaatg   7140
atgagcactt ttaaagttct gctatgtggc gcggtattat cccgtattga cgccgggcaa   7200
gagcaactcg gtcgccgcat acactattct cagaatgact tggttgagta ctcaccagtc   7260
```

-continued

```
acagaaaagc atcttacgga tggcatgaca gtaagagaat tatgcagtgc tgccataacc   7320

atgagtgata acactgcggc caacttactt ctgacaacga tcggaggacc gaaggagcta   7380

accgcttttt tgcacaacat gggggatcat gtaactcgcc ttgatcgttg ggaaccggag   7440

ctgaatgaag ccataccaaa cgacgagcgt gacaccacga tgcctgtagc aatggcaaca   7500

acgttgcgca aactattaac tggcgaacta cttactctag cttcccggca acaattaata   7560

gactggatgg aggcggataa agttgcagga ccacttctgc gctcggccct tccggctggc   7620

tggtttattg ctgataaatc tggagccggt gagcgtggaa gccgcggtat cattgcagca   7680

ctggggccag atggtaagcc ctcccgtatc gtagttatct acacgacggg gagtcaggca   7740

actatggatg aacgaaatag acagatcgct gagataggtg cctcactgat taagcattgg   7800

taactgtcag accaagttta ctcatatata ctttagattg atttaaaact tcatttttaa   7860

tttaaaagga tctaggtgaa gatccttttt gataatctca tgaccaaaat cccttaacgt   7920

gagttttcgt tccactgagc gtcagacccc gtagaaaaga tcaaaggatc ttcttgagat   7980

cctttttttc tgcgcgtaat ctgctgcttg caaacaaaaa aaccaccgct accagcggtg   8040

gtttgtttgc cggatcaaga gctaccaact ctttttccga aggtaactgg cttcagcaga   8100

gcgcagatac caaatactgt ccttctagtg tagccgtagt taggccacca cttcaagaac   8160

tctgtagcac cgcctacata cctcgctctg ctaatcctgt taccagtggc tgctgccagt   8220

ggcgataagt cgtgtcttac cgggttggac tcaagacgat agttaccgga taaggcgcag   8280

cggtcgggct gaacgggggg ttcgtgcaca cagcccagct tggagcgaac gacctacacc   8340

gaactgagat acctacagcg tgagctatga gaaagcgcca cgcttcccga agggagaaag   8400

gcggacaggt atccggtaag cggcagggtc ggaacaggag agcgcacgag ggagcttcca   8460

gggggaaacg cctggtatct ttatagtcct gtcgggtttc gccacctctg acttgagcgt   8520

cgatttttgt gatgctcgtc aggggggcgg agcctatgga aaaacgccag caacgcggcc   8580

tttttacggt tcctggcctt ttgctggcct tttgctcaca tgt                      8623
```

```
<210> SEQ ID NO 9
<211> LENGTH: 5732
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (422)..(440)
<223> OTHER INFORMATION: a, c, t, g, unknown or other

<400> SEQUENCE: 9

cagcagctgc gcgctcgctc gctcactgag gccgcccggg caaagcccgg gcgtcgggcg     60

acctttggtc gcccggcctc agtgagcgag cgagcgcgca gagagggagt ggggttatcg    120

gcgcgccaag gtcgggcagg aagagggcct atttcccatg attccttcat atttgcatat    180

acgatacaag gctgttagag agataattag aattaatttg actgtaaaca caaagatatt    240

agtacaaaat acgtgacgta gaaagtaata atttcttggg tagtttgcag tttttaaaat    300

tatgttttaa aatggactat catatgctta ccgtaacttg aaagtatttc gatttcttgg    360

ctttatatat cttgtggaaa ggacgaaaca ccgtctccct gagcttcagg gagttaatta    420

annnnnnnnn nnnnnnnnnn gttttagagc tagaaatagc aagttaaaat aaggctagtc    480

cgttatcaac ttgaaaaagt ggcaccgagt cggtgctttt ttcaattgtc gttacataac    540
```

-continued

```
ttacggtaaa tggcccgcct ggctgaccgc ccaacgaccc ccggactcac ggggatttcc    600
aagtctccac cccattgacg tcaatgggag tttgttttgg caccaaaatc aacgggactt    660
tccaaaatgt cgtaacaact ccgccccatt gacgcaaatg ggcggtaggc gtgtacggtg    720
ggaggtctat ataagcagag ctcgtttagt gaaccgtcag atcgcctgga gacgccatcc    780
acgctgtttt gacctccata gaagacaccg ggaccgatcc agcctccgga cctagaggat    840
ccggtactcg aggaactgaa aaaccagaaa gttaactggt aagtttagtc tttttgtctt    900
ttatttcagg tcccggatcc ggtggtggtg caaatcaaag aactgctcct cagtggatgt    960
tgcctttact tctaggcctg tacggaagtg ttacttctgc tctaaaagct gcggaattgt   1020
acccctgcag tcgacggtac cgcgggcccg ggatccaccg gtcgccacca tggtgagcaa   1080
gggcgaggag ctgttcaccg gggtggtgcc catcctggtc gagctggacg gcgacgtaaa   1140
cggccacaag ttcagcgtgt ccggcgaggg cgagggcgat gccacctacg gcaagctgac   1200
cctgaagttc atctgcacca ccggcaagct gcccgtgccc tggcccaccc tcgtgaccac   1260
cctgacctac ggcgtgcagt gcttcagccg ctaccccgac cacatgaagc agcacgactt   1320
cttcaagtcc gccatgcccg aaggctacgt ccaggagcgc accatcttct tcaaggacga   1380
cggcaactac aagacccgcg ccgaggtgaa gttcgagggc gacaccctgg tgaaccgcat   1440
cgagctgaag ggcatcgact tcaaggagga cggcaacatc ctggggcaca agctggagta   1500
caactacaac agccacaacg tctatatcat ggccgacaag cagaagaacg gcatcaaggt   1560
gaacttcaag atccgccaca acatcgagga cggcagcgtg cagctcgccg accactacca   1620
gcagaacacc cccatcggcg acggccccgt gctgctgccc gacaaccact acctgagcac   1680
ccagtccgcc ctgagcaaag accccaacga gaagcgcgat cacatggtcc tgctggagtt   1740
cgtgaccgcc gccgggatca ctctcggcat ggacgagctg tacaagtaaa gaggccggcc   1800
gcggggatcc agacatgata agatacattg atgagtttgg acaaaccaca actagaatgc   1860
agtgaaaaaa atgctttatt tgtgaaattt gtgatgctat tgctttattt gtaaccatta   1920
taagctgcaa taaacaagtt aacaacaaca attgcaacta gtgctagaag catggctacg   1980
tagataagta gcatggcggg ttaatcatta actacaagga acccctagtg atggagttgg   2040
ccactccctc tctgcgcgct cgctcgctca ctgaggccgg gcgaccaaag gtcgcccgac   2100
gcccgggctt tgcccgggcg gcctcagtga gcgagcgagc gcgcagctgg cgtaatagcg   2160
aagaggcccg caccgatcgc ccttcccaac agttgcgcag cctgaatggc gaatggcgat   2220
tccgttgcaa tggctggcgg taatattgtt ctggatatta ccagcaaggc cgatagtttg   2280
agttcttcta ctcaggcaag tgatgttatt actaatcaaa gaagtattgc gacaacggtt   2340
aatttgcgtg atggacagac tcttttactc ggtggcctca ctgattataa aaacacttct   2400
caggattctg gcgtaccgtt cctgtctaaa atccctttaa tcggcctcct gtttagctcc   2460
cgctctgatt ctaacgagga aagcacgtta tacgtgctcg tcaaagcaac catagtacgc   2520
gccctgtagc ggcgcattaa gcgcggcggg tgtggtggtt acgcgcagcg tgaccgctac   2580
acttgccagc gccctagcgc ccgctccttt cgctttcttc ccttcctttc tcgccacgtt   2640
cgccggcttt ccccgtcaag ctctaaatcg ggggctccct ttagggttcc gatttagtgc   2700
tttacggcac ctcgacccca aaaaacttga ttagggtgat ggttcacgta gtgggccatc   2760
gccctgatag acggtttttc gccctttgac gttggagtcc acgttcttta atagtggact   2820
cttgttccaa actggaacaa cactcaaccc tatctcggtc tattcttttg atttataagg   2880
gattttgccg atttcggcct attggttaaa aaatgagctg atttaacaaa aatttaacgc   2940
```

-continued

```
gaattttaac aaaatattaa cgtttacaat ttaaatattt gcttatacaa tcttcctgtt   3000
tttggggctt ttctgattat caaccggggt acatatgatt gacatgctag ttttacgatt   3060
accgttcatc gattctcttg tttgctccag actctcaggc aatgacctga tagcctttgt   3120
agagacctct caaaaatagc taccctctcc ggcatgaatt tatcagctag aacggttgaa   3180
tatcatattg atggtgattt gactgtctcc ggcctttctc acccgtttga atctttacct   3240
acacattact caggcattgc atttaaaata tatgagggtt ctaaaaattt ttatccttgc   3300
gttgaaataa aggcttctcc cgcaaaagta ttacagggtc ataatgtttt tggtacaacc   3360
gatttagctt tatgctctga ggctttattg cttaattttg ctaattcttt gccttgcctg   3420
tatgatttat tggatgttgg aatcctgatg cggtattttc tccttacgca tctgtgcggt   3480
atttcacacc gcatatggtg cactctcagt acaatctgct ctgatgccgc atagttaagc   3540
cagccccgac acccgccaac acccgctgac gcgccctgac gggcttgtct gctcccggca   3600
tccgcttaca gacaagctgt gaccgtctcc gggagctgca tgtgtcagag gttttcaccg   3660
tcatcaccga aacgcgcgag acgaaagggc ctcgtgatac gcctattttt ataggttaat   3720
gtcatgataa taatggtttc ttagacgtca ggtggcactt ttcggggaaa tgtgcgcgga   3780
acccctattt gtttattttt ctaaatacat tcaaatatgt atccgctcat gagacaataa   3840
ccctgataaa tgcttcaata atattgaaaa aggaagagta tgagtattca acatttccgt   3900
gtcgccctta ttcccttttt tgcggcattt tgccttcctg tttttgctca cccagaaacg   3960
ctggtgaaag taaaagatgc tgaagatcag ttgggtgcac gagtgggtta catcgaactg   4020
gatctcaaca gcggtaagat ccttgagagt tttcgccccg aagaacgttt tccaatgatg   4080
agcactttta aagttctgct atgtggcgcg gtattatccc gtattgacgc cgggcaagag   4140
caactcggtc gccgcataca ctattctcag aatgacttgg ttgagtactc accagtcaca   4200
gaaaagcatc ttacggatgg catgacagta agagaattat gcagtgctgc cataaccatg   4260
agtgataaca ctgcggccaa cttacttctg acaacgatcg gaggaccgaa ggagctaacc   4320
gcttttttgc acaacatggg ggatcatgta actcgccttg atcgttggga accggagctg   4380
aatgaagcca taccaaacga cgagcgtgac accacgatgc ctgtagcaat ggcaacaacg   4440
ttgcgcaaac tattaactgg cgaactactt actctagctt cccggcaaca attaatagac   4500
tggatggagg cggataaagt tgcaggacca cttctgcgct cggcccttcc ggctggctgg   4560
tttattgctg ataaatctgg agccggtgag cgtgggtctc gcggtatcat tgcagcactg   4620
gggccagatg gtaagccctc ccgtatcgta gttatctaca cgacggggag tcaggcaact   4680
atggatgaac gaaatagaca gatcgctgag ataggtgcct cactgattaa gcattggtaa   4740
ctgtcagacc aagtttactc atatatactt tagattgatt taaaacttca tttttaattt   4800
aaaaggatct aggtgaagat cctttttgat aatctcatga ccaaaatccc ttaacgtgag   4860
ttttcgttcc actgagcgtc agaccccgta gaaaagatca aaggatcttc ttgagatcct   4920
ttttttctgc gcgtaatctg ctgcttgcaa acaaaaaaac caccgctacc agcggtggtt   4980
tgtttgccgg atcaagagct accaactctt tttccgaagg taactggctt cagcagagcg   5040
cagataccaa atactgtcct tctagtgtag ccgtagttag gccaccactt caagaactct   5100
gtagcaccgc ctacatacct cgctctgcta atcctgttac cagtggctgc tgccagtggc   5160
gataagtcgt gtcttaccgg gttggactca agacgatagt taccggataa ggcgcagcgg   5220
tcgggctgaa cggggggttc gtgcacacag cccagcttgg agcgaacgac ctacaccgaa   5280
```

-continued

```
ctgagatacc tacagcgtga gctatgagaa agcgccacgc ttcccgaagg gagaaaggcg   5340

gacaggtatc cggtaagcgg cagggtcgga acaggagagc gcacgaggga gcttccaggg   5400

ggaaacgcct ggtatcttta tagtcctgtc gggtttcgcc acctctgact tgagcgtcga   5460

tttttgtgat gctcgtcagg ggggcggagc ctatggaaaa acgccagcaa cgcggccttt   5520

ttacggttcc tggccttttg ctggcctttt gctcacatgt tctttcctgc gttatcccct   5580

gattctgtgg ataaccgtat taccgccttt gagtgagctg ataccgctcg ccgcagccga   5640

acgaccgagc gcagcgagtc agtgagcgag gaagcggaag agcgcccaat acgcaaaccg   5700

cctctccccg cgcgttggcc gattcattaa tg                                 5732


<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

taatacgact cactataggg atgtacccat acgatgttcc agattacgct                50


<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

gcgagctcta ggaattctta c                                               21


<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

taatacgact cactataggg tctccctgag cttcagggag t                         41


<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

aaaagcaccg actcggtgcc                                                 20


<210> SEQ ID NO 14
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
```

<223> OTHER INFORMATION: a, c, t, g, unknown or other

<400> SEQUENCE: 14 nngrrt 6

<210> SEQ ID NO 15
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
gagggcctat ttcccatgat tccttcatat ttgcatatac gatacaaggc tgttagagag 60
ataattggaa ttaatttgac tgtaaacaca aagatattag tacaaaatac gtgacgtaga 120
aagtaataat ttcttgggta gtttgcagtt ttaaaattat gttttaaaat ggactatcat 180
atgcttaccg taacttgaaa gtatttcgat ttcttggctt tatatatctt gtggaaagga 240
cgaaacaccg gagaccacgg caggtctcag ttttagtact ctggaaacag aatctactaa 300
aacaaggcaa aatgccgtgt ttatctcgtc aacttgttgg cgagattttt g 351

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 16
ucucccugag cuucagggag ttaattaacg tactataatc atggcccg 48

<210> SEQ ID NO 17
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 17
ucucccugag cuucagggag 20

<210> SEQ ID NO 18
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(6)
<223> OTHER INFORMATION: a, c, t, g, unknown or other

<400> SEQUENCE: 18 nnnnnn 6

<210> SEQ ID NO 19
<211> LENGTH: 130
<212> TYPE: DNA

-continued

<213> ORGANISM: Artificial Sequence
<220> FEATURE:
<223> OTHER INFORMATION: Description of Artificial Sequence: Synthetic
polynucleotide

<400> SEQUENCE: 19
tctccctgag cttcagggag ttaattaacg tactataatc atggcccggt tttagagcta 60
gaaatagcaa gttaaaataa ggctagtccg ttatcaactt gaaaaagtgg caccgagtcg 120
gtgctttttt 130

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 20
agttagccac atagcacttg t 21

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21
gctagacttg ctatcagtca tcat 24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 22
gaaaccacat aaatcaagcc ctac 24

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 23
gttgtcgtag taggcaaaca ataag 25

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 24
tcctaacact cctcgtcccc 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
tggcgtctgc aaatggttgt 20

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 26
tactacagcc ccaagtct 18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
tggacccatc ttctatgc 18

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
cctgagcttc agggagttaa t 21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 29
cgactcggtg ccactttttc 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 30
tacaactacg caaaggcccc 20

<210> SEQ ID NO 31

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
tggcgtctgc aaatggttgt 20

<210> SEQ ID NO 32
<211> LENGTH: 7275
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggccactcc 540
ctctctgcgc gctcgctcgc tcactgaggc cgggcgacca aaggtcgccc gacgcccggg 600
ctttgcccgg gcggcctcag tgagcgagcg agcgcgcaga gagggagtgg ccaactccat 660
cactaggggt tccttgtagt taatgattaa cccgccatgc tacttatcta cgtagccatg 720
ctctagatta attaaactca cggggatttc caagtctcca ccccattgac gtcaatggga 780
gtttgttttg gcaccaaaat caacgggact ttccaaaatg tcgtaataac cccgccccgt 840
tgacgcaaat gggcggtagg cgtgtacggt gggaggtcta tataagcaga gctcgtttag 900
tgaaccgtca gaattctcga gtgatcgaaa gagcctgcta aagcaaaaaa gaagtcaccg 960
ctagcgccac catggatgtt gagccgggca gtgtgcggca ccagcaggca gctggctccg 1020
gttttggggt atctgggctc caggcagatg acacagttcg agggctttac caacctgtat 1080
caggtgagca agacactgcg gtttgagctg atcccacagg gcaagaccct gaagcacatc 1140
caggagcagg gcttcatcga ggaggacaag gcccgcaatg atcactacaa ggagctgaag 1200
cccatcatcg atcggatcta caagacctat gccgaccagt gcctgcagct ggtgcagctg 1260
gattgggaga acctgagcgc cgccatcgac tcctatagaa aggagaaaac cgaggagaca 1320
aggaacgccc tgatcgagga gcaggccaca tatcgcaatg ccatccacga ctacttcatc 1380
ggccggacag acaacctgac cgatgccatc aataagagac acgccgagat ctacaagggc 1440
ctgttcaagg ccgagctgtt taatggcaag gtgctgaagc agctgggcac cgtgaccaca 1500
accgagcacg agaacgccct gctgcggagc ttcgacaagt ttacaaccta cttctccggc 1560
ttttatgaga acaggaagaa cgtgttcagc gccgaggata tcagcacagc catcccacac 1620
cgcatcgtgc aggacaactt ccccaagttt aaggagaatt gtcacatctt cacacgcctg 1680
atcaccgccg tgcccagcct gcgggagcac tttgagaacg tgaagaaggc catcggcatc 1740

-continued

```
ttcgtgagca cctccatcga ggaggtgttt tccttccctt tttataacca gctgctgaca   1800
cagacccaga tcgacctgta taaccagctg ctgggaggaa tctctcggga ggcaggcacc   1860
gagaagatca agggcctgaa cgaggtgctg aatctggcca tccagaagaa tgatgagaca   1920
gcccacatca tcgcctccct gccacacaga ttcatccccc tgtttaagca gatcctgtcc   1980
gataggaaca ccctgtcttt catcctggag gagtttaaga gcgacgagga agtgatccag   2040
tccttctgca agtacaagac actgctgaga aacgagaacg tgctggagac agccgaggcc   2100
ctgtttaacg agctgaacag catcgacctg acacacatct tcatcagcca caagaagctg   2160
gagacaatca gcagcgccct gtgcgaccac tgggatacac tgaggaatgc cctgtatgag   2220
cggagaatct ccgagctgac aggcaagatc accaagtctg ccaaggagaa ggtgcagcgc   2280
agcctgaagc acgaggatat caacctgcag gagatcatct ctgccgcagg caaggagctg   2340
agcgaggcct tcaagcagaa aaccagcgag atcctgtccc acgcacacgc cgccctggat   2400
cagccactgc ctacaaccct gaagaagcag gaggagaagg agatcctgaa gtctcagctg   2460
gacagcctgc tgggcctgta ccacctgctg gactggtttg ccgtggatga gtccaacgag   2520
gtggaccccg agttctctgc ccggctgacc ggcatcaagc tggagatgga gccttctctg   2580
agcttctaca acaaggccag aaattatgcc accaagaagc cctactccgt ggagaagttc   2640
aagctgaact ttcagatgcc tacactggcc tctggctggg acgtgaataa ggagaagaac   2700
aatggcgcca tcctgtttgt gaagaacggc ctgtactatc tgggcatcat gccaaagcag   2760
aagggcaggt ataaggccct gagcttcgag cccacagaga aaaccagcga gggctttgat   2820
aagatgtact atgactactt ccctgatgcc gccaagatga tcccaaagtg cagcacccag   2880
ctgaaggccg tgacagccca ctttcagacc cacacaaccc ccatcctgct gtccaacaat   2940
ttcatcgagc ctctggagat cacaaaggag atctacgacc tgaacaatcc tgagaaggag   3000
ccaaagaagt ttcagacagc ctacgccaag aaaaccggcg accagaaggg ctacagagag   3060
gccctgtgca agtggatcga cttcacaagg gattttctgt ccaagtatac caagacaacc   3120
tctatcgatc tgtctagcct gcggccatcc tctcagtata aggacctggg cgagtactat   3180
gccgagctga atcccctgct gtaccacatc agcttccaga gaatcgccga gaaggagatc   3240
atggatgccg tggagacagg caagctgtac ctgttccaga tctataacaa ggactttgcc   3300
aagggccacc acggcaagcc taatctgcac acactgtatt ggaccggcct gttttctcca   3360
gagaacctgg ccaagacaag catcaagctg aatggccagg ccgagctgtt ctaccgccct   3420
aagtccagga tgaagaggat ggcacaccgg ctgggagaga agatgctgaa caagaagctg   3480
aaggatcaga aaaccccaat ccccgacacc ctgtaccagg agctgtacga ctatgtgaat   3540
cacagactgt cccacgacct gtctgatgag gccagggccc tgctgcccaa cgtgatcacc   3600
aaggaggtgt ctcacgagat catcaaggat aggcgcttta ccagcgacaa gttctttttc   3660
cacgtgccta tcacactgaa ctatcaggcc gccaattccc catctaagtt caaccagagg   3720
gtgaatgcct acctgaagga gcaccccgag acacctatca tcggcatcga tcggggcgag   3780
agaaacctga tctatatcac agtgatcgac tccaccggca agatcctgga gcagcggagc   3840
ctgaacacca tccagcagtt tgattaccag aagaagctgg acaacaggga gaaggagagg   3900
gtggcagcaa ggcaggcctg gtctgtggtg ggcacaatca aggatctgaa gcagggctat   3960
ctgagccagg tcatccacga gatcgtggac ctgatgatcc actaccaggc cgtggtggtg   4020
ctggagaacc tgaatttcgg ctttaagagc aagaggaccg gcatcgccga gaaggccgtg   4080
```

-continued

```
taccagcagt tcgagaagat gctgatcgat aagctgaatt gcctggtgct gaaggactat   4140
ccagcagaga aagtgggagg cgtgctgaac ccataccagc tgacagacca gttcacctcc   4200
tttgccaaga tgggcaccca gtctggcttc ctgttttacg tgcctgcccc atatacatct   4260
aagatcgatc ccctgaccgg cttcgtggac cccttcgtgt ggaaaaccat caagaatcac   4320
gagagccgca agcacttcct ggagggcttc gactttctgc actacgacgt gaaaaccggc   4380
gacttcatcc tgcactttaa gatgaacaga aatctgtcct tccagagggg cctgcccggc   4440
tttatgcctg catgggatat cgtgttcgag aagaacgaga cacagtttga cgccaagggc   4500
accccctttca tcgccggcaa gagaatcgtg ccagtgatcg agaatcacag attcaccggc   4560
agataccggg acctgtatcc tgccaacgag ctgatcgccc tgctggagga gaagggcatc   4620
gtgttcaggg atggctccaa catcctgcca aagctgctgg agaatgacga ttctcacgcc   4680
atcgacacca tggtggccct gatccgcagc gtgctgcaga tgcggaactc caatgccgcc   4740
acaggcgagg actatatcaa cagccccgtg cgcgatctga atggcgtgtg cttcgactcc   4800
cggtttcaga acccagagtg gcccatggac gccgatgcca atggcgccta ccacatcgcc   4860
ctgaagggcc agctgctgct gaatcacctg aaggagagca aggatctgaa gctgcagaac   4920
ggcatctcca atcaggactg gctggcctac atccaggagc tgcgcaacat gtccgtcctg   4980
acgccgctgc tgctgcgggg cttgacaggc tcggcccggc ggctcccagt gccgcgcgcc   5040
aagcggccgc aataaaagat ctttattttc attagatctg tgtgttggtt ttttgtgtgt   5100
ctagacatgg ctacgtagat aattagcatg gcgggttaat cattaaagga acccctagtg   5160
atggagttgg ccactccctc tctgcgcgct cgctcgctca ctgaggccgg gcgaccaaag   5220
gtcgcccgac gcccgggctt tgcccgggcg gcctcagtga gcgagcgagc gcgcagagag   5280
ggagtggcca gctgcattaa tgaatcggcc aacgcgcggg gagaggcggt ttgcgtattg   5340
ggcgctcttc cgcttcctcg ctcactgact cgctgcgctc ggtcgttcgg ctgcggcgag   5400
cggtatcagc tcactcaaag gcggtaatac ggttatccac agaatcaggg gataacgcag   5460
gaaagaacat gtgagcaaaa ggccagcaaa aggccaggaa ccgtaaaaag gccgcgttgc   5520
tggcgttttt ccataggctc cgcccccctg acgagcatca caaaaatcga cgctcaagtc   5580
agaggtggcg aaacccgaca ggactataaa gataccaggc gtttccccct ggaagctccc   5640
tcgtgcgctc tcctgttccg accctgccgc ttaccggata cctgtccgcc tttctccctt   5700
cgggaagcgt ggcgctttct catagctcac gctgtaggta tctcagttcg gtgtaggtcg   5760
ttcgctccaa gctgggctgt gtgcacgaac cccccgttca gcccgaccgc tgcgccttat   5820
ccggtaacta tcgtcttgag tccaacccgg taagacacga cttatcgcca ctggcagcag   5880
ccactggtaa caggattagc agagcgaggt atgtaggcgg tgctacagag ttcttgaagt   5940
ggtggcctaa ctacggctac actagaagga cagtatttgg tatctgcgct ctgctgaagc   6000
cagttacctt cggaaaaaga gttggtagct cttgatccgg caaacaaacc accgctggta   6060
gcggtggttt ttttgtttgc aagcagcaga ttacgcgcag aaaaaaagga tctcaagaag   6120
atcctttgat cttttctacg gggtctgacg ctcagtggaa cgaaaactca cgttaaggga   6180
ttttggtcat gagattatca aaaaggatct tcacctagat ccttttaaat taaaaatgaa   6240
gttttaaatc aatctaaagt atatatgagt aaacttggtc tgacagttac caatgcttaa   6300
tcagtgaggc acctatctca gcgatctgtc tatttcgttc atccatagtt gcctgactcc   6360
ccgtcgtgta gataactacg atacgggagg gcttaccatc tggccccagt gctgcaatga   6420
taccgcgaga cccacgctca ccggctccag atttatcagc aataaaccag ccagccggaa   6480
```

-continued gggccgagcg cagaagtggt cctgcaactt tatccgcctc catccagtct attaattgtt 6540
gccgggaagc tagagtaagt agttcgccag ttaatagttt gcgcaacgtt gttgccattg 6600
ctacaggcat cgtggtgtca cgctcgtcgt ttggtatggc ttcattcagc tccggttccc 6660
aacgatcaag gcgagttaca tgatccccca tgttgtgcaa aaaagcggtt agctccttcg 6720
gtcctccgat cgttgtcaga agtaagttgg ccgcagtgtt atcactcatg gttatggcag 6780
cactgcataa ttctcttact gtcatgccat ccgtaagatg cttttctgtg actggtgagt 6840
actcaaccaa gtcattctga gaatagtgta tgcggcgacc gagttgctct tgcccggcgt 6900
caatacggga taataccgcg ccacatagca gaactttaaa agtgctcatc attggaaaac 6960
gttcttcggg gcgaaaactc tcaaggatct taccgctgtt gagatccagt tcgatgtaac 7020
ccactcgtgc acccaactga tcttcagcat cttttacttt caccagcgtt tctgggtgag 7080
caaaaacagg aaggcaaaat gccgcaaaaa agggaataag ggcgacacgg aaatgttgaa 7140
tactcatact cttccttttt caatattatt gaagcattta tcagggttat tgtctcatga 7200
gcggatacat atttgaatgt atttagaaaa ataaacaaat aggggttccg cgcacatttc 7260
cccgaaaagt gccac 7275

<210> SEQ ID NO 33
<211> LENGTH: 6744
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33
ctaaattgta agcgttaata ttttgttaaa attcgcgtta aatttttgtt aaatcagctc 60 atttttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggccactcc 540
ctctctgcgc gctcgctcgc tcactgaggc cgggcgacca aaggtcgccc gacgcccggg 600
ctttgcccgg gcggcctcag tgagcgagcg agcgcgcaga gagggagtgg ccaactccat 660
cactaggggt tccttgtagt taatgattaa cccgccatgc tacttatcta cgtagccatg 720
ctctagatta attaaactca cggggatttc caagtctcca ccccattgac gtcaatggga 780
gtttgttttg gcaccaaaat caacgggact ttccaaaatg tcgtaataac cccgccccgt 840
tgacgcaaat gggcggtagg cgtgtacggt gggaggtcta tataagcaga gctcgtttag 900
tgaaccgtca gaattctcga gtgatcgaaa gagcctgcta aagcaaaaaa gaagtcaccg 960
ctagcgccac catggatgtt gagccgggca gtgtgcggca ccagcaggca gctggctccg 1020
gttttggggt atctgggctc caggcagatg gccgtcaaat ccatcaaagt gaaacttcgt 1080
ctcgacgata tgccggagat tcgggccggt ctatggaaac ttcataagga agtcaatgcg 1140
ggggttcgat attacacgga atggctcagt cttctccgtc aagagaactt gtatcgaaga 1200

```
agtccgaatg gggacggaga gcaagaatgt gataagactg cagaagaatg caaagccgaa   1260
ttgttggagc ggctgcgcgc gcgtcaagtg gagaatggac accgtggtcc ggcgggatcg   1320
gacgatgaat tgctgcagtt ggcgcgtcaa ctctatgagt tgttggttcc gcaggcgata   1380
ggtgcgaaag gcgacgcgca gcaaattgcc cgcaaatttt tgagcccctt ggccgacaag   1440
gacgcagttg gtgggcttgg aatcgcgaag gcggggaaca aaccgcggtg ggttcgcatg   1500
cgcgaagcgg gggaaccagg ctgggaagag gagaaggaga aggctgagac gaggaaatct   1560
gcggatcgga ctgcggatgt tttgcgcgcg ctcgcggatt ttgggttaaa gccactgatg   1620
cgcgtataca ccgattctga gatgtcatcg gtggagtgga aaccgcttcg gaagggacaa   1680
gccgttcgga cgtgggatag ggacatgttc caacaagcta tcgaacggat gatgtcgtgg   1740
gagtcgtgga atcagcgcgt tgggcaagag tacgcgaaac tcgtagaaca aaaaaatcga   1800
tttgagcaga agaatttcgt cggccaggaa catctggtcc atctcgtcaa tcagttgcaa   1860
caagatatga aagaagcatc gcccggactc gaatcgaaag agcaaaccgc gcactatgtg   1920
acgggacggg cattgcgcgg atcggacaag gtatttgaga agtgggggaa actcgccccc   1980
gatgcacctt tcgatttgta cgacgccgaa atcaagaatg tgcagagacg taacacgaga   2040
cgattcggat cacatgactt gttcgcaaaa ttggcagagc cagagtatca ggccctgtgg   2100
cgcgaagatg cttcgtttct cacgcgttac gcggtgtaca acagcatcct tcgcaaactg   2160
aatcacgcca aaatgttcgc gacgtttact ttgccggatg caacggcgca cccgatttgg   2220
actcgcttcg ataaattggg tgggaatttg caccagtaca ccttttttgtt caacgaattt   2280
ggagaacgca ggcacgcgat tcgttttcac aagctattga aagtcgagaa tggtgtcgca   2340
agagaagttg atgatgtcac cgtgcccatt tcaatgtcag agcaattgga taatctgctt   2400
cccagagatc ccaatgaacc gattgcgcta tattttcgag attacggagc cgaacagcat   2460
ttcacaggtg aatttggtgg cgcgaagatc cagtgccgcc gggatcagct ggctcatatg   2520
caccgacgca gaggggcgag ggatgtttat ctcaatgtca gcgtacgtgt gcagagtcag   2580
tctgaggcgc ggggagaacg tcgcccgccg tatgcggcag tatttcgtct ggtcggggac   2640
aaccatcgcg cgtttgtcca tttcgataaa ctatcggatt atcttgcgga acatccggat   2700
gatgggaagc tcgggtcgga ggggttgctt tccgggctgc gggtgatgag tgtcgatctc   2760
ggccttcgca catctgcatc gatttccgtt tttcgcgttg cccggaagga cgagttgaag   2820
ccgaactcaa aaggtcgtgt accgtttttc tttccgataa aagggaatga caatctcgtc   2880
gcggttcatg agcgatcaca actcttgaag ctgcctggcg aaacggagtc gaaggacctg   2940
cgtgctatcc gagaagaacg ccaacggaca ttgcggcagt tgcggacgca actggcgtat   3000
ttgcggctgc tcgtgcggtg tgggtcggaa gatgtggggc ggcgtgaacg gagttgggca   3060
aagcttatcg agcagccggt ggatgcggcc aatcacatga caccggattg gcgcgaggct   3120
tttgaaaacg aacttcagaa gcttaagtca ctccatggta tctgtagcga caaggaatgg   3180
atggatgctg tctacgagag cgttcgccgc gtgtggcgtc acatgggcaa acaggttcgc   3240
gattggcgaa aggacgtacg aagcggagag cggcccaaga ttcgcggcta tgcgaaagac   3300
gtggtcggtg gaaactcgat tgagcaaatc gagtatctgg aacgtcagta caagttcctc   3360
aagagttgga gcttctttgg taaggtgtcg ggacaagtga ttcgtgcgga gaagggatct   3420
cgttttgcga tcacgctgcg cgaacacatt gatcacgcga aggaagatcg gctgaagaaa   3480
ttggcggatc gcatcattat ggaggctctc ggctatgtgt acgcgttgga tgagcgcggc   3540
```

-continued

```
aaaggaaagt gggttgcgaa gtatccgccg tgccagctca tcctgctgga ggaattgagc   3600
gagtaccagt tcaataacga caggcctccg agcgaaaaca accagttgat gcaatggagt   3660
catcgcggcg tgttccagga gttgataaat caggcccaag tccatgattt actcgttggg   3720
acgatgtatg cagcgttctc gtcgcgattc gacgcgcgaa ctggggcacc gggtatccgc   3780
tgtcgccggg ttccggcgcg ttgcacccag gagcacaatc cagaaccatt tccttggtgg   3840
ctgaacaagt ttgtggtgga acatacgttg gatgcttgtc ccctacgcgc agacgacctc   3900
atcccaacgg gtgaaggaga gatttttgtc tcgccgttca gcgcggagga gggggacttt   3960
catcagattc acgccgacct gaatgcggcg caaaatctgc agcagcgact ctggtctgat   4020
tttgatatca gtcaaattcg gttgcggtgt gattggggtg aagtggacgg tgaactcgtt   4080
ctgatcccaa ggcttacagg aaaacgaacg gcggattcat atagcaacaa ggtgttttat   4140
accaatacag gtgtcaccta ttatgagcga gagcggggga agaagcggag aaaggttttc   4200
gcgcaagaga aattgtcgga ggaagaggcg gagttgctcg tggaagcaga cgaggcgagg   4260
gagaaatcgg tcgttttgat gcgtgatccg tctggcatca tcaatcgggg aaattggacc   4320
aggcaaaagg aattttggtc gatggtgaac cagcggatcg aaggatactt ggtcaagcag   4380
attcgctcgc gcgttccatt acaagatagt gcgtgtgaaa acacggggga tatttaaatg   4440
tccgtcctga cgccgctgct gctgcggggc ttgacaggct cggcccggcg gctcccagtg   4500
ccgcgcgcca agcggccgca ataaaagatc tttattttca ttagatctgt gtgttggttt   4560
tttgtgtgtc tagacatggc tacgtagata attagcatgg cgggttaatc attaaaggaa   4620
cccctagtga tggagttggc cactccctct ctgcgcgctc gctcgctcac tgaggccggg   4680
cgaccaaagg tcgcccgacg cccgggcttt gcccgggcgg cctcagtgag cgagcgagcg   4740
cgcagagagg gagtggccag ctgcattaat gaatcggcca acgcgcgggg agaggcggtt   4800
tgcgtattgg gcgctcttcc gcttcctcgc tcactgactc gctgcgctcg gtcgttcggc   4860
tgcggcgagc ggtatcagct cactcaaagg cggtaatacg gttatccaca gaatcagggg   4920
ataacgcagg aaagaacatg tgagcaaaag gccagcaaaa ggccaggaac cgtaaaaagg   4980
ccgcgttgct ggcgtttttc cataggctcc gcccccctga cgagcatcac aaaaatcgac   5040
gctcaagtca gaggtggcga aacccgacag gactataaag ataccaggcg tttccccctg   5100
gaagctccct cgtgcgctct cctgttccga ccctgccgct taccggatac ctgtccgcct   5160
ttctcccttc gggaagcgtg gcgctttctc atagctcacg ctgtaggtat ctcagttcgg   5220
tgtaggtcgt tcgctccaag ctgggctgtg tgcacgaacc ccccgttcag cccgaccgct   5280
gcgccttatc cggtaactat cgtcttgagt ccaacccggt aagacacgac ttatcgccac   5340
tggcagcagc cactggtaac aggattagca gagcgaggta tgtaggcggt gctacagagt   5400
tcttgaagtg gtggcctaac tacggctaca ctagaaggac agtatttggt atctgcgctc   5460
tgctgaagcc agttaccttc ggaaaaagag ttggtagctc ttgatccggc aaacaaacca   5520
ccgctggtag cggtggtttt tttgtttgca agcagcagat tacgcgcaga aaaaaaggat   5580
ctcaagaaga tcctttgatc ttttctacgg ggtctgacgc tcagtggaac gaaaactcac   5640
gttaagggat tttggtcatg agattatcaa aaaggatctt cacctagatc cttttaaatt   5700
aaaaatgaag ttttaaatca atctaaagta tatatgagta aacttggtct gacagttacc   5760
aatgcttaat cagtgaggca cctatctcag cgatctgtct atttcgttca tccatagttg   5820
cctgactccc cgtcgtgtag ataactacga tacgggaggg cttaccatct ggccccagtg   5880
ctgcaatgat accgcgagac ccacgctcac cggctccaga tttatcagca ataaaccagc   5940
```

cagccggaag ggccgagcgc agaagtggtc ctgcaacttt atccgcctcc atccagtcta 6000
ttaattgttg ccgggaagct agagtaagta gttcgccagt taatagtttg cgcaacgttg 6060
ttgccattgc tacaggcatc gtggtgtcac gctcgtcgtt tggtatggct tcattcagct 6120
ccggttccca acgatcaagg cgagttacat gatcccccat gttgtgcaaa aaagcggtta 6180
gctccttcgg tcctccgatc gttgtcagaa gtaagttggc cgcagtgtta tcactcatgg 6240
ttatggcagc actgcataat tctcttactg tcatgccatc cgtaagatgc ttttctgtga 6300
ctggtgagta ctcaaccaag tcattctgag aatagtgtat gcggcgaccg agttgctctt 6360
gcccggcgtc aatacgggat aataccgcgc cacatagcag aactttaaaa gtgctcatca 6420
ttggaaaacg ttcttcgggg cgaaaactct caaggatctt accgctgttg agatccagtt 6480
cgatgtaacc cactcgtgca cccaactgat cttcagcatc ttttactttc accagcgttt 6540
ctgggtgagc aaaaacagga aggcaaaatg ccgcaaaaaa gggaataagg gcgacacgga 6600
aatgttgaat actcatactc ttcctttttc aatattattg aagcatttat cagggttatt 6660
gtctcatgag cggatacata tttgaatgta tttagaaaaa taaacaaata ggggttccgc 6720
gcacatttcc ccgaaaagtg ccac 6744

<210> SEQ ID NO 34
<211> LENGTH: 6546
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggccactcc 540
ctctctgcgc gctcgctcgc tcactgaggc cgggcgacca aaggtcgccc gacgcccggg 600
ctttgcccgg gcggcctcag tgagcgagcg agcgcgcaga gagggagtgg ccaactccat 660
cactaggggt tccttgtagt taatgattaa cccgccatgc tacttatcta cgtagccatg 720
ctctagatta attaaactca cggggatttc caagtctcca ccccattgac gtcaatggga 780
gtttgttttg gcaccaaaat caacgggact ttccaaaatg tcgtaataac cccgccccgt 840
tgacgcaaat gggcggtagg cgtgtacggt gggaggtcta tataagcaga gctcgtttag 900
tgaaccgtca gaattctcga gtgatcgaaa gagcctgcta aagcaaaaaa gaagtcaccg 960
ctagcgccac catggatgtt gagccgggca gtgtgcggca ccagcaggca gctggctccg 1020
gttttggggt atctgggctc caggcagaag cggaaggtcg gtatccacgg agtcccagca 1080
gccaagcgga actacatcct gggcctggac atcggcatca ccagcgtggg ctacggcatc 1140
atcgactacg agacacggga cgtgatcgat gccggcgtgc ggctgttcaa agaggccaac 1200

```
gtggaaaaca acgagggcag gcggagcaag agaggcgcca gaaggctgaa gcggcggagg   1260
cggcatagaa tccagagagt gaagaagctg ctgttcgact acaacctgct gaccgaccac   1320
agcgagctga gcggcatcaa cccctacgag gccagagtga agggcctgag ccagaagctg   1380
agcgaggaag agttctctgc cgccctgctg cacctggcca agagaagagg cgtgcacaac   1440
gtgaacgagg tggaagagga caccggcaac gagctgtcca ccaaagagca gatcagccgg   1500
aacagcaagg ccctggaaga gaaatacgtg gccgaactgc agctggaacg gctgaagaaa   1560
gacggcgaag tgcggggcag catcaacaga ttcaagacca gcgactacgt gaaagaagcc   1620
aaacagctgc tgaaggtgca gaaggcctac caccagctgg accagagctt catcgacacc   1680
tacatcgacc tgctggaaac ccggcggacc tactatgagg gacctggcga gggcagcccc   1740
ttcggctgga aggacatcaa agaatggtac gagatgctga tgggccactg cacctacttc   1800
cccgaggaac tgcggagcgt gaagtacgcc tacaacgccg acctgtacaa cgccctgaac   1860
gacctgaaca atctcgtgat caccagggac gagaacgaga agctggaata ttacgagaag   1920
ttccagatca tcgagaacgt gttcaagcag aagaagaagc ccaccctgaa gcagatcgcc   1980
aaagaaatcc tcgtgaacga agaggatatt aagggctaca gagtgaccag caccggcaag   2040
cccgagttca ccaacctgaa ggtgtaccac gacatcaagg acattaccgc ccggaaagag   2100
attattgaga acgccgagct gctggatcag attgccaaga tcctgaccat ctaccagagc   2160
agcgaggaca tccaggaaga actgaccaat ctgaactccg agctgaccca ggaagagatc   2220
gagcagatct ctaatctgaa gggctatacc ggcacccaca acctgagcct gaaggccatc   2280
aacctgatcc tggacgagct gtggcacacc aacgacaacc agatcgctat cttcaaccgg   2340
ctgaagctgg tgcccaagaa ggtggacctg tcccagcaga aagagatccc caccaccctg   2400
gtggacgact tcatcctgag ccccgtcgtg aagagaagct tcatccagag catcaaagtg   2460
atcaacgcca tcatcaagaa gtacggcctg cccaacgaca tcattatcga gctggcccgc   2520
gagaagaact ccaaggacgc ccagaaaatg atcaacgaga tgcagaagcg gaaccggcag   2580
accaacgagc ggatcgagga aatcatccgg accaccggca aagagaacgc caagtacctg   2640
atcgagaaga tcaagctgca cgacatgcag gaaggcaagt gcctgtacag cctggaagcc   2700
atccctctgg aagatctgct gaacaacccc ttcaactatg aggtggacca catcatcccc   2760
agaagcgtgt ccttcgacaa cagcttcaac aacaaggtgc tcgtgaagca ggaagaaaac   2820
agcaagaagg gcaaccggac cccattccag tacctgagca gcagcgacag caagatcagc   2880
tacgaaacct tcaagaagca catcctgaat ctggccaagg gcaagggcag aatcagcaag   2940
accaagaaag agtatctgct ggaagaacgg gacatcaaca ggttctccgt gcagaaagac   3000
ttcatcaacc ggaacctggt ggataccaga tacgccacca gaggcctgat gaacctgctg   3060
cggagctact tcagagtgaa caacctggac gtgaaagtga agtccatcaa tggcggcttc   3120
accagctttc tgcggcggaa gtggaagttt aagaaagagc ggaacaaggg gtacaagcac   3180
cacgccgagg acgccctgat cattgccaac gccgatttca tcttcaaaga gtggaagaaa   3240
ctggacaagg ccaaaaaagt gatggaaaac cagatgttcg aggaaaagca ggccgagagc   3300
atgcccgaga tcgaaaccga gcaggagtac aaagagatct tcatcacccc ccaccagatc   3360
aagcacatta aggacttcaa ggactacaag tacagccacc gggtggacaa gaagcctaat   3420
agagagctga ttaacgacac cctgtactcc acccggaagg acgacaaggg caacaccctg   3480
atcgtgaaca atctgaacgg cctgtacgac aaggacaatg acaagctgaa aaagctgatc   3540
```

-continued

```
aacaagagcc ccgaaaagct gctgatgtac caccacgacc cccagaccta ccagaaactg   3600
aagctgatta tggaacagta cggcgacgag aagaatcccc tgtacaagta ctacgaggaa   3660
accgggaact acctgaccaa gtactccaaa aaggacaacg gccccgtgat caagaagatt   3720
aagtattacg gcaacaaact gaacgcccat ctggacatca ccgacgacta ccccaacagc   3780
agaaacaagg tcgtgaagct gtccctgaag ccctacagat tcgacgtgta cctggacaat   3840
ggcgtgtaca agttcgtgac cgtgaagaat ctggatgtga tcaaaaaaga aaactactac   3900
gaagtgaata gcaagtgcta tgaggaagct aagaagctga agaagatcag caaccaggcc   3960
gagtttatcg cctccttcta caacaacgat ctgatcaaga tcaacggcga gctgtataga   4020
gtgatcggcg tgaacaacga cctgctgaac cggatcgaag tgaacatgat cgacatcacc   4080
taccgcgagt acctggaaaa catgaacgac aagaggcccc ccaggatcat taagacaatc   4140
gcctccaaga cccagagcat taagaagtac agcacagaca ttctgggcaa cctgtatgaa   4200
gtgaaatcta agaagcaccc tcagatcatc aaaaagggca tgtccgtcct gacgccgctg   4260
ctgctgcggg gcttgacagg ctcggcccgg cggctcccag tgccgcgcgc caagcggccg   4320
caataaaaga tctttatttt cattagatct gtgtgttggt tttttgtgtg tctagacatg   4380
gctacgtaga taattagcat ggcgggttaa tcattaaagg aacccctagt gatggagttg   4440
gccactccct ctctgcgcgc tcgctcgctc actgaggccg ggcgaccaaa ggtcgcccga   4500
cgcccgggct ttgcccgggc ggcctcagtg agcgagcgag cgcgcagaga gggagtggcc   4560
agctgcatta atgaatcggc caacgcgcgg ggagaggcgg tttgcgtatt gggcgctctt   4620
ccgcttcctc gctcactgac tcgctgcgct cggtcgttcg gctgcggcga gcggtatcag   4680
ctcactcaaa ggcggtaata cggttatcca cagaatcagg ggataacgca ggaaagaaca   4740
tgtgagcaaa aggccagcaa aaggccagga accgtaaaaa ggccgcgttg ctggcgtttt   4800
tccataggct ccgcccccct gacgagcatc acaaaaatcg acgctcaagt cagaggtggc   4860
gaaacccgac aggactataa agataccagg cgtttccccc tggaagctcc ctcgtgcgct   4920
ctcctgttcc gaccctgccg cttaccggat acctgtccgc ctttctccct tcgggaagcg   4980
tggcgctttc tcatagctca cgctgtaggt atctcagttc ggtgtaggtc gttcgctcca   5040
agctgggctg tgtgcacgaa ccccccgttc agcccgaccg ctgcgcctta tccggtaact   5100
atcgtcttga gtccaacccg gtaagacacg acttatcgcc actggcagca gccactggta   5160
acaggattag cagagcgagg tatgtaggcg gtgctacaga gttcttgaag tggtggccta   5220
actacggcta cactagaagg acagtatttg gtatctgcgc tctgctgaag ccagttacct   5280
tcggaaaaag agttggtagc tcttgatccg gcaaacaaac caccgctggt agcggtggtt   5340
tttttgtttg caagcagcag attacgcgca gaaaaaaagg atctcaagaa gatcctttga   5400
tcttttctac ggggtctgac gctcagtgga acgaaaactc acgttaaggg attttggtca   5460
tgagattatc aaaaaggatc ttcacctaga tccttttaaa ttaaaaatga agttttaaat   5520
caatctaaag tatatatgag taaacttggt ctgacagtta ccaatgctta atcagtgagg   5580
cacctatctc agcgatctgt ctatttcgtt catccatagt tgcctgactc cccgtcgtgt   5640
agataactac gatacgggag ggcttaccat ctggccccag tgctgcaatg ataccgcgag   5700
acccacgctc accggctcca gatttatcag caataaacca gccagccgga agggccgagc   5760
gcagaagtgg tcctgcaact ttatccgcct ccatccagtc tattaattgt tgccgggaag   5820
ctagagtaag tagttcgcca gttaatagtt tgcgcaacgt tgttgccatt gctacaggca   5880
tcgtggtgtc acgctcgtcg tttggtatgg cttcattcag ctccggttcc caacgatcaa   5940
```

ggcgagttac atgatccccc atgttgtgca aaaaagcggt tagctccttc ggtcctccga 6000
tcgttgtcag aagtaagttg gccgcagtgt tatcactcat ggttatggca gcactgcata 6060
attctcttac tgtcatgcca tccgtaagat gcttttctgt gactggtgag tactcaacca 6120
agtcattctg agaatagtgt atgcggcgac cgagttgctc ttgcccggcg tcaatacggg 6180
ataataccgc gccacatagc agaactttaa aagtgctcat cattggaaaa cgttcttcgg 6240
ggcgaaaact ctcaaggatc ttaccgctgt tgagatccag ttcgatgtaa cccactcgtg 6300
cacccaactg atcttcagca tcttttactt tcaccagcgt ttctgggtga gcaaaaacag 6360
gaaggcaaaa tgccgcaaaa aagggaataa gggcgacacg gaaatgttga atactcatac 6420
tcttcctttt tcaatattat tgaagcattt atcagggtta ttgtctcatg agcggataca 6480
tatttgaatg tatttagaaa aataaacaaa taggggttcc gcgcacattt ccccgaaaag 6540
tgccac 6546

<210> SEQ ID NO 35
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
gcaaactcca actacgaacg gatccacagc cgtactataa tcatggcccg ag 52

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 36
ucucccugag cuucagggag 20

<210> SEQ ID NO 37
<211> LENGTH: 124
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 37
ucucccugag cuucagggag uuaauuaacg uacuauaauc auggcccggu uuuagagcua 60
gaaauagcaa guuaaaauaa ggcuaguccg uuaucaacuu gaaaaagugg caccgagucg 120
gugc 124

<210> SEQ ID NO 38
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 38
gagggcctat ttcccatgat tccttcatat ttgcatatac gatacaaggc tgttagagag 60

-continued

```
ataattggaa ttaatttgac tgtaaacaca aagatattag tacaaaatac gtgacgtaga    120

aagtaataat ttcttgggta gtttgcagtt ttaaaattat gttttaaaat ggactatcat    180

atgcttaccg taacttgaaa gtatttcgat ttcttggctt tatatatctt gtggaaagga    240

cgaaacaccg gagaccacgg caggtctcag ttttagtact ctggaaacag aatctactaa    300

aacaaggcaa aatgccgtgt ttatctcgtc aacttgttgg cgagattttt g             351
```

UNITED STATES PATENT AND TRADEMARK OFFICE
CERTIFICATE OF CORRECTION

| | |
|---|---|
| PATENT NO. | : 11,492,614 B2 |
| APPLICATION NO. | : 16/461355 |
| DATED | : November 8, 2022 |
| INVENTOR(S) | : Kenneth John McLaughlin and Syed-Rehan Ashfaq Hussain |

It is certified that error appears in the above-identified patent and that said Letters Patent is hereby corrected as shown below:

In the Claims

At Column 100, Line 21 – "hSORD2-MLS" should be replaced with "hSOD2-MLS".

Signed and Sealed this
Twenty-eighth Day of March, 2023

Katherine Kelly Vidal
*Director of the United States Patent and Trademark Office*